(12) United States Patent
Mitchell et al.

(10) Patent No.: US 7,259,164 B2
(45) Date of Patent: Aug. 21, 2007

(54) CERTAIN SUBSTITUTED IMIDAZO[1,2-A]PYRAZINES, AS MODULATORS OF KINASE ACTIVITY

(75) Inventors: Scott A. Mitchell, East Haven, CT (US); Robert W. DeSimone, Durham, CT (US); James W. Darrow, Wallingford, CT (US); Douglas A. Pippin, Branford, CT (US); M. Diana Danca, North Haven, CT (US)

(73) Assignee: CGI Pharmaceuticals, Inc., Branford, CT (US)

( * ) Notice: Subject to any disclaimer, the term of this patent is extended or adjusted under 35 U.S.C. 154(b) by 367 days.

(21) Appl. No.: 10/915,696

(22) Filed: Aug. 11, 2004

(65) Prior Publication Data

US 2005/0085484 A1 Apr. 21, 2005

Related U.S. Application Data

(60) Provisional application No. 60/589,738, filed on Jul. 21, 2004, provisional application No. 60/540,938, filed on Jan. 30, 2004, provisional application No. 60/494,179, filed on Aug. 11, 2003.

(51) Int. Cl.
| | |
|---|---|
| A01N 43/58 | (2006.01) |
| A01N 43/60 | (2006.01) |
| A61K 31/50 | (2006.01) |
| A61K 31/495 | (2006.01) |
| C07D 471/00 | (2006.01) |

(52) U.S. Cl. ..................... 514/249; 544/350
(58) Field of Classification Search ............ None
See application file for complete search history.

(56) References Cited

U.S. PATENT DOCUMENTS

| | | | |
|---|---|---|---|
| 5,593,997 | A | 1/1997 | Dow et al. |
| 5,658,857 | A | 8/1997 | Andree et al. |
| 5,783,576 | A | 7/1998 | Roos et al. |
| 6,919,340 | B2 * | 7/2005 | Currie et al. ............ 514/249 |
| 6,919,341 | B2 * | 7/2005 | Paruch et al. ........... 514/249 |
| 7,160,885 | B2 | 1/2007 | Currie et al. |
| 2003/0212073 | A1 | 11/2003 | Currie et al. |
| 2004/0063715 | A1 | 4/2004 | Paruch et al. |
| 2004/0067951 | A1 | 4/2004 | DeSimone et al. |
| 2004/0072835 | A1 | 4/2004 | Paruch et al. |
| 2004/0220189 | A1 | 11/2004 | Sun et al. |
| 2005/0009832 | A1 | 1/2005 | Sun et al. |
| 2005/0054648 | A1 | 3/2005 | Mitchell et al. |
| 2005/0054649 | A1 | 3/2005 | Currie et al. |

FOREIGN PATENT DOCUMENTS

| | | |
|---|---|---|
| DE | 0 43 37 609 | 5/1995 |
| EP | 0 480 713 | 4/1992 |
| WO | WO88/04298 | 6/1988 |
| WO | WO95/12594 | 5/1995 |

(Continued)

OTHER PUBLICATIONS

Ding et al. (2002) "A Combinatorial Scaffold Approach toward Kinase-Directed Heterocycle Libraries," J. Am. Chem. Soc., 124(8): 1594-1596.

(Continued)

*Primary Examiner*—Zachary C Tucker
(74) *Attorney, Agent, or Firm*—Finnegan, Henderson, Farabow, Garrett & Dunner, LLP

(57) ABSTRACT

Certain substituted imidazo[1,2-a]pyrazines and the pharmaceutically acceptable salts thereof, are provided herein. Pharmaceutical compositions containing one or more compound of Formula I, or a pharmaceutically acceptable salt of such compounds, and one or more pharmaceutically acceptable carriers, excipients, or diluents, are also provided herein.

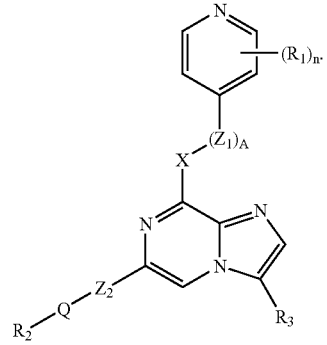

Formula 1

Methods of treating patients suffering from certain diseases and disorders responsive to EphB4 kinase modulation, which comprise administering to such patients an amount of a compound of Formula I effective to reduce signs or symptoms of the disease or disorder are disclosed.

Methods of treatment include administering a compound of Formula I as a single active agent or administering a compound of Formula I in combination with one or more other therapeutic agents.

A method for determining the presence or absence of an angiogenic kinase in a sample comprising contacting the sample with a compound of Formula I under conditions that permit detection of activity of the angiogenic kinase, detecting a level of the activity of the angiogenic kinase, and therefrom determining the presence or absence of the angiogenic kinase in the sample.

42 Claims, No Drawings

FOREIGN PATENT DOCUMENTS

| | | |
|---|---|---|
| WO | WO96/04298 | 2/1996 |
| WO | WO96/34866 | 11/1996 |
| WO | WO99/28322 | 6/1999 |
| WO | WO 01/27119 | 4/2001 |
| WO | WO 02/10170 | 2/2002 |
| WO | WO 02/30428 | 4/2002 |
| WO | WO 02/060492 | 8/2002 |
| WO | WO 02/066481 | 8/2002 |
| WO | WO 02/076985 | 10/2002 |
| WO | WO 03/070732 | 8/2003 |
| WO | WO 03/089434 | 10/2003 |
| WO | WO 2004/022562 | 3/2004 |
| WO | WO 2004/026310 | 4/2004 |
| WO | WO 2004/026877 | 4/2004 |
| WO | WO 2004/072080 | 8/2004 |
| WO | WO 2004/072081 | 8/2004 |
| WO | WO 2005/019220 | 3/2005 |

OTHER PUBLICATIONS

Hanks (Apr. 1, 1994) "Hanks Classification: Protein Kinase Classification, provided by Steven K. Hanks," pp. 1-4, from http://pkr.sdsc.edu/html/pk_classification/pk_catalytic/pk_hanks_class.html.

Jeffrey et al. (1998) "Phosphodiesterase III and V Inhibitors on Pulmonary Artery from Pulmonary Hypertensive Rats: Differences Between Early and Established Pulmonary Hypertension," J. Cardiovascular Pharmacology, 32:213-219.

Lumma Jr. et al. (1983) "Piperazinylimidazo[1,2-a]pyrazines with Selective Affinity for in Vitro alpha-Adrenergic Receptor Subtypes," J. Med. Chem., 26:357-363.

"Protein Kinases in Disease," references produced from a Sep. 24, 1997, search of the On-line Meddelian Inheritance in Man (OMIM) database, pp. 1-11, from http://bioinformatics.weizmann.ac.il/Kinases/pkr/pk_medicine.html.

Stenberg et al. (2000) "KinMutBase, a database of human disease-causing protein kinase mutations," Nucleic Acids Research, 28(1):369-371.

Vitse et al. (1999) "New Imidazo[1,2-a]pyrazine Derivatives with Brochodilatory and Cyclic Nucleotide Phosphodiesterase Inhibitory Activities," Bioorganic & Medicinal Chemistry, 7: 1059-1065.

Restriction Requirement dated Oct. 20, 2004, for U.S. Appl. No. 10/419,682, filed Apr. 21, 2003.

International Search Report dated Oct. 22, 2003, for Application No. PCT/US03/12222, International filing date Apr. 21, 2003.

Written Opinion dated Dec. 5, 2003, for Application No. PCT/US03/12222, International filing date Apr. 21, 2003.

Second Written Opinion dated Apr. 13, 2004, for Application No. PCT/US03/12222, International filing date Apr. 21, 2003.

International Preliminary Examination Report dated Aug. 3, 2004, for Application No. PCT/US03/12222, International filing date Apr. 21, 2003.

International Search Report dated Feb. 9, 2004, for Application No. PCT/US03/28329, International filing date Sep. 9, 2003.

Written Opinion dated Jul. 6, 2004, for Application No. PCT/US03/28329, International filing date Sep. 9, 2003.

International Preliminary Examination Report dated Oct. 27, 2004, for Application No. PCT/US03/28329, International filing date Sep. 9, 2003.

International Search Report and Written Opinion dated Jul. 7, 2004, for Application No. PCT/US2004/003922, International filing date Feb. 10, 2004.

International Search Report and Written Opinion dated Jul. 7, 2004, for Application No. PCT/US2004/003923, International filing date Feb. 10, 2004.

International Search Report and Written Opinion dated Dec. 8, 2004, for Application No. PCT/US2004/021150, International filing date Jun. 30, 2004.

International Search Report and Written Opinion dated Feb. 1, 2005, for Application No. PCT/US2004/025884, International filing date Aug. 11, 2004.

Office Action dated Apr. 3, 2006, for U.S. Appl. No. 10/776,002, filed Feb. 10, 2004.

Office Action dated May 24, 2006, for U.S. Appl. No. 10/776,631, filed Feb. 10, 2004.

Notice of Allowance dated Aug. 11, 2006, for U.S. Appl. No. 10/776,002, filed Feb. 10, 2004.

Notice of Allowance dated Sep. 7, 2006, for U.S. Appl. No. 10/776,631, filed Feb. 10, 2004.

Office Action dated Sep. 26, 2006, for U.S. Appl. No. 10/658, 121, filed Sep. 9, 2003.

* cited by examiner

CERTAIN SUBSTITUTED IMIDAZO[1,2-A]PYRAZINES, AS MODULATORS OF KINASE ACTIVITY

This application claims priority to U.S. provisional application 60/494,179 filed Aug. 11, 2003; U.S. provisional application 60/540,938 filed Jan. 30, 2004; and U.S. provisional application 60/589,738, filed Jul. 21, 2004.

Provided herein are certain imidazo[1,2-a]pyrazinylamines and related compounds, compositions comprising such compounds, and methods of their use.

Protein kinases, the largest family of human enzymes, encompass well over 500 proteins. Kinases play critical roles in signaling pathways controlling fundamental cellular processes such as proliferation, differentiation, and death (apoptosis). Abnormal kinase activity has been implicated in a wide range of diseases, including multiple cancers and autoimmune and inflammatory diseases. The multifaceted role of kinases in key cell signaling pathways provides a significant opportunity to identify novel drugs targeting kinases and signaling pathways. Diseases mediated by receptor kinase activity include, but are not limited to, diseases characterized in part by abnormal levels of cell proliferation (i.e. tumor growth), programmed cell death (apoptosis), cell migration and invasion, and angiogenesis associated with tumor growth.

Kinases play a key role in angiogenesis. Angiogenesis, the formation of new blood vessels from preexisting ones, plays a significant role in many pathological settings, including cancer, chronic inflammation, diabetic retinopathy, psoriasis, rheumatoid arthritis, and macular degeneration. Anti-angiogenic therapy represents a potentially important approach for the treatment of solid tumors and other diseases associated with dysregulated vascularization.

Angiogenesis can be regulated by multiple cell-signaling pathways, including pathways controlled by cellular kinases. Blocking angiogenesis, through the modulation of cell kinases, therefore, can represent an effective approach to the treatment of diseases such as cancer.

The process of angiogenesis is complex, requiring the concerted actions of multiple angiogenic mediators as well as the participation of different cell types. Key angiogenesis mediators, including, VEGF, FGF, and angiopoietin 1 and 2 (Ang1 and Ang2) that bind to their cognate receptors (VEG-FRs, FGFRs and Tie1 and Tie2, respectively) expressed on endothelial cells, as well as platelet-derived growth factor (PDGF) that binds to its receptor (PDGFRα) expressed on pericytes and smooth muscle cells have been identified. Recent studies indicate that several members of the ephrin family and their receptor Eph family are regulators of angiogenesis.

Many of the cellular processes regulated by kinases are further regulated by Hsp90. Hsp90 is a molecular chaperone, a class of proteins that regulates protein folding in cells. Hsp90 is an important cell cycle regulatory protein, implicated in the correct folding of multiple proteins, including a number of tyrosine and threonine kinases. It also can ensure the correct folding and activity of numerous kinases involved in cell proliferation and differentiation, many of which also play roles in oncogenesis.

Hsp90 can also function as part of a multi-component complex interacting with many other co-chaperone proteins. While Hsp90 forms a multi-component complex to some extent in normal cells, nearly all Hsp90 present in cultured tumor cells has been shown to be part of a multi-component complex. A number of known oncogenic proteins that are Hsp90 substrate proteins, depend on the chaperone activity of the Hsp90 complex for correct folding. Thus, in tumor cells Hsp90 often functions as a supplier of oncogenic proteins.

Because of its roles in cell cycle control, cell growth, and oncogenesis the Hsp90 complex is an important target for anti-cancer therapeutics. The ability of certain Hsp90 complex inhibitors to cause this protein complex to selectively target its substrate proteins for degradation makes the Hsp90 complex an especially desirable anti-cancer target. Hsp90 is also a potential drug target for autoimmune and degenerative disease because of its role in modulating the cellular stress response.

Agents capable of modulating angiogenic kinases as well as agents capable of modulating an activity of an Hsp90 complex are highly desirable for the treatment of a variety of diseases and disorders, including cancer and diseases and disorders characterized by a change in angiogenesis. The present invention fulfills this need, and provides further related advantages.

Modulators of kinase activity which may generally be described as imidazo[1,2-a]pyrazinylamines are provided herein. Modulators of Hsp90 complex activity which may generally be described as imidazo[1,2-a]pyrazinylamines also are provided herein. Certain compounds provided herein are inhibitors of angiogenic and oncogenic kinases.

In certain embodiments, the invention provides compounds of Formula I

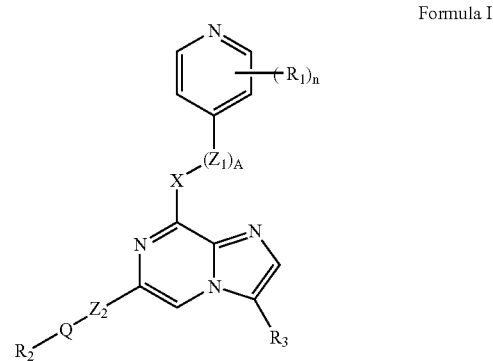

Formula I wherein:

n is 0, 1, 2, or 3;

$R_1$ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl)amino($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl;

$R_3$ is chosen from hydrogen, optionally substituted $C_1$-$C_6$ alkyl, such as optionally substituted $C_3$-$C_6$cycloalkyl, optionally substituted $C_7$cycloalkyl, optionally substituted (heterocycloalkyl)$C_0$-$C_4$alkyl, and optionally substituted (heteroaryl)$C_0$-$C_4$alkyl;

A is 1, 2, 3, or 4;

$Z_1$ is —$CR_4R_5$— wherein each $R_4$ and $R_5$ is independently chosen from hydrogen, $C_1$-$C_6$ alkyl, and halo;

Z₂ is a divalent linking group chosen from para-phenylene, meta-phenylene, ortho-phenylene, and naphthylene, said divalent linking group being substituted with one group R₂—Q—, where Q is

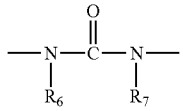

wherein R₆ and R₇ are each independently chosen from hydrogen, $C_1$-$C_6$ alkyl, optionally substituted phenyl, and optionally substituted heteroaryl;

X is O, S or —CH₂—; and

R₂ is chosen from optionally substituted $C_1$-$C_7$alkyl, such as optionally substituted $C_3$-$C_7$cycloalkyl, optionally substituted ($C_3$-$C_7$cycloalkyl)$C_1$-$C_7$ alkyl, optionally substituted heterocycloalkyl, optionally substituted (heterocycloalkyl)$C_1$-$C_2$ alkyl, optionally substituted ($C_1$-$C_6$alkoxy)$C_0$-$C_6$alkyl, optionally substituted ($C_1$-$C_6$alkoxy)$C_1$-$C_6$alkoxy, optionally substituted phenyl, and optionally substituted heteroaryl.

In certain embodiments, the invention provides compounds of Formula I

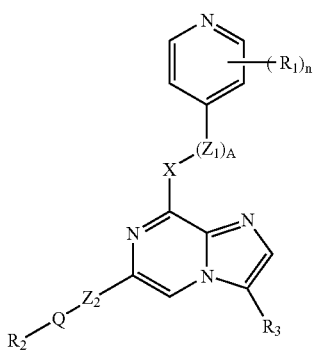

Formula I wherein:

n is 0, 1, 2, or 3;

R₁ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl)amino($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)R₁₃ wherein R₁₃ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl;

R₃ is chosen from hydrogen, optionally substituted $C_1$-$C_6$ alkyl, such as optionally substituted $C_3$-$C_6$cycloalkyl, optionally substituted $C_7$cycloalkyl, optionally substituted (heterocycloalkyl)$C_0$-$C_4$alkyl, and optionally substituted (heteroaryl)$C_0$-$C_4$alkyl;

A is 1, 2, 3, or 4;

Z₁ is —CR₄R₅— wherein each R₄ and R₅ is independently chosen from hydrogen, $C_1$-$C_6$ alkyl, and halo;

Z₂ is a divalent linking group chosen from para-phenylene, meta-phenylene, ortho-phenylene, and naphthylene, said divalent linking group being substituted with one group R₂—Q—, where Q is

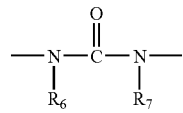

wherein R₆ and R₇ are each independently chosen from hydrogen, $C_1$-$C_6$ alkyl, optionally substituted phenyl, and optionally substituted heteroaryl;

X is NR;

R is chosen from hydrogen, $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, $C_2$-$C_6$ alkynyl, optionally substituted phenyl and optionally substituted heteroaryl; and R₂ is selected from substituted $C_1$-$C_7$alkyl, such as substituted $C_3$-$C_7$cycloalkyl, substituted g($C_3$-$C_7$cycloalkyl)$C_1$-$C_7$ alkyl, substituted heterocycloalkyl, (heterocycloalkyl)$C_1$-$C_2$ alkyl, substituted ($C_1$-$C_6$alkoxy)$C_0$-$C_6$alkyl, substituted ($C_1$-$C_6$alkoxy)$C_1$-$C_6$alkoxy, substituted phenyl, and substituted heteroaryl, wherein said substituted phenyl and substituted heteroaryl are each substituted with one or more substituents chosen from hydroxy, —CHO, —COOH, —CONH₂, and —CONHOH, optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, (mono- and di-$C_1$-$C_6$alkylamino)$C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-$C_6$alkyl, optionally substituted ($C_1$-$C_6$alkoxy)($C_1$-$C_6$alkoxy)$C_1$-$C_6$alkoxy, optionally substituted heterocycloalkyl, optionally substituted aryl, optionally substituted heteroaryl, optionally substituted —$C_1$-$C_6$alkyl(C=O)OR₈, optionally substituted —$C_0$-$C_6$alkyl(C=O)NR₈R₉, optionally substituted—$C_1$-$C_6$alkylNR₈(SO₂)R₉, optionally substituted —$C_0$-$C_6$alkylNR₈(C=O)R₉, optionally substituted —$C_0$-$C_6$alkyl(SO₂)R₈, optionally substituted —$C_0$-$C_6$alkylNR₈(C=O)NR₉R₁₀ where R₈, R₉, and R₁₀ are independently hydrogen, hydroxy, $C_1$-$C_6$alkyl, $C_1$-$C_6$alkoxy, $C_3$-$C_7$cycloalkyl, and heterocycloalkyl, and -L-G, where L is chosen from optionally substituted $C_1$-$C_2$alkyl, optionally substituted $C_0$-$C_2$alkoxy, —(C=O)—, and optionally substituted —($C_1$-$C_2$alkyl)(C=O)—, and G is chosen from optionally substituted heterocycloalkyl, optionally substituted $C_3$-$C_7$cycloalkyl, optionally substituted aryl, and optionally substituted heteroaryl, except that -L-G is not —O-phenyl; and wherein said substituted phenyl and substituted heteroaryl, are each further optionally substituted with one or more substituents chosen from hydroxy, nitro, cyano, amino, sulfonamido, halo, $C_1$-$C_6$ alkyl, such as $C_3$-$C_7$cycloalkyl, ($C_1$-$C_6$ alkoxy)$C_0$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)$R_{13}$, wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, and heteroaryl.

In certain embodiments, the invention includes compounds of Formula I which exhibit an $IC_{50}$ of 1 micromolar or less, 500 nanomolar or less, or 100 nanomolar or less, in standard biochemical assay for $EphB_4$ kinase activity, such as a fluorescence resonance energy transfer (FRET) assay. In certain embodiments, the invention includes compounds of Formula I which exhibit an $IC_{50}$ of 500 nanomolar or less in a standard in vitro assay of PDGF-Rα kinase activity. In certain embodiments, the invention includes compounds of Formula I which exhibit an $IC_{50}$ of 500 nanomolar or less, or 100 nanomolar or less, in a standard in vitro assay of c-Kit activity. In certain embodiments, the invention includes compounds of Formula I which exhibit an $IC_{50}$ of 1 micromolar or less, or 100 nanomolar or less, in a standard in vitro assay of VEGFR-2 activity. In certain embodiments, the invention includes compound of Formula I which exhibits an $IC_{50}$ of 1 micromolar or less, or 500 nanomolar or less, in a standard in vitro assay of Tie-2 activity.

Pharmaceutical compositions comprising one or more compounds of Formula I together with at least one pharmaceutically acceptable carrier or excipient are also provided.

Packaged pharmaceutical compositions are provided which comprise a pharmaceutical composition comprising one or more compounds of Formula I together with at least one pharmaceutically acceptable carrier or excipient in a container and optionally include instructions for using the pharmaceutical composition to treat a mammal suffering from a disease or disorder responsive to kinase modulation. For example, the patient is a human patient, however methods of treating non-human patients, such as non-human animals, preferably mammals, are included herein.

Methods of treating a patient having a disease or disorder responsive to kinase activity modulation and, in certain embodiments, a disease or disorder responsive to modulation of EphB4 are provided herein. In some embodiments, the disease or disorder responsive to kinase activity modulation is chosen from cancer and diseases characterized by a change in angiogenesis. In some embodiments, the disease characterized by a change in angiogenesis is chosen from cancerous tumor, macular degeneration, and diabetic retinopathy.

Methods of modulating $EphB_4$ kinase activity, methods of modulating VEGF-R2 activity, methods of modulating c-Kit activity, methods of modulating Tie-2 activity, methods of modulating PDGF-Rα activity, and methods of modulating at least one of VEGF-R2, $EphB_4$, Tie-2, PDGF-RA, and c-Kit activity are also provided.

Uses of a compound for the manufacture of a medicament for the treatment of a patient having a disease or disorder responsive to activity modulation of at least one of VEGF-R2, $EphB_4$, Tie-2, PDGF-Rα, and c-Kit kinase are also provided. In some embodiments, the disease or disorder responsive to activity modulation is responsive to $EphB_4$ activity modulation. In some embodiments, the disease or disorder responsive to $EphB_4$ activity modulation is chosen from cancer and diseases characterized by a change in angiogenesis. In some embodiments, the disease characterized by a change in angiogenesis is chosen from cancerous tumor, macular degeneration, and diabetic retinopathy.

As used in the present specification, the following words and phrases are generally intended to have the meanings as set forth below, except to the extent that the context in which they are used indicates otherwise. The following abbreviations and terms have the indicated meanings throughout.

As used herein, when any variable occurs more than one time in a chemical formula, its definition on each occurrence is independent of its definition at every other occurrence. In accordance with the usual meaning of "a" and "the" in patents, reference to "a" kinase or "the" kinase is inclusive of one or more kinases. Unless otherwise specified, the terms "compound" and "compounds" include all pharmaceutically acceptable forms of the disclosed structures, including salts, hydrates, solvates, prodrugs, and the like.

Formula I includes all subformulae described herein.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where said event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain, branched chain, and cyclic alkyl groups having the indicated number of carbon atoms. For example $C_1$-$C_6$alkyl encompasses both straight and branched chain alkyl of from 1 to about 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Cycloalkyl, as noted above, is a subset of alkyl. "Cycloalkyl" indicates a saturated hydrocarbon ring group, having the specified number of carbon atoms, usually from 3 to about 7 ring carbon atoms. Examples of cycloalkyl groups include cyclopropyl, cyclobutyl, cyclopentyl, or cyclohexyl as well as bridged or caged saturated ring groups such as norbornane. Alkylene is another subset of alkyl, referring to the same residues as alkyl, but having two points of attachment. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

By "substituted alkyl" is meant an alkyl group having one or more, such as one, two or three, substituents independently chosen from hydroxy, nitro, cyano, amino, halo, $C_1$-$C_6$alkyl, $C_1$-$C_6$alkoxy, ($C_1$-$C_6$alkoxy)$C_1$-$C_6$alkoxy, mono- and di($C_1$-$C_6$ alkyl)amino, amino($C_1$-$C_6$alkyl), $C_1$-$C_3$haloalkyl, $C_1$-$C_3$haloalkoxy, $C_2$-$C_6$ alkenyl, $C_2$-$C_6$ alkynyl, $C_1$-$C_6$ alkylthio, oxo, and —(C=O)$R_{14}$ wherein $R_{14}$ is chosen from $C_1$-$C_6$ alkyl, such as $C_3$-$C_6$cycloalkyl, $C_1$-$C_3$haloalkyl, phenyl, $C_7$cycloalkyl, heterocycloalkyl, and heteroaryl. Each of such substituents may be further optionally substituted with one or more, such as one, two or three, substituents independently chosen from halo, hydroxy, amino, oxo, —COOH, —$CONH_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

By "alkenyl" is meant a straight or branched hydrocarbon chain having the indicated number of carbon atoms and comprising one or more unsaturated carbon-carbon double bonds, which may occur in any stable point along the chain. Examples of such groups include ethenyl and propenyl.

By "substituted alkenyl" is meant an alkenyl group having one or more, such as one, two or three, substituents independently chosen from hydroxy, nitro, cyano, amino, halo, $C_1$-$C_6$alkyl, $C_1$-$C_6$alkoxy, ($C_1$-$C_6$alkoxy)$C_1$-$C_6$alkoxy, mono- and di($C_1$-$C_6$ alkyl)amino, amino($C_1$-$C_6$alkyl), $C_1$-$C_3$haloalkyl, $C_1$-$C_3$haloalkoxy, $C_2$-$C_6$ alkenyl, $C_2$-$C_6$ alkynyl, $C_1$-$C_6$ alkylthio, oxo, and —(C=O)$R_{14}$ wherein $R_{14}$ is chosen from $C_1$-$C_6$ alkyl, such as $C_3$-$C_6$cycloalkyl, $C_1$-$C_3$haloalkyl, phenyl, $C_7$cycloalkyl, heterocycloalkyl, and heteroaryl. Each of such substituents may be further optionally substituted with one or more, such as one, two or three, substituents independently chosen from halo, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

"Alkynyl" encompasses straight and branched hydrocarbon chain having the indicated number of carbon atoms and comprising one or more triple carbon-carbon bonds that may occur in any stable point along the chain, such as ethynyl and propynyl.

By "substituted alkynyl" is meant an alkynyl group having one or more, such as one, two or three, substituents independently chosen from hydroxy, nitro, cyano, amino, halo, $C_1$-$C_6$alkyl, $C_1$-$C_6$alkoxy, ($C_1$-$C_6$alkoxy)$C_1$-$C_6$alkoxy, mono- and di($C_1$-$C_6$ alkyl)amino, amino($C_1$-$C_6$alkyl), $C_1$-$C_3$haloalkyl, $C_1$-$C_3$haloalkoxy, $C_2$-$C_6$ alkenyl, $C_2$-$C_6$ alkynyl, $C_1$-$C_6$ alkylthio, oxo, and —(C=O)$R_{14}$ wherein $R_{14}$ is chosen from $C_1$-$C_6$ alkyl, such as $C_3$-$C_6$cycloalkyl, $C_1$-$C_3$haloalkyl, phenyl, $C_7$cycloalkyl, heterocycloalkyl, and heteroaryl. Each of such substituents may be further optionally substituted with one or more, such as one, two or three, substituents independently chosen from halo, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, 3-methylpentoxy, and the like. In certain embodiments, alkoxy groups herein are $C_1$-$C_4$alkoxy groups.

By "substituted alkoxy" is meant an alkoxy group having one or more, such as one, two or three, substituents independently chosen from hydroxy, nitro, cyano, amino, halo, $C_1$-$C_6$alkyl, $C_1$-$C_6$alkoxy, ($C_1$-$C_6$alkoxy)$C_1$-$C_6$alkoxy, mono- and di($C_1$-$C_6$ alkyl)amino, amino($C_1$-$C_6$alkyl), $C_1$-$C_3$haloalkyl, $C_1$-$C_3$haloalkoxy, $C_2$-$C_6$ alkenyl, $C_2$-$C_6$ alkynyl, $C_1$-$C_6$ alkylthio, oxo, and —(C=O)$R_{14}$ wherein $R_{14}$ is chosen from $C_1$-$C_6$ alkyl, such as $C_3$-$C_6$cycloalkyl, $C_1$-$C_3$haloalkyl, phenyl, $C_7$Cycloalkyl, heterocycloalkyl, and heteroaryl. Each of such substituents may be further optionally substituted with one or more, such as one, two or three, substituents independently chosen from halo, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_{C4}$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

"Mono- and di-alkylcarboxamide" encompass a group of the formula —(C=O)NR$_a$R$_b$ where R$_a$ and R$_b$ are independently chosen from hydrogen and alkyl groups of the indicated number of carbon atoms, provided that R$_a$ and R$_b$ are not both hydrogen.

By "alkylthio" is meant an alkyl group of the indicated number of carbon atoms attached through a sulfur bridge.

"Alkanoyl" indicates an alkyl group as defined above, attached through a keto (—(C=O)—) bridge. The carbon atoms can be in a straight, branched or cyclic configuration, thereof. Alkanoyl groups have the indicated number of carbon atoms, with the carbon of the keto group being included in the numbered carbon atoms. For example a $C_2$alkanoyl group is an acetyl group having the formula $CH_3(C=O)$—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbony group is an alkoxy group having from 1 to about 6 carbon atoms attached through its oxygen to a carbonyl linker.

By "amido" is meant —NH(C=O)R, wherein the R group is chosen from hydrogen and $C_1$-$C_7$alkyl. "Amido" also includes —(C=O)NRR, wherein each R is chosen substituted with one or more, such as one, two or three, substituents independently chosen from halo, $C_1$-$C_6$alkyl, $C_1$-$C_6$haloalkyl, $C_1$-$C_6$haloalkoxy, $C_1$-$C_6$alkoxy, mono- and di($C_1$-$C_6$alkyl)amino.

By "amino" is meant the group —NH$_2$.

"Mono- and di-(alkyl)amino" encompasses secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

"Mono- and di-(alkyl)aminoalkyl" encompasses mono- and di-(alkyl)amino as defined above linked to an alkyl group.

By "amino(alkyl)" is meant an amino group linked to an alkyl group having the indicated number of carbons. Similarly "hydroxyalkyl" is a hydroxy group linked to an alkyl group.

"Aryl" encompasses 5- and 6-membered carbocyclic aromatic rings; bicyclic 9- and 10-membered aromatic ring systems; and tricyclic 12- to 14-membered aromatic ring systems. The aromatic 6- to 14-membered carbocyclic rings include, e.g., benzene, naphthalene, indane, tetralin, and fluorene.

"Substituted aryl", "substituted phenyl", which of course is a subgenus of "substituted aryl," and "substituted heteroaryl" encompass aryl, such as phenyl, and heteroaryl groups, respectively, having one or more, such as one or two, substituents chosen from: hydroxy, —CHO, —COOH, —CONH$_2$, —CONHOH, $C_2$-$C_6$ alkenyl, $C_2$-$C_6$alkynyl, $C_1$-$C_6$hydroxyalkyl, $C_1$-$C_6$hydroxyalkoxy, (mono- and di-$C_1$-$C_6$alkylamino)$C_1$-$C_6$alkoxy, mono- and di($C_1$-$C_6$ alkyl)amino($C_1$-$C_6$alkyl), ($C_1$-$C_6$alkoxy)($C_1$-$C_6$alkylamino)$C_0$-$C_6$alkyl, ($C_1$-$C_6$alkoxy)($C_1$-$C_6$alkoxy)$C_1$-$C_6$alkoxy, heterocycloalkyl, aryl, heteroaryl, —$C_1$-$C_6$alkyl(C=O)OR$_8$, —$C_0$-$C_6$alkyl(C=O)NR$_8$R$_9$, —$C_1$-$C_6$alkylNR$_8$(SO$_2$)R$_9$, —$C_0$-$C_6$alkylNR$_8$(C=O)R$_9$, —$C_0$-$C_6$alkyl(SO$_2$)R$_8$, $C_0$-$C_6$alkylNR$_8$(C=O)NR$_9$R$_{10}$, hydroxy, nitro cyano, amino, sulfonamido, halo, $C_1$-$C_6$ alkyl, such as $C_3$-$C_6$ cycloalkyl, $C_7$ cycloalkyl, $C_1$-$C_6$alkoxy, ($C_1$-$C_6$ alkoxy)$C_0$-$C_6$alkyl, ($C_1$-$C_6$alkoxy)$C_{-C6}$alkoxy, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, —(C=O)$R_{13}$, and -L-G, where L is chosen from $C_1$-$C_2$alkyl, $C_0$-$C_2$alkoxy, —(C=O)—, and -($C_1$-$C_2$alkyl)(C=O)—;

G is chosen from heterocycloalkyl, $C_7$cycloalkyl, aryl, heteroaryl, hydroxy, nitro, cyano, amino, sulfonamido, halo, $C_1$-$C_6$ alkyl, such as $C_3$-$C_6$cycloalkyl, ($C_1$-$C_6$ alkoxy)$C_0$-$C_6$alkyl, ($C_1$-$C_6$alkoxy)$C_1$-$C_6$alkoxy, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_{c6}$alkylester, and —(C=O)$R_{13}$, provided that L-G is not —O-phenyl;

$R_8$, $R_9$, and $R_{10}$ are independently chosen from hydrogen, hydroxy, $C_1$-$C_6$alkyl, such as $C_3$-$C_6$ cycloalkyl, $C_1$-$C_6$alkoxy, $C_7$-$C_{10}$cycloalkyl, and heterocycloalkyl and wherein each of the various alkyl, alkenyl, alkynyl, alkoxyl, cycloalkyl, heterocycloalkyl, aryl, and heteroaryl groups is optionally substituted with one or more, such as one or two, substituents chosen from halo, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_1$-$C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl; and $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl. Each of such substituents may be further optionally substituted with one or more, such as one, two or three, substituents independently chosen from halo, hydroxy, amino, oxo, —COOH, —CONH$_2$, $C_1$-$C_4$alkyl, $C_2$-$C_4$alkenyl, $C_2$-$C_4$alkynyl, $C_1$-$C_4$alkoxy, $C_2$-$C_4$alkanoyl, $C_1$-$C_4$alkylthio, $C_2$haloalkyl, $C_1$-$C_2$haloalkoxy, $C_1$-$C_4$alkoxycarbonyl, mono- and di-$C_1$-$C_4$alkylamino, mono- and di-$C_1$-$C_4$alkylcarboxamide, and phenyl.

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses stable 5- to 7-membered monocyclic and 7- to 10-membered bicyclic heterocyclic rings which contain at least 1 aromatic ring that contains from 1 to 4, or in certain embodiments, from 1 to 3, heteroatoms chosen from N, O, and S, with the remaining ring atoms being carbon. When the total number of S and O atoms in the heteroaryl group exceeds 1, those heteroatoms are not adjacent to one another. In certain embodiments, the total number of S and 0 atoms in the heteroaryl group is not more than 2. In certain embodiments, the total number of S and O atoms in the aromatic heterocycle is not more than 1. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. In the term "heteroarylalkyl," heteroaryl and alkyl are as defined herein, and the point of attachment is on the alkyl group. This term encompasses, but is not limited to, pyridylmethyl, thiophenylmethyl, and (pyrrolyl) 1-ethyl.

By "heterocycloalkyl" is meant a saturated aliphatic ring containing from 1 to 3 heteroatoms independently selected from oxygen, sulfur, or nitrogen with remaining ring atoms being carbon. Heterocycloalkyl groups typically contain from 3 to about 8 ring atoms. Examples of heterocycloalkyl include, but are not limited to, morpholinyl, thiomorpholinyl, piperidinyl, and pyrrolidinyl.

By "sulfonamido" is meant —S(O)$_2$N— in either S-linked (—S(O)$_2$NRR) or N-linked orientation —NS(O)$_2$RR orientation, wherein each R may be independently chosen from hydrogen and $C_1$-$C_7$alkyl wherein alkyl is as defined above, such as 3- to 7-membered cycloalkyl, and heterocycloalyl rings. When R is not hydrogen, each R may be unsubstituted or substituted with one or more, such as one, two or three, substituents independently chosen from, e.g., halo, $C_1$-$C_6$alkyl, $C_1$-$C_6$ haloalkyl, $C_1$-$C_6$ haloalkoxy, $C_1$-$C_6$alkoxy, and mono- and di($C_1$-$C_6$alkyl)amino.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. When aromatic moieties are substituted by an oxo group, the aromatic ring is replaced by the corresponding partially unsaturated ring. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified, substituents are named into the core structure. For example, it is to be understood that when (cycloalkyl)alkyl is listed as a possible substituent, the point of attachment of this substituent to the core structure is in the alkyl portion.

If the compounds of Formula I have asymmetric centers, then Formula I includes all of the optical isomers and mixtures thereof. In addition, compounds with carbon-carbon double bonds may occur in Z- and E-forms, with all isomeric forms of the compounds being included. Those compounds can be, for example, racemates or optically active forms. In those situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. Where a compound of Formula I exists in various tautomeric forms, the invention is not limited to any one of the specific tautomers, and includes all tautomeric forms of the compound.

Representative compounds of the present invention, which are encompassed by Formula I, include, but are not limited to all pharmaceutically acceptable forms. Pharmaceutically acceptable forms of the compounds recited herein include pharmaceutically acceptable salts, hydrates, solvates, crystal forms, polymorphs, chelates, non-covalent complexes, esters, clathrates, prodrugs, and mixtures of such compounds. In certain embodiments, the compounds described herein are in the form of pharmaceutically acceptable salts. Hence, the terms "compound" and "compounds" also encompass pharmaceutically acceptable salts, hydrates, solvates, crystal forms, polymorphs, chelates, non-covalent complexes, esters, clathrates, prodrugs, and mixtures of such compounds.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base compound can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts encompassed by Formula I.

As noted above, prodrugs also fall within the scope of compounds of Formula I, for example acylated prodrugs of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The term "active agent" is used to indicate a compound, including any pharmaceutically form thereof, or natural product, which has biological activity. In certain embodiments, an "active agent" is a compound having pharmaceutical utility. For example an active agent may be an anti-cancer therapeutic.

By "angiogenic kinase" is meant a kinase involved in angiogenesis and includes but is not limited to $EphB_4$, VEGF-R2, and Tie-2.

By "oncogenic kinase" is meant a kinase having a direct role in a cell signaling pathway that leads to cellular transformation. When overexpressed or aberrantly expressed, such kinases may have oncogenic activity. Oncogenic kinases include but are not limited to c-Kit and PDGF-Rα.

"Treatment or treating means any treatment of a disease in a patient, including:
  a) preventing the disease, that is, causing the clinical symptoms of the disease not to develop;
  b) inhibiting the disease;
  c) slowing or arresting the development of clinical symptoms; and/or
  d) relieving the disease, that is, causing the regression of clinical symptoms.

"Diseases or disorders responsive to kinase modulation" refer to pathologic conditions that depend, at least in part, on the activity of one or more protein kinases, for example, angiogenic kinases and/or oncogenic kinases. Kinases either directly or indirectly participate in the signal transduction pathways of a variety of cellular activities including cell proliferation, differentiation, and invasion. Diseases responsive to kinase modulation include but are not limited to tumor growth, angiogenesis supporting solid tumor growth, and diseases characterized by excessive local vascularization such as diabetic retinopathy, macular degeneration, and inflammation.

"Change in angiogenesis" refers to a change in the vascular network or quality of vasculature. Change in angiogenesis may be measured by many parameters and, for instance, may be assessed by delayed appearance of neovascular structures, slowed development of neovascular structures, decreased occurrence of neovascular structures, changes in vascular permeability, changes in blood flow, slowed or decreased severity of angiogenesis-dependent disease effects, arrested angiogenic growth, or regression of previous angiogenic growth.

"Diseases or disorders responsive to Hsp90 complex modulation" refer to pathologic conditions that depend, in part, on the activity of Hsp90 complex. The Hsp90 complex or its substrate proteins have been implicated in a number of cancerous conditions. Diseases responsive to Hsp90 complex modulation include but are not limited to heart disease, stroke, and neurodegenerative diseases including multiple sclerosis, Alzheimer's dementia, short term memory loss, and ischemic optic neuropathy.

"Patient" refers to an animal, such as a mammal, for example a human, that has been or will be the object of treatment, observation or experiment. The methods of the invention can be useful in both human therapy and veterinary applications. In some embodiments, the patient is a mammal, and in some embodiments the patient is human.

The term "therapeutically effective amount" of a compound of this invention means an amount effective, when administered to a human or non-human patient, to provide a therapeutic benefit such as an amelioration of symptoms, e.g., an amount effective to at least decrease the symptoms of a disease or disorder responsive to kinase modulation, including those diseases and disorders response to modulation of ephrin receptors, such as ephrin B receptors, and including EphB4, and, in certain embodiments, an amount sufficient to reduce cancer symptoms, decrease the number of detectable cancerous cells in an organism, detectably slow or stop the growth of a cancerous tumor, or, in certain embodiments, to shrink a cancerous tumor. In certain circumstances a patient suffering from cancer may not present symptoms of being affected. Thus a therapeutically effective amount of a compound is also an amount sufficient to prevent a significant increase or significantly reduce the detectable level of cancerous cells or cancer markers in the patient's blood, serum, or tissues. A significant increase or reduction in the detectable level of cancerous cells or cancer markers is any detectable change that is statistically significant in a standard parametric test of statistical significance such as Student's T-test, where $p<0.05$.

Within certain embodiments, the invention provides compounds, including, of course, pharmaceutically acceptable salts, of Formula I, as well as compositions comprising such compounds; methods of using such compounds; and uses of such compounds for the manufacture of medicaments,

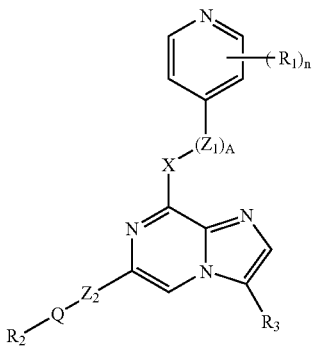

Formula I wherein:
n is 0, 1, 2, or 3;
R₁ is independently chosen from hydroxy, nitro, cyano, amino, amido, sulfonamido, halo, —CHO, —COOH, C₁-C₆alkyl, such as C₃-C₆cycloalkyl, C₂-C₆ alkenyl, C₂-C₆ alkynyl, C₁-C₆ alkoxy, C₇cycloalkyl, mono- and di(C₁-C₆ alkyl)amino, mono- and di(C₁-C₆ alkyl)amino (C₁-C₆alkyl), C₁-C₆haloalkyl, C₁-C₆haloalkoxy, (C₁-C₆alkoxy)C₁-C₆alkoxy, amino(C₁-C₆alkyl), C₁-C₆alkylthio, oxo, heteroaryl, and —(C=O)R₁₃ wherein R₁₃ is chosen from C₁-C₆ alkyl, such as C₃-C₆cycloalkyl, C₇cycloalkyl, C₂-C₆ alkanoyl, C₁-C₆alkoxycarbonyl, heterocycloalkyl, phenyl, and heteroaryl;
R₃ is chosen from hydrogen, optionally substituted C₁-C₆ alkyl, such as optionally substituted C₃-C₆cycloalkyl, optionally substituted C₇cycloalkyl, optionally substituted (heterocycloalkyl)C₀-C₄alkyl, and optionally substituted (heteroaryl)C₀-C₄alkyl;
A is 1, 2, 3, or 4;
Z₁ is —CR₄R₅— wherein each R₄ and R₅ is independently chosen from hydrogen, C₁-C₆ alkyl, and halo;
Z₂ is a divalent linking group chosen from para-phenylene, meta-phenylene, ortho-phenylene, and naphthylene, said divalent linking group being substituted with one group R₂—Q—, where
Q is

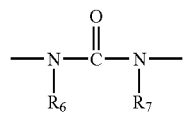

wherein R₆ and R₇ are independently chosen from hydrogen; C₁-C₆ alkyl; optionally substituted phenyl, and optionally substituted heteroaryl;
X is O, S or —CH₂—; and
R₂ is chosen from optionally substituted C₁-C₇alkyl, such as optionally substituted C₃-C₇cycloalkyl, optionally substituted (C₃-C₇cycloalkyl)C₁-C₇ alkyl, optionally substituted heterocycloalkyl, optionally substituted (heterocycloalkyl)C₁-C₂ alkyl, optionally substituted (C₁-C₆alkoxy)C₀-C₆alkyl, optionally substituted (C₁-C₆alkoxy)C₁-C₆alkoxy, optionally substituted phenyl, and optionally substituted heteroaryl.

Within certain embodiments, the invention provides compounds, including, of course, pharmaceutically acceptable salts, of Formula I, as well as compositions comprising such compounds; methods of using such compounds; and uses of such compounds for the manufacture of medicaments,

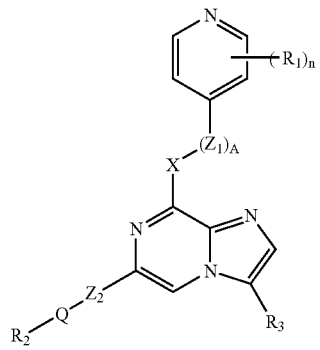

Formula I wherein:
n is 0, 1, 2, or 3;
R₁ is independently chosen from hydroxy, nitro, cyano, amino, amido, sulfonamido, halo, —CHO, —COOH, C₁-C₆alkyl, such as C₃-C₆cycloalkyl, C₂-C₆ alkenyl, C₂-C₆ alkynyl, C₁-C₆ alkoxy, C₇cycloalkyl, mono- and di(C₁-C₆ alkyl)amino, mono- and di(C₁-C₆ alkyl)amino (C₁-C₆alkyl), C₁-C₆haloalkyl, C₁-C₆haloalkoxy, (C₁-C₆alkoxy)C₁-C₆alkoxy, amino(C₁-C₆alkyl), C₁-C₆alkylthio, oxo, heteroaryl, and —(C=O)R₁₃ wherein R₁₃ is chosen from C₁-C₆ alkyl, such as C₃-C₆cycloalkyl, C₇cycloalkyl, C₂-C₆ alkanoyl, C₁-C₆alkoxycarbonyl, heterocycloalkyl, phenyl, and heteroaryl;
R₃ is chosen from hydrogen, optionally substituted C₁-C₆ alkyl, such as optionally substituted C₃-C₆cycloalkyl, optionally substituted C₇cycloalkyl, optionally substituted (heterocycloalkyl)C₀-C₄alkyl, and optionally substituted (heteroaryl)C₀-C₄alkyl;
A is 1, 2, 3, or 4;
Z₁ is —CR₄R₅— wherein R₄ and R₅ are independently chosen from hydrogen, C₁-C₆ alkyl, and halo;
Z₂ is a divalent linking group chosen from para-phenylene, meta-phenylene, ortho-phenylene, and naphthylene, said divalent linking group being substituted with one group R₂—Q—, where
Q is

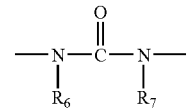

wherein R₆ and R₇ are each independently chosen from hydrogen; C₁-C₆ alkyl; optionally substituted phenyl, and optionally substituted heteroaryl;
X is NR;
R is chosen from hydrogen; C₁-C₆ alkyl, such as C₃-C₆cycloalkyl, C₇cycloalkyl, amino(C₁-C₆ alkyl), C₁-C₃haloalkyl, C₂-C₆alkenyl, or C₂-C₆ alkynyl, optionally substituted phenyl, and optionally substituted heteroaryl; and
R₂ is chosen from optionally substituted C₁-C₇alkyl, such as optionally substituted C₃-C₇cycloalkyl, optionally substituted (C₃-C₇cycloalkyl)C₁-C₇ alkyl, optionally substituted heterocycloalkyl, optionally substituted (heterocycloalkyl)C₁-C₂ alkyl, optionally substituted (C₁-C₆alkoxy)C₀-C₆alkyl, optionally substituted (C₁-C₆alkoxy)C₁-C₆alkoxy, substituted phenyl, and substituted heteroaryl.

Within certain embodiments, the invention provides compounds, including, of course, pharmaceutically acceptable salts, of Formula I, as well as compositions comprising such compounds; methods of using such compounds; and uses of such compounds for the manufacture of medicaments,

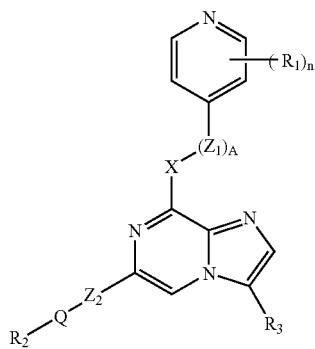

Formula I wherein:

n is 0, 1, 2, or 3;

R₁ is independently chosen from hydroxy, nitro, cyano, amino, amido, sulfonamido, halo, —CHO, —COOH, C₁-C₆alkyl, such as C₃-C₆cycloalkyl, C₂-C₆ alkenyl, C₂-C₆ alkynyl, C₁-C₆ alkoxy, C₇cycloalkyl, mono- and di(C₁-C₆ alkyl)amino, mono- and di(C₁-C₆ alkyl)amino(C₁-C₆alkyl), C₁-C₆haloalkyl, C₁-C₆haloalkoxy, (C₁-C₆alkoxy)C₁-C₆alkoxy, amino(C₁-C₆alkyl), C₁-C₆alkylthio, oxo, heteroaryl, and —(C=O)R₁₃ wherein R₁₃ is chosen from C₁-C₆ alkyl, such as C₃-C₆cycloalkyl, C₇cycloalkyl, C₂-C₆ alkanoyl, C₁-C₆alkoxycarbonyl, heterocycloalkyl, phenyl, and heteroaryl;

R₃ is chosen from hydrogen, optionally substituted C₁-C₆ alkyl, such as optionally substituted C₃-C₆cycloalkyl, optionally substituted C₇cycloalkyl, optionally substituted (heterocycloalkyl)C₀-C₄alkyl, and optionally substituted (heteroaryl)C₀-C₄alkyl;

A is 1, 2, 3, or 4;

Z₁ is —CR₄R₅— wherein R₄ and R₅ are independently chosen from hydrogen, C₁-C₆ alkyl, and halo;

Z₂ is a divalent linking group chosen from para-phenylene, meta-phenylene, ortho-phenylene, and naphthylene, said divalent linking group being substituted with one group R₂-Q-, where Q is

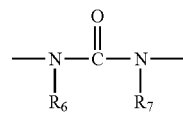

wherein R₆ and R₇ are each independently chosen from hydrogen; C₁-C₆ alkyl; optionally substituted phenyl, and optionally substituted heteroaryl;

X is NR;

R is chosen from hydrogen. C₁-C₆ alkyl, such as C₃-C₆cycloalkyl, C₇cycloalkyl, amino(C₁-C₆ alkyl), C₁-C₃haloalkyl, C₂-C₆alkenyl, or C₂-C₆ alkynyl, optionally substituted phenyl, and optionally substituted heteroaryl; and R₂ is selected from substituted C₁-C₇alkyl, such as substituted C₃-C₇cycloalkyl, substituted (C₃-C₇cycloalkyl)C₁-C₇ alkyl, substituted heterocycloalkyl, (heterocycloalkyl) C₁-C₂ alkyl, substituted (C₁-C₆alkoxy)C₀-C₆alkyl, substituted (C₁-C₆alkoxy)C₁-C₆alkoxy, substituted phenyl, and substituted heteroaryl, wherein said substituted phenyl and substituted heteroaryl are each substituted with one or more substituents chosen from hydroxy, —CHO, —COOH, —CONH₂, and —CONHOH, optionally substituted C₂-C₆ alkenyl, optionally substituted C₂-C₆alkynyl, optionally substituted C₁-C₆hydroxyalkyl, optionally substituted C₁-C₆hydroxyalkoxy, (mono- and di-C₁-C₆alkylamino) C₁-C₆alkoxy, optionally substituted mono- and di(C₁-C₆ alkyl)amino(C₁-C₆alkyl), optionally substituted (C₁-C₆alkoxy)(C₁-C₆alkylamino)C₀-C₆alkyl, optionally substituted (C₁-C₆alkoxy)(C₁-C₆alkoxy)C₁-C₆alkoxy, optionally substituted heterocycloalkyl, optionally substituted aryl, optionally substituted heteroaryl, optionally substituted —C₁-C₆alkyl(C=O)OR₈, optionally substituted —C₀-C₆alkyl(C=O)NR₈R₉, optionally substituted —C₁-C₆alkylNR₈(SO₂)R₉, optionally substituted —C₀-C₆alkylNR₈(C=O)R₉, optionally substituted —C₀-C₆alkyl(SO₂)R₈, optionally substituted —C₀-C₆alkylNR₈(C=O)NR₉R₁₀ where R₈, R₉, and R₁₀ are independently chosen from hydrogen, hydroxy, C₁-C₆alkyl, C₁-C₆alkoxy, C₃-C₇cycloalkyl, and heterocycloalkyl, and -L-G, where L is chosen from optionally substituted C₁-C₂alkyl, optionally substituted C₀-C₂alkoxy, —(C=O)—, and optionally substituted —(C₁-C₂alkyl) (C=O)—, and G is chosen from optionally substituted heterocycloalkyl, optionally substituted C₃-C₇cycloalkyl, optionally substituted aryl, and optionally substituted heteroaryl, except that -L-G is not —O-phenyl; and wherein said substituted phenyl and substituted heteroaryl are each further optionally substituted with one or more substituents chosen from hydroxy, nitro, cyano, amino, sulfonamido, halo, C₁-C₆ alkyl, such as C₃-C₇cycloalkyl, (C₁-C₆ alkoxy)C₀-C₆alkyl, (C₁-C₆alkoxy)C₁-C₆alkoxy, C₇cycloalkyl, aminoC₁-C₆alkyl, mono- and di(C₁-C₆ alkyl)amino, C₁-C₆haloalkyl, C₁-C₆haloalkoxy, C₂-C₆alkenyl, C₂-C₆alkynyl, C₁-C₆alkylthio, oxo, C₁-C₆alkylester, phenoxy, and —(C=O)R₁₃, wherein R₁₃ is C₁-C₆ alkyl, such as C₃-C₆cycloalkyl, C₇cycloalkyl, C₂-C₆ alkanoyl, C₁-C₆alkoxycarbonyl, heterocycloalkyl, and heteroaryl.

Within certain embodiments, the invention provides uses of compounds, including, of course, pharmaceutically acceptable salts, of Formula I for the manufacture of medicaments and methods of using compounds of Formula I:

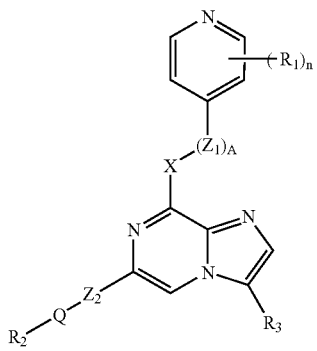

wherein:

n is 0, 1, 2, or 3;

$R_1$ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl)amino ($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl;

$R_3$ is chosen from hydrogen, optionally substituted $C_1$-$C_6$ alkyl, such as optionally substituted $C_3$-$C_6$cycloalkyl, optionally substituted $C_7$cycloalkyl, optionally substituted (heterocycloalkyl)$C_0$-$C_4$alkyl, and optionally substituted (heteroaryl)$C_0$-$C_4$alkyl;

A is 1, 2, 3 or 4;

$Z_1$ is —$CR_4R_5$— wherein $R_4$ and $R_5$ are independently chosen from hydrogen, $C_1$-$C_6$ alkyl, and halo;

$Z_2$ is a divalent linking group chosen from para-phenylene, meta-phenylene, ortho-phenylene, and naphthylene, said divalent linking group being substituted with one group $R_2$—Q—, where Q is

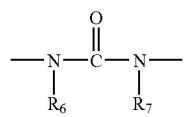

wherein $R_6$ and $R_7$ are each independently chosen from hydrogen; $C_1$-$C_6$ alkyl; optionally substituted phenyl, and optionally substituted heteroaryl;

X is NR;

R is chosen from hydrogen, $C_1$-$C_6$ alkyl, such as C3-$C_6$cycloalkyl, $C_7$cycloalkyl, amino($C_1$-$C_6$ alkyl), $C_1$-$C_3$haloalkyl, $C_2$-$C_6$alkenyl, $C_2$-$C_6$ alkynyl, optionally substituted phenyl and optionally substituted heteroaryl; and $R_2$ is chosen from optionally substituted $C_1$-$C_7$alkyl, such as optionally substituted $C_3$-$C_7$cycloalkyl, optionally substituted ($C_3$-$C_7$cycloalkyl)$C_1$-$C_7$ alkyl, optionally substituted heterocycloalkyl, optionally substituted (heterocycloalkyl)$C_1$-$C_2$ alkyl, optionally substituted ($C_1$-$C_6$alkoxy)$C_0$-$C_6$alkyl, optionally substituted ($C_1$-$C_6$alkoxy)$C_1$-$C_6$alkoxy, optionally substituted phenyl, and optionally substituted heteroaryl.

Within certain embodiments, the invention provides uses of compounds, including of course, pharmaceutically acceptable salts, of Formula I for the manufacture of medicaments and methods of using compounds of Formula I:

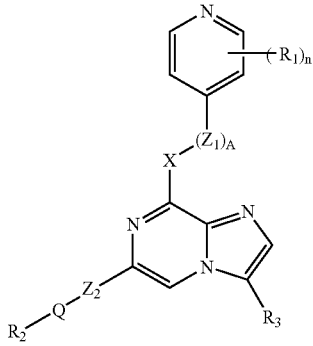

wherein:

n is 0, 1, 2, or 3;

$R_1$ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl)amino ($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl;

$R_3$ is chosen from hydrogen, optionally substituted $C_1$-$C_6$ alkyl, such as optionally substituted $C_3$-$C_6$cycloalkyl, optionally substituted $C_7$cycloalkyl, optionally substituted (heterocycloalkyl)$C_0$-$C_4$alkyl, and optionally substituted (heteroaryl)$C_0$-$C_4$alkyl;

A is 1, 2, 3 or 4;

$Z_1$ is —$CR_4R_5$— wherein $R_4$ and $R_5$ are independently chosen from hydrogen, $C_1$-$C_6$ alkyl, and halo;

$Z_2$ is a divalent linking group chosen from para-phenylene, meta-phenylene, ortho-phenylene, and naphthylene, said divalent linking group being substituted with one group $R_2$—Q—, where Q is

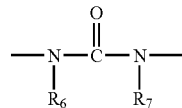

wherein $R_6$ and $R_7$ are each independently chosen from hydrogen; $C_1$-$C_6$ alkyl; optionally substituted phenyl, and optionally substituted heteroaryl;

X is NR;

R is chosen from hydrogen, $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, $C_2$-$C_6$ alkynyl, optionally substituted phenyl and optionally substituted heteroaryl; and $R_2$ is selected from substituted $C_1$-$C_7$alkyl, such as substituted $C_3$-$C_7$cycloalkyl, substituted ($C_3$-$C_7$cycloalkyl)$C_1$-$C_7$ alkyl, substituted heterocycloalkyl, (heterocycloalkyl) $C_1$-$C_2$ alkyl, substituted ($C_1$-$C_6$alkoxy)$C_0$-$C_6$alkyl, substituted ($C_1$-$C_6$alkoxy)$C_1$-$C_6$alkoxy, substituted phenyl, and substituted heteroaryl, wherein said substituted phenyl and substituted heteroaryl, are each substituted with one or more substituents chosen from hydroxy, —CHO, —COOH, —CONH$_2$, and —CONHOH, optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, (mono- and di-$C_1$-$C_6$alkylamino) $C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-$C_6$alkyl, optionally substituted ($C_1$-$C_6$alkoxy)($C_1$-$C_6$alkoxy)$C_1$-$C_6$alkoxy, optionally substituted heterocycloalkyl, optionally substituted aryl, optionally substituted heteroaryl, optionally substituted -$C_1$-$C_6$alkyl(C=O)O$R_8$, optionally substituted —$C_0$-$C_6$alkyl(C=O)N$R_8R_9$, optionally substituted —$C_1$-$C_6$alkylN$R_8$(SO$_2$)$R_9$, optionally substituted —$C_0$-$C_6$alkylN$R_8$(C=O)$R_9$, optionally substituted —$C_0$-$C_6$alkyl(SO$_2$)$R_8$, optionally substituted —$C_0$-$C_6$alkylN$R_8$(C=O)N$R_9R_{10}$ where $R_8$, $R_9$, and $R_{10}$ are independently chosen from hydrogen, hydroxy, $C_1$-$C_6$alkyl, $C_1$-$C_6$alkoxy, $C_3$-$C_7$cycloalkyl, and heterocycloalkyl, -L-G, where L is chosen from optionally substituted $C_1$-$C_2$alkyl, optionally substituted $C_0$-$C_2$alkoxy, —(C=O)—, and optionally substituted —($C_1$-$C_2$alkyl) (C=O)—, and G is chosen from optionally substituted heterocycloalkyl, optionally substituted $C_3$-$C_7$cycloalkyl, optionally substituted aryl, and optionally substituted heteroaryl, except that -L-G is not —O-phenyl; and wherein said substituted phenyl and substituted heteroaryl, are each further optionally substituted with one or more substituents chosen from hydroxy, nitro, cyano, amino, sulfonamido, halo, $C_1$-$C_6$ alkyl, such as $C_3$-$C_7$cycloalkyl, ($C_1$-$C_6$ alkoxy)$C_0$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)$R_{13}$, wherein $R_{13}$ is $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, and heteroaryl.

Referring to compounds of Formula I, in certain embodiments, n is 0, 1, 2, or 3. In certain embodiments, n is 0 and thus, $R_1$ is absent, i.e., the pyridin-4-yl ring is unsubstituted.

In certain embodiments, n is 1 and $R_1$ is chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl) amino($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl.

In certain embodiments, n is 1 and $R_1$ is chosen from hydroxy, nitro, cyano, amino, halo, —CHO, —COOH, $C_1$-$C_6$ alkyl, such as $C_3$-$C_6$cycloalkyl, $C_1$-$C_6$alkoxy, $C_1$-$C_2$haloalkyl, $C_1$-$C_2$haloalkoxy, ($C_1$-$C_6$alkoxy)$C_1$-$C_6$alkoxy, mono- and di-($C_1$-$C_6$ alkyl)amino, amino($C_1$-$C_6$ alkyl), $C_1$-$C_6$ alkylthio, mono- and di-($C_1$-$C_6$ alkyl)amino($C_1$-$C_6$ alkyl), $C_7$ cycloalkyl, $C_2$-$C_6$ alkanoyl, $C_1$-$C_6$alkoxycarbonyl, heterocycloalkyl, amido, and sulfonamido. In certain embodiments, n is 1 and $R_1$ is chosen from hydroxy, cyano, halo, $C_1$-$C_2$alkyl, $C_1$-$C_2$alkoxy, $C_1$-$C_2$haloalkyl, and $C_1$-$C_2$haloalkoxy. In certain embodiments, n is 1 and $R_1$ is chosen from halo, methyl, and methoxy In certain embodiments, n is 2 or 3; and each occurrence of $R_1$ is independently chosen from hydroxy, nitro, cyano, amino, amido, sulfonamido, halo, —CHO, —COOH, —$C_1$-$C_6$alkyl, such as $C_3$-$C_6$cycloalkyl, $C_2$-$C_6$ alkenyl, $C_2$-$C_6$ alkynyl, $C_1$-$C_6$ alkoxy $C_7$cycloalkyl, mono- and di($C_1$-$C_6$ alkyl)amino, mono- and di($C_1$-$C_6$ alkyl)amino($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl.

In certain embodiments, n is 2 or 3 and each occurrence of $R_1$ is independently chosen from hydroxy, nitro, cyano, amino, halo, —CHO, —COOH, $C_1$-$C_6$ alkyl, such as $C_3$-$C_6$cycloalkyl, $C_1$-$C_6$alkoxy, $C_1$-$C_2$haloalkyl, $C_1$-$C_2$haloalkoxy, ($C_1$-$C_6$alkoxy)$C_1$-$C_6$alkoxy, mono- and di-($C_1$-$C_6$ alkyl)amino, amino($C_1$-$C_6$ alkyl), $C_{1-C6}$ alkylthio, mono- and di-($C_1$-$C_6$ alkyl)amino($C_1$-$C_6$ alkyl), $C_7$ cycloalkyl, $C_2$-$C_6$ alkanoyl, $C_1$-$C_6$alkoxycarbonyl, heterocycloalkyl, amido, and sulfonamido. In certain embodiments, n is 2 or 3 and each occurrence of $R_1$ is independently chosen from hydroxy, cyano, halo, $C_1$-$C_2$alkyl, $C_1$-$C_2$alkoxy, $C_1$-$C_2$haloalkyl, and $C_1$-$C_2$haloalkoxy. In certain embodiments, n is 2 or 3 and each occurrence of $R_1$ is independently chosen from halo, methyl, and methoxy. In certain embodiments, n is 2 and each occurrence of $R_1$ is independently chosen from halo, methyl, and methoxy.

In certain embodiments, A is 1, 2, 3, or 4; and each of $R_4$ and $R_5$ is independently chosen from hydrogen, $C_1$-$C_6$alkyl, and halo. In certain embodiments, A is 1, 2, 3, or 4; $Z_1$ is —CR$_4$R$_5$—, and $R_4$ and $R_5$ are both hydrogen.

In certain embodiments, A is 1 or 2. In certain embodiments, A is 1 or 2, $Z_1$ is —CR$_4$R$_5$—, and each of $R_4$ and $R_5$ is independently chosen from hydrogen, $C_1$-$C_6$ alkyl, and halo. In certain embodiments, A is 1, $Z_1$ is —CR$_4$R$_5$—, and each of $R_4$ and $R_5$ is independently chosen from hydrogen, $C_1$-$C_6$alkyl, and halo. In certain embodiments, A is 1; and $R_4$ and $R_5$ are both hydrogen.

In certain embodiments, A is 3 or 4, $Z_1$ is —CR$_4$R$_5$—, and each of $R_4$ and $R_5$ is independently chosen from hydrogen, $C_1$-$C_6$alkyl, and halo. In certain embodiments, when X is NR, A is 3 or 4, $Z_1$ is —CR$_4$R$_5$—, and each of $R_4$ and $R_5$ is independently chosen from hydrogen, $C_1$-$C_6$alkyl, and halo.

In certain embodiments, X is NR and R is chosen from hydrogen, $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, $C_2$-$C_6$ alkynyl, optionally substituted phenyl and optionally substituted heteroaryl. In certain embodiments, R is chosen from hydrogen; $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, and$C_2$-$C_6$ alkynyl. In certain embodiments, R is chosen from hydrogen and $C_1$-$C_4$alkyl. In certain of these embodiments R is hydrogen. In certain other of these embodiments R is amino($C_1$-$C_4$alkyl).

In certain embodiments, X is O, S, or CH$_2$. In certain embodiments, X is O. In certain embodiments, X is S. In certain embodiments, X is CH$_2$.

In certain embodiments, $R_3$ is chosen from hydrogen, optionally substituted $C_1$-$C_6$alkyl, such as optionally substituted $C_3$-$C_6$cycloalkyl, optionally substituted $C_7$cycloalkyl, optionally substituted (heterocycloalkyl)$C_0$-$C_4$alkyl, and optionally substituted (heteroaryl)$C_0$-$C_4$alkyl. In certain embodiments, $R_3$ is chosen from hydrogen and $C_1$-$C_4$alkyl. In certain embodiments, $R_3$ is hydrogen.

In certain embodiments, $Z_2$ is a divalent linking group chosen from para-phenylene, meta-phenylene, ortho-phenylene, and naphthylene, said divalent linking group being substituted with one group $R_2$—Q—. In certain embodiments, $Z_2$ is meta-phenylene linking $R_2$—Q— with the imidazopyrazine ring.

In certain embodiments, Q is

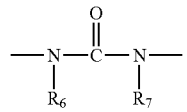

wherein $R_6$ and $R_7$ are each independently chosen from hydrogen, $C_1$-$C_6$ alkyl, phenyl, and heteroaryl wherein the phenyl or heteroaryl is optionally substituted with one, two or three substituents independently chosen from hydroxy, nitro, cyano, amino, halo, —CHO, —COOH, —CONH$_2$, $C_1$-$C_6$alkyl, such as $C_3$-$C_6$cycloalkyl, $C_2$-$C_6$alkenyl, $C_2$-$C_6$ alkynyl, $C_1$-$C_6$alkoxy, $C_1$-$C_6$haloalkyl, $C_1$-$C_6$ haloalkoxy, ($C_1$-$C_6$alkoxy)$C_1$-$C_6$alkoxy, mono- and di-($C_1$-$C_6$ alkyl)amino, amino$C_1$-$C_6$ alkyl, $C_1$-$C_6$alkylthio, mono- and di-($C_1$-$C_6$ alkyl)amino($C_1$-$C_6$ alkyl), $C_7$ cycloalkyl, $C_2$-$C_6$alkanoyl, $C_1$-$C_6$alkoxycarbonyl, heterocycloalkyl, amido, sulfonamido, and heteroaryl. In certain embodiments, $R_6$ and $R_7$ are each independently chosen from hydrogen and methyl. In certain embodiments, $R_6$ and $R_7$ are each hydrogen.

In certain embodiments, $R_2$ is chosen from $C_1$-$C_7$alkyl, such as $C_3$-$C_7$cycloalkyl, ($C_3$-$C_7$cycloalkyl)$C_1$-$C_7$ alkyl, heterocycloalkyl, (heterocycloalkyl)$C_1$-$C_2$ alkyl, ($C_1$-$C_6$alkoxy)$C_0$-$C_6$alkyl, ($C_1$-$C_6$alkoxy)$C_1$-$C_6$alkoxy, phenyl, and heteroaryl, each of which is optionally substituted. In certain embodiments, $R_2$ is chosen from phenyl and heteroaryl, each of which is optionally substituted.

In certain embodiments, $R_2$ is chosen from phenyl and pyridyl, each of which is optionally substituted with a substituent chosen from hydroxy, —CHO, —COOH, —CONH$_2$, and —CONHOH and is also optionally substituted with a substituent chosen from hydroxy, nitro, cyano, amino, sulfonamido, halo, $C_1$-$C_6$ alkyl, such as $C_3$-$C_6$cycloalkyl, $C_1$-$C_6$alkoxy, ($C_1$-$C_6$ alkoxy)$C_0$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl.

In certain embodiments, $R_2$ is chosen from phenyl and pyridyl, each of which is optionally substituted with a substituent chosen from hydroxy, —CHO, —COOH, and —CONH$_2$ and is also optionally substituted with one, two or three substituents independently chosen from hydroxy, nitro, cyano, halo, $C_1$-$C_4$alkyl, $C_2$-$C_4$alkanoyl, $C_1$-$C_2$haloalkyl, $C_1$-$C_2$haloalkoxy, $C_1$-$C_4$alkoxy, and mono- and di-$C_1$-$C_4$alkylamino.

In certain embodiments, $R_2$ is chosen from phenyl and pyridyl, each of which is optionally substituted with a group chosen from optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, optionally substituted (mono- and di-$C_1$-$C_6$alkylamino)$C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-$C_6$alkyl, optionally substituted ($C_1$-$C_6$alkoxy)($C_1$-$C_6$alkoxy)$C_1$-$C_6$alkoxy, optionally substituted heterocycloalkyl, optionally substituted aryl, and optionally substituted heteroaryl; and is also optionally substituted with one, two or three substituents independently chosen from hydroxy, nitro, cyano, amino, sulfonamido, halo, $C_1$-$C_6$ alkyl, such as $C_3$-$C_6$cycloalkyl, $C_1$-$C_6$alkoxy, ($C_1$-$C_6$ alkoxy)$C_1$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl.

In certain embodiments, $R_2$ is chosen from phenyl and pyridyl, each of which is optionally substituted with a substituent chosen from optionally substituted $C_1$-$C_6$hydroxyalkyl, optionally substituted (mono- and di-$C_1$-$C_6$alkylamino)$C_1$-$C_6$alkoxy, optionally substituted mono- and di($C_1$-$C_6$ alkyl)amino($C_1$-$C_6$alkyl), and optionally substituted ($C_1$-$C_6$alkoxy)($C_1$-$C_6$alkylamino)$C_0$-$C_6$alkyl; and is also optionally substituted with one, two or three substituents independently chosen from hydroxy, nitro, cyano, halo, $C_1$-$C_4$alkyl, $C_1$-$C_4$alkoxy, mono- and di-($C_1$-$C_6$ alkyl)amino, $C_1$-$C_2$haloalkyl, and $C_1$-$C_2$haloalkoxy. In certain embodiments, $R_2$ is chosen from phenyl and pyridyl, each of which is optionally substituted with a substituent chosen from $C_1$-$C_6$hydroxyalkyl, (mono- and di-$C_1$-$C_6$alkylamino)$C_1$-$C_6$alkoxy, mono- and di($C_1$-$C_6$ alkyl)amino($C_1$-$C_6$alkyl), and ($C_1$-$C_6$alkoxy)($C_1$-$C_6$alkylamino)$C_0$-$C_6$alkyl, and is also optionally substituted with one, two or three substituents independently chosen from hydroxy, nitro, cyano, halo, $C_1$-$C_2$alkyl, and $C_1$-$C_2$alkoxy.

In certain embodiments, $R_2$ is chosen from phenyl and pyridyl, each of which is substituted with -L-G, where L is chosen from optionally substituted $C_1$-$C_2$alkyl, optionally substituted $C_0$-$C_2$alkoxy, —(C=O)—, and optionally substituted —($C_1$-$C_2$alkyl)(C=O)—, and G is chosen from optionally substituted heterocycloalkyl, optionally substituted $C_3$-$C_7$cycloalkyl, optionally substituted aryl, and optionally substituted heteroaryl, and $R_2$ is also optionally substituted with one, two or three substituents independently chosen from hydroxy, nitro, cyano, amino, sulfonamido, halo, $C_1$-$C_6$ alkyl, such as $C_3$-$C_6$cycloalkyl, ($C_1$-$C_6$ alkoxy)$C_1$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl.

In certain embodiments, $R_2$ is chosen from phenyl and pyridyl, each of which is substituted with -L-G, where L is chosen from $C_1$-$C_2$alkyl and $C_0$-$C_2$alkoxy, and G is chosen from pyrrolidinyl, morpholinyl, thiomorpholinyl, piperazinyl, piperidinyl, dioxolanyl, furanyl, tetrahydrofuranyl, phenyl, and imidazolyl, which -L-G is optionally substituted with one, two, or three substituents independently chosen from hydroxy, cyano, halo, $C_1$-$C_2$alkyl, and $C_1$-$C_2$alkoxy; and $R_2$ is also optionally substituted with one, two or three substituents independently chosen from hydroxy, cyano, halo, $C_1$-$C_4$alkyl, $C_2$-$C_4$alkanoyl, $C_1$-$C_2$haloalkyl, $C_1$-$C_2$haloalkoxy, $C_1$-$C_4$alkoxy, and mono- and di-$C_1$-$C_4$alkylamino.

In certain embodiments, $R_2$ is chosen from phenyl and heteroaryl, each of which is optionally substituted with one, two or three substituents independently chosen from hydroxy, nitro, cyano, amino, halo, —CHO, —COOH, —CONH$_2$, $C_1$-$C_6$ alkyl, $C_2$-$C_6$alkenyl, $C_2$-$C_6$alkynyl, $C_1$-$C_6$alkoxy, $C_1$-$C_6$ haloalkyl, $C_1$-$C_6$ haloalkoxy, ($C_1$-$C_6$alkoxy)$C_1$-$C_6$alkoxy, mono- and di-($C_1$-$C_6$ alkyl)amino, amino($C_1$-$C_6$alkyl), $C_1$-$C_6$alkylthio, mono- and di-($C_1$-$C_6$ alkyl)amino($C_1$-$C_6$ alkyl), ($C_3$-$C_7$ cycloalkyl)$C_0$-$C_2$alkyl, $C_2$-$C_6$alkanoyl, $C_1$-$C_6$alkoxycarbonyl, (heterocycloalkyl)$C_0$-$C_2$alkyl, (heterocycloalkyl)$C_0$-$C_2$alkoxy, phenoxy, amido, sulfonamido, and heteroaryl.

In certain embodiments, $R_2$ is chosen from phenyl and pyridyl, each of which is optionally substituted with one, two or three substituents independently chosen from hydroxy, nitro, cyano, amino, halo, —CHO, —COOH, —CONH$_2$, $C_1$-$C_6$alkyl, $C_1$-$C_6$alkoxy, $C_1$-$C_2$haloalkyl, $C_1$-$C_2$haloalkoxy, ($C_1$-$C_6$alkoxy)$C_1$-$C_6$alkoxy, mono- and di-($C_1$-$C_6$alkyl)amino, amino($C_1$-$C_6$alkyl), $C_1$-$C_6$alkylthio, mono- and di-($C_1$-$C_6$ alkyl)amino$C_1$-$C_6$alkyl, ($C_3$-$C_7$cycloalkyl)$C_0$-$C_2$alkyl, $C_2$-$C_6$alkanoyl, $C_1$-$C_6$alkoxycarbonyl, (heterocycloalkyl)$C_0$-$C_2$alkyl, phenoxy, amido, and sulfonamido.

In certain embodiments, $R_2$ is chosen from phenyl and pyridyl, each of which is substituted with one, two or three substituents independently chosen from hydroxy, cyano, nitro, halo, $C_1$-$C_2$alkyl, $C_1$-$C_2$alkoxy, $C_1$-$C_2$haloalkyl, $C_1$-$C_2$haloalkoxy, ($C_1$-$C_6$alkoxy)$C_1$-$C_6$alkoxy, ($C_3$-$C_7$cycloalkyl)$C_0$-$C_2$alkyl, phenoxy, (heterocycloalkyl)$C_0$-$C_2$alkyl, and (heterocycloalkyl)$C_0$-$C_2$alkoxy, wherein heterocycloalkyl is independently chosen at each occurrence from pyrrolidinyl, morpholinyl, thiomorpholinyl, piperazinyl, piperidinyl, dioxolanyl, furanyl, tetrahydrofuranyl, phenyl, phenoxy, and imidazolyl.

In certain embodiments, when X is NR, $R_2$ is chosen from phenyl and pyridyl, each of which is substituted with one, two or three substituents independently chosen from cyano, nitro, halo, $C_1$-$C_2$alkyl, $C_1$-$C_2$alkoxy, and trifluoromethyl.

In certain embodiments, X is NR, and $R_2$ is selected from substituted $C_1$-$C_7$alkyl, such as substituted $C_3$-$C_7$cycloalkyl, substituted ($C_3$-$C_7$cycloalkyl)$C_1$-$C_7$ alkyl, substituted heterocycloalkyl, (heterocycloalkyl)$C_1$-$C_2$ alkyl, substituted ($C_1$-$C_6$alkoxy)$C_0$-$C_6$alkyl, substituted ($C_1$-$C_6$alkoxy)$C_1$-$C_6$alkoxy, substituted phenyl, and substituted heteroaryl,
wherein said substituted phenyl and substituted heteroaryl, are each substituted with one or more substituents chosen from hydroxy, —CHO, —COOH, —CONH$_2$, and —CONHOH, optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, (mono- and di-$C_1$-$C_6$alkylamino)$C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-$C_6$alkyl, optionally substituted ($C_1$-$C_6$alkoxy)($C_1$-$C_6$alkoxy)$C_1$-$C_6$alkoxy, optionally substituted heterocycloalkyl, optionally substituted aryl, optionally substituted heteroaryl, optionally substituted —$C_1$-$C_6$alkyl(C=O)OR$_8$, optionally substituted —$C_0$-$C_6$alkyl(C=O)NR$_8$R$_9$, optionally substituted —$C_1$-$C_6$alkylNR$_8$(SO$_2$)R$_9$, optionally substituted —$C_0$-$C_6$alkylNR$_8$(C=O)R$_9$, optionally substituted —$C_0$-$C_6$alkyl(SO$_2$)R$_8$, optionally substituted —$C_0$-$C_6$alkylNR$_8$(C=O)NR$_9$R$_{10}$ where $R_8$, $R_9$, and $R_{10}$ are independently hydrogen, hydroxy, $C_1$-$C_6$alkyl, $C_1$-$C_6$alkoxy, $C_3$-$C_7$cycloalkyl, and heterocycloalkyl, -L-G, where L is chosen from optionally substituted $C_1$-$C_2$alkyl, optionally substituted $C_0$-$C_2$alkoxy, —(C=O)—, and optionally substituted —($C_1$-$C_2$alkyl)(C=O)—, and G is chosen from optionally substituted heterocycloalkyl, optionally substituted $C_3$-$C_7$cycloalkyl, optionally substituted aryl, and optionally substituted heteroaryl, except that -L-G is not —O-phenyl; and
wherein said substituted phenyl and substituted heteroaryl, are each further optionally substituted with one or more substituent chosen from hydroxy, nitro, cyano, amino, sulfonamido, halo, $C_1$-$C_6$ alkyl, such as $C_3$-$C_7$cycloalkyl, ($C_1$-$C_6$ alkoxy)$C_0$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)R$_{13}$, wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, and heteroaryl.

The invention provides compounds of Formula I wherein:
X is O, S, or CH$_2$;
n is 0, 1, 2, or 3;
each occurrence of $R_1$ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl)amino($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)R$_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl (especially, each occurrence of $R_1$ is chosen from halo, methyl, and methoxy);
A is 1, 2, 3, or 4;
$Z_1$ is —CR$_4$R$_5$—;
each of $R_4$ and $R_5$ is independently chosen from hydrogen, $C_1$-$C_6$alkyl, and halo;
$Z_2$ is a meta-phenylene divalent linking group which divalent linking group is substituted with one group $R_2$—Q—;
Q is

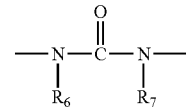

wherein $R_6$ and $R_7$ are each independently chosen from hydrogen and methyl; and
$R_2$ is chosen from phenyl and heteroaryl, each of which is optionally substituted.

The invention provides compounds of Formula I wherein:
X is O, S, or CH$_2$;
n is 0, 1, 2, or 3;
each occurrence of $R_1$ is chosen from hydroxy, cyano, halo, $C_1$-$C_2$alkyl, $C_1$-$C_2$alkoxy, $C_1$-$C_2$haloalkyl, and $C_1$-$C_2$haloalkoxy, (especially, each occurrence of $R_1$ is chosen from halo, methyl, and methoxy);
A is 1;
$Z_1$ is —$CR_4R_5$—;
$R_4$ and $R_5$ are both hydrogen;
$Z_2$ is a meta-phenylene divalent linking group which divalent linking group is substituted with one group $R_2$—Q—;
Q is

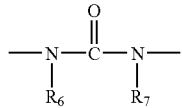

wherein $R_6$ and $R_7$ are each independently chosen from hydrogen and methyl; and
$R_2$ is chosen from phenyl and heteroaryl, each of which is optionally substituted.

The invention provides compounds of Formula I wherein:
X is O, S, or $CH_2$;
n is 0 and $R_1$ is absent;
A is 1;
$Z_1$ is —$CR_4R_5$—;
$R_4$ and $R_5$ are both hydrogen;
$Z_2$ is a meta-phenylene divalent linking group which divalent linking group is substituted with one group $R_2$—Q—;
Q is

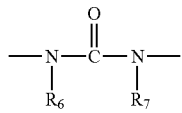

wherein $R_6$ and $R_7$ are each independently chosen from hydrogen and methyl; and
$R_2$ is chosen from phenyl and heteroaryl, each of which is optionally substituted.

The invention provides compounds of Formula I wherein:
X is NR;
R is chosen from hydrogen, $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, $C_2$-$C_6$ alkynyl; optionally substituted phenyl, and optionally substituted heteroaryl
n is 0, 1, 2, or 3;
each occurrence of $R_1$ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl)amino($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl (especially, each occurrence of $R_1$ is chosen from halo, methyl, and methoxy);
A is 1, 2, 3, or 4 (especially 3 or 4);
$Z_1$ is —$CR_4R_5$—;
each of $R_4$ and $R_5$ and independently chosen from hydrogen, $C_1$-$C_6$alkyl, and halo;

$R_3$ is chosen from hydrogen and $C_1$-$C_4$alkyl;
$Z_2$ is a meta-phenylene divalent linking group which divalent linking group is substituted with one group $R_2$—Q—;
Q is

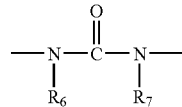

wherein $R_6$ and $R_7$ are each independently chosen from hydrogen and methyl; and
$R_2$ is chosen from substituted phenyl and substituted heteroaryl.

The invention provides compounds of Formula I wherein:
X is NR;
R is chosen from hydrogen; $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, and $C_2$-$C_6$ alkynyl;
n is 0, 1, 2, or 3;
each occurrence of $R_1$ is chosen from hydroxy, cyano, halo, $C_1$-$C_2$alkyl, $C_1$-$C_2$alkoxy, $C_1$-$C_2$haloalkyl, and $C_1$-$C_2$haloalkoxy, (especially, each occurrence of $R_1$ is chosen from halo, methyl, and methoxy);
A is 1, 2, 3, or 4 (especially 3 or 4);
$Z_1$ is —$CR_4R_5$—;
$R_4$ and $R_5$ are both hydrogen;
$R_3$ is chosen from hydrogen and $C_1$-$C_4$alkyl;
$Z_2$ is a meta-phenylene divalent linking group which divalent linking group is substituted with one group $R_2$—Q—;
Q is

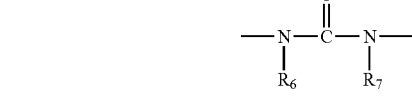

wherein $R_6$ and $R_7$ are each independently chosen from hydrogen and methyl; and
$R_2$ is selected from substituted $C_1$-$C_7$alkyl, such as substituted $C_3$-$C_7$cycloalkyl, substituted ($C_3$-$C_7$cycloalkyl)$C_1$-$C_7$ alkyl, substituted heterocycloalkyl, (heterocycloalkyl)$C_1$-$C_2$ alkyl, substituted ($C_1$-$C_6$alkoxy)$C_0$-$C_6$alkyl, substituted ($C_1$-$C_6$alkoxy)$C_1$-$C_6$alkoxy, substituted phenyl, and substituted heteroaryl,
wherein said substituted phenyl and substituted heteroaryl are each substituted with one or more substituents chosen from hydroxy, —CHO, —COOH, —$CONH_2$, and —CONHOH, optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, (mono- and di-$C_1$-$C_6$alkylamino)$C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-$C_6$alkyl, optionally substituted ($C_1$-$C_6$alkoxy)($C_1$-$C_6$alkoxy)$C_1$-$C_6$alkoxy, optionally substituted heterocycloalkyl, optionally substituted aryl, optionally substituted heteroaryl, optionally substituted —$C_1$-$C_6$alkyl(C=O)$OR_8$, optionally substituted —$C_0$-$C_6$alkyl(C=O)$NR_8R_9$, optionally substituted —$C_0$-$C_6$alkyl$NR_8$($SO_2$)$R_8$, optionally substituted —$C_0$-$C_6$alkyl$NR_8$(C=O)$R_9$, optionally substituted —$C_0$-

$C_6$alkyl($SO_2$)$R_8$, optionally substituted —$C_0$-$C_6$alkylN$R_8$(C=O)N$R_9R_{10}$ where $R_8$, $R_9$, and $R_{10}$ are independently chosen from hydrogen, hydroxy, $C_1$-$C_6$alkyl, $C_1$-$C_6$alkoxy, $C_3$-$C_7$cycloalkyl, and heterocycloalkyl, -L-G, where L is chosen from optionally substituted $C_1$-$C_2$alkyl, optionally substituted $C_0$-$C_2$alkoxy, —(C=O)—, and optionally substituted —($C_1$-$C_2$alkyl)(C=O)—, and G is chosen from optionally substituted heterocycloalkyl, optionally substituted $C_3$-$C_7$cycloalkyl, optionally substituted aryl, or optionally substituted heteroaryl, except that -L-G is not —O-phenyl; and wherein said substituted phenyl and substituted heteroaryl, are each further optionally substituted with one or more substituents chosen from hydroxy, nitro, cyano, amino, sulfonamido, halo, $C_1$-$C_6$ alkyl, such as $C_3$-$C_7$cycloalkyl, ($C_1$-$C_6$ alkoxy)$C_0$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)$R_{13}$, wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, and heteroaryl.

The invention provides compounds of Formula I wherein:
X is NR;
R is chosen from hydrogen and $C_1$-$C_4$alkyl;
n is 0 and $R_1$ is absent;
A is 1, 2, 3, or 4 (especially 3 or 4);
$Z_1$ is —$CR_4R_5$—;
$R_4$ and $R_5$ are both hydrogen;
$R_3$ is chosen from hydrogen and $C_1$-$C_4$alkyl;
$Z_2$ is a meta-phenylene divalent linking group which divalent linking group is substituted with one group $R_2$—Q—;
Q is

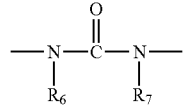

wherein $R_6$ and $R_7$ are each independently chosen from hydrogen and methyl; and $R_2$ is selected from substituted $C_1$-$C_7$alkyl, such as substituted $C_3$-$C_7$cycloalkyl, substituted ($C_3$-$C_7$cycloalkyl)$C_1$-$C_7$ alkyl, substituted heterocycloalkyl, (heterocycloalkyl)$C_1$-$C_2$ alkyl, substituted ($C_1$-$C_6$alkoxy)$C_0$-$C_6$alkyl, substituted ($C_1$-$C_6$alkoxy)$C_1$-$C_6$alkoxy, substituted phenyl, and substituted heteroaryl, wherein said substituted phenyl and substituted heteroaryl are each substituted with one or more substituents chosen from hydroxy, —CHO, —COOH, —CONH$_2$, and —CONHOH, optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, (mono- and di-$C_1$-$C_6$alkylamino)$C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-$C_6$alkyl, optionally substituted ($C_1$-$C_6$alkoxy)($C_1$-$C_6$alkoxy)$C_1$-$C_6$alkoxy, optionally substituted heterocycloalkyl, optionally substituted aryl, optionally substituted heteroaryl, optionally substituted —$C_1$-$C_6$alkyl(C=O)O$R_8$, optionally substituted —$C_0$-$C_6$alkyl(C=O)N$R_8R_9$, optionally substituted —$C_1$-$C_6$alkylN$R_8$(SO$_2$)$R_9$, optionally substituted —$C_0$-$C_6$alkylN$R_8$(C=O)$R_9$, optionally substituted —$C_1$-$C_6$alkyl(SO$_2$)$R_8$, optionally substituted —$C_0$-$C_6$alkylN$R_8$(C=O)N$R_9R_{10}$ where $R_8$, $R_9$, and $R_{10}$ are independently chosen from hydrogen, hydroxy, $C_1$-$C_6$alkyl, $C_1$-$C_6$alkoxy, $C_3$-$C_7$cycloalkyl, and heterocycloalkyl, -L-G, where L is chosen from optionally substituted $C_1$-$C_2$alkyl, optionally substituted $C_0$-$C_2$alkoxy, —(C=O)—, and optionally substituted —($C_1$-$C_2$alkyl)(C=O)—, and G is chosen from optionally substituted heterocycloalkyl, optionally substituted $C_3$-$C_7$cycloalkyl, optionally substituted aryl, or optionally substituted heteroaryl, except that -L-G is not —O-phenyl; and wherein said substituted phenyl and substituted heteroaryl, are each further optionally substituted with one or more substituent chosen from hydroxy, nitro, cyano, amino, sulfonamido, halo, $C_1$-$C_6$ alkyl, such as $C_3$-$C_7$cycloalkyl, ($C_1$-$C_6$ alkoxy)$C_0$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino, $C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_{C6}$alkylester, phenoxy, and —(C=O)$R_{13}$, wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, and heteroaryl.

The invention provides compounds of Formula I wherein:
X is NR;
R is amino($C_1$-$C_4$alkyl);
n is 0 and $R_1$ is absent;
A is 1, 2, 3, or 4 (especially 3 or 4);
$Z_1$ is —$CR_4R_5$—;
$R_4$ and $R_5$ are both hydrogen;
$R_3$ is chosen from hydrogen and $C_1$-$C_4$alkyl;
$Z_2$ is a meta-phenylene divalent linking group which divalent linking group is substituted with one group $R_2$—Q—;
Q is

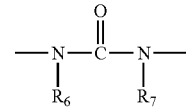

wherein $R_6$ and $R_7$ are each independently chosen from hydrogen and methyl; and $R_2$ is selected from substituted $C_1$-$C_7$alkyl, such as substituted $C_3$-$C_7$cycloalkyl, substituted ($C_3$-$C_7$cycloalkyl)$C_1$-$C_7$ alkyl, substituted heterocycloalkyl, (heterocycloalkyl)$C_1$-$C_2$ alkyl, substituted ($C_1$-$C_6$alkoxy)$C_0$-$C_6$alkyl, substituted ($C_1$-$C_6$alkoxy)$C_1$-$C_6$alkoxy, substituted phenyl, and substituted heteroaryl, wherein said substituted phenyl and substituted heteroaryl, are each substituted with one or more substituents chosen from hydroxy, —CHO, —COOH, —CONH$_2$, and —CONHOH, optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, (mono- and di-$C_1$-$C_6$alkylamino)$C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-

$C_6$alkyl, optionally substituted $(C_1-C_6$alkoxy)$(C_1-C_6$alkoxy)$C_1-C_6$alkoxy, optionally substituted heterocycloalkyl, optionally substituted aryl, optionally substituted heteroaryl, optionally substituted —$C_1-C_6$alkyl(C=O)OR$_8$, optionally substituted —$C_0-C_6$alkyl(C=O)NR$_8$R$_9$, optionally substituted —$C_1-C_6$alkylNR$_8$(SO$_2$)R$_9$, optionally substituted —$C_0-C_6$alkylNR$_8$(C=O)R$_9$, optionally substituted —$C_0-C_6$alkyl(SO$_2$)R$_8$, optionally substituted —$C_0-C_6$alkylNR$_8$(C=O)NR$_9$R$_{10}$ where R$_8$, R$_9$, and R$_{10}$ are independently chosen from hydrogen, hydroxy, $C_1-C_6$alkyl, $C_1-C_6$alkoxy, $C_3-C_7$cycloalkyl, and heterocycloalkyl, -L-G, where L is chosen from optionally substituted $C_1-C_2$alkyl, optionally substituted $C_0-C_2$alkoxy, —(C=O)—, and optionally substituted —(C$_1$-C$_2$alkyl)(C=O)—, and G is chosen from optionally substituted heterocycloalkyl, optionally substituted $C_3-C_7$cycloalkyl, optionally substituted aryl, and optionally substituted heteroaryl, except that -L-G is not —O-phenyl; and wherein said substituted phenyl and substituted heteroaryl, are each further optionally substituted with one or more substituent chosen from hydroxy, nitro, cyano, amino, sulfonamido, halo, $C_1-C_6$ alkyl, such as $C_3-C_7$cycloalkyl, $(C_1-C_6$ alkoxy)$C_0-C_6$alkyl, $(C_1-C_6$alkoxy)$C_1-C_6$alkoxy, $C_7$cycloalkyl, amino$C_1-C_6$alkyl, mono- and di($C_1-C_6$ alkyl)amino, $C_1-C_6$haloalkyl, $C_1-C_6$haloalkoxy, $C_2-C_6$alkenyl, $C_2-C_6$alkynyl, $C_1-C_6$alkylthio, oxo, $C_1-C_6$alkylester, phenoxy, and —(C=O)R$_{13}$, wherein R$_{13}$ is $C_1-C_6$ alkyl, such as $C_3-C_6$cycloalkyl, $C_7$cycloalkyl, $C_2-C_6$ alkanoyl, $C_1-C_6$alkoxycarbonyl, heterocycloalkyl, or heteroaryl.

In certain embodiments, the compound of Formula I is chosen from 1-(2-Methoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2-methoxy-phenyl)-3-{3-[8-(pyridin-4-ylmethoxy)-imidazo[1,2-a]pyrazin-6-yl]-phenyl}-urea;

1-(2-Chloro-5-trifluoromethyl-phenyl)-3-{3-[8-(pyridin-4-ylmethoxy)-imidazo[1,2-a]pyrazin-6-yl]-phenyl}-urea;

1-(2-Fluoro-5-trifluoromethyl-phenyl)-3-{3-[8-(pyridin-4-ylmethoxy)-imidazo[1,2-a]pyrazin-6-yl]-phenyl}-urea;

1-[2-(2-Methoxy-ethoxy)-5-trifluoromethyl-phenyl]-3-{3-[8-(pyridin-4-ylmethoxy)-imidazo[1,2-a]pyrazin-6-yl]-phenyl}-urea;

1-(2-Methoxy-5-nitro-phenyl)-3-{3-[8-(pyridin-4-ylmethoxy)-imidazo[1,2-a]pyrazin-6-yl]-phenyl}-urea;

1-{3-[8-(Pyridin-4-ylmethoxy)-imidazo[1,2-a]pyrazin-6-yl]-phenyl}-3-(3-trifluoromethyl-phenyl)-urea;

1-(2,4-Dimethoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2,4-dimethoxy-phenyl)-3-{3-[8-(pyridin-4-ylmethoxy)-imidazo[1,2-a]pyrazin-6-yl]-phenyl}-urea;

1-(3-Cyano-phenyl)-3-{3-[8-(pyridin-4-ylmethoxy)-imidazo[1,2-a]pyrazin-6-yl]-phenyl}-urea;

1-(2,4-Diethoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2-methoxy-phenyl)-3-{3-[8-(2-methyl-pyridin-4-ylmethoxy)-imidazo[1,2-a]pyrazin-6-yl]-phenyl}-urea;

1-(3-{8-[(Pyridin-4-ylmethyl)-amino]-imidazo[1,2-a]pyrazin-6-yl}-phenyl)-3-m-tolyl-urea;

1-(3-Chloro-phenyl)-3-(3-{8-[(pyridin-4-ylmethyl)-amino]-imidazo[1,2-a]pyrazin-6-yl}-phenyl)-urea;

1-(4-Methyl-3-trifluoromethyl-phenyl)-3-(3-{8-[(pyridin-4-ylmethyl)-amino]-imidazo[1,2-a]pyrazin-6-yl}-phenyl)-urea;

1-(5-Chloro-2-methoxy-phenyl)-3-(3-{8-[(pyridin-4-ylmethyl)-amino]-imidazo[1,2-a]pyrazin-6-yl}-phenyl)-urea;

1-(2-Chloro-5-trifluoromethyl-phenyl)-3-(3-{8-[(pyridin-4-ylmethyl)-amino]-imidazo[1,2-a]pyrazin-6-yl}-phenyl)-urea;

1-(2-Fluoro-5-trifluoromethyl-phenyl)-3-{3-[8-(methyl-pyridin-4-ylmethyl-amino)-imidazo[1,2-a]pyrazin-6-yl]-phenyl}-urea;

1-(5-Chloro-2-methoxy-phenyl)-3-{3-[8-(methyl-pyridin-4-ylmethyl-amino)-imidazo[1,2-a]pyrazin-6-yl]-phenyl}-urea;

1-(2-Chloro-5-trifluoromethyl-phenyl)-3-{3-[8-(methyl-pyridin-4-ylmethyl-amino)-imidazo[1,2-a]pyrazin-6-yl]-phenyl}-urea;

1-{3-[8-(2-Pyridin-4-yl-ethylamino)-imidazo[1,2-a]pyrazin-6-yl]-phenyl}-3-(3-trifluoromethyl-phenyl)-urea;

1-(5-Chloro-2-methoxy-phenyl)-3-{3-[8-(2-pyridin-4-yl-ethylamino)-imidazo[1,2-a]pyrazin-6-yl]-phenyl}-urea;

1-(2-Fluoro-5-trifluoromethyl-phenyl)-3-(3-{8-[(pyridin-4-ylmethyl)-amino]-imidazo[1,2-a]pyrazin-6-yl}-phenyl)-urea;

1-(2-Methoxy-5-trifluoromethyl-phenyl)-3-(3-{8-[(pyridin-4-ylmethyl)-amino]-imidazo[1,2-a]pyrazin-6-yl}-phenyl)-urea;

1-(2-Methoxy-5-trifluoromethyl-phenyl)-3-{3-[8-(methyl-pyridin-4-ylmethyl-amino)-imidazo[1,2-a]pyrazin-6-yl]-phenyl}-urea;

1-(2-Methoxy-5-nitro-phenyl)-3-{3-[8-(methyl-pyridin-4-ylmethyl-amino)-imidazo[1,2-a]pyrazin-6-yl]-phenyl}-urea;

1-(5-Chloro-72,4-dimethoxy-phenyl)-3-(3-{8-[(pyridin-4-ylmethyl)-amino]-imidazo[1,2-a]pyrazin-6-yl}-phenyl)-urea;

1-(3-{8-[(Pyridin-4-ylmethyl)-amino]-imidazo[1,2-a]pyrazin-6-yl}-phenyl)-3-(2,4,5-trichloro-phenyl)-urea;

1-(5-Chloro-2,4-dimethoxy-phenyl)-3-{3-[8-(methyl-pyridin-4-ylmethyl-amino)-imidazo[1,2-a]pyrazin-6-yl]-phenyl}-urea;

1-{3-[8-(Methyl-pyridin-4-ylmethyl-amino)-imidazo[1,2-a]pyrazin-6-yl]-phenyl}-3-(2,4,5-trichloro-phenyl)-urea;

1-(2-Methoxy-5-nitro-phenyl)-3-(3-{8-[(pyridin-4-ylmethyl)-amino]-imidazo[1,2-a]pyrazin-6-yl}-phenyl)-urea;

1-(2-Ethoxy-5-trifluoromethyl-phenyl)-3-(3-{8-[(pyridin-4-ylmethyl)-amino]-imidazo[1,2-a]pyrazin-6-yl}-phenyl)-urea;

1-(2-Isopropoxy-5-trifluoromethyl-phenyl)-3-(3-{8-[(pyridin-4-ylmethyl)-amino]-imidazo[1,2-a]pyrazin-6-yl}-phenyl)-urea;

1-(2,4-Dimethoxy-5-trifluoromethyl-phenyl)-3-(3-{8-[(pyridin-4-ylmethyl)-amino]-imidazo[1,2-a]pyrazin-6-yl}-phenyl)-urea;

1-(2,4-Dimethoxy-5-trifluoromethyl-phenyl)-3-{3-[8-(methyl-pyridin-4-ylmethyl-amino)-imidazo[1,2-a]pyrazin-6-yl]-phenyl}-urea;

1-(4-Ethoxy-3-trifluoromethyl-phenyl)-3-(3-{8-[(pyridin-4-ylmethyl)-amino]-imidazo[1,2-a]pyrazin-6-yl}-phenyl)-urea;

1-(5-Chloro-2-phenoxy-phenyl)-3-(3-{8-[(pyridin-4-ylmethyl)-amino]-imidazo[1,2-a]pyrazin-6-yl}-phenyl)-urea;

1-(4-Fluoro-3-trifluoromethyl-phenyl)-3-(3-{8-[(pyridin-4-ylmethyl)-amino]-imidazo[1,2-a]pyrazin-6-yl}-phenyl)-urea;

1-[2-(2-Methoxy-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(2-Methoxy-ethoxy)-5-trifluoromethyl-phenyl]-3-{3-[8-(methyl-pyridin-4-ylmethyl-amino)-imidazo[1,2-a]pyrazin-6-yl]-phenyl}-urea;

1-(2,4-Diethoxy-5-trifluoromethyl-phenyl)-3-(3-{8-[(pyridin-4-ylmethyl)-amino]-imidazo[1,2-a]pyrazin-6-yl}-phenyl)-urea;

1-(2,4-Diethoxy-5-trifluoromethyl-phenyl)-3-{3-[8-(methyl-pyridin-4 4-ylmethyl-amino)-imidazo[1,2-a]pyrazin-6-yl]-phenyl}-urea;

1-[2-(2-Hydroxy-ethoxy)-5-trifluoromethyl-phenyl]-3-(3-{8-[(pyridin-4-ylmethyl)-amino]-imidazo[1,2-a]pyrazin-6-yl}-phenyl)-urea;

{2-[3-(3-{8-[(Pyridin-4-ylmethyl)-amino)-imidazo[1,2-a]pyrazin-6-yl]-phenyl)-ureido]-4-trifluoromethyl-phenoxy}-acetic acid;

1-[2-(2-Methylamino-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(2-Dimethylamino-ethoxy)-5-trifluoromethyl-phenyl]-3-(3-{8-[(pyridin-4-ylmethyl)-amino]-imidazo[1,2-a]pyrazin-6-yl}-phenyl) urea;

1-(3-Chloro-4-hydroxymethyl-phenyl)-3-(3-{8-[(pyridin-4-ylmethyl)-amino]-imidazo[1,2-a]pyrazin-6-yl}-phenyl)-urea;

1-[5-Chloro-2-([1,3]dioxolan-2-ylmethoxy)-phenyl]-3-(3-{8-[(pyridin-4-methyl)-amino]-imidazo[1,2-a]pyrazin-6-yl}-phenyl)-urea;

1-[5-Chloro-2-(2-hydroxy-ethoxy)-phenyl]-3-(3-{8-[(pyridin-4-ylmethyl)-amino]-imidazo[1,2-a]pyrazin-6-yl}-phenyl)-urea;

1-[5-Chloro-2-(2-methylamino-ethoxy)-phenyl]-3-(3-{8-[(pyridin-4-ylmethyl)-amino]-imidazo[1,2-a]pyrazin-6-yl}-phenyl)-urea;

1-[5-Chloro-2-(2-dimethylamino-ethoxy)-phenyl]-3-(3-{8-[(pyridin-4-ylmethyl)-amino]-imidazo[1,2-a]pyrazin-6-yl}-phenyl)-urea;

1-[2-(2-Piperazin-1-yl-ethoxy)-5-trifluoromethyl-phenyl]-3-(3-{8-[(pyridin-4-methyl)-amino]-imidazo[1,2-a]pyrazin-6-yl}-phenyl)-urea;

1-[2-(2-Morpholin-4-yl-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(3-Hydroxy-propoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(3-Methylamino-propoxy)-5-trifluoromethyl-phenyl]-3-(3-{8-[(pyridin-4-ylmethyl)-amino]-imidazo[1,2-a]pyrazin-6-yl}-phenyl)-urea;

1-[5-Chloro-2-(3-hydroxy-propoxy)-phenyl]-3-(3-{8-[(pyridin-4-ylmethyl)-amino]-imidazo[1,2-a]pyrazin-6-yl}-phenyl)-urea;

1-(3-{8-[(2-Amino-ethyl)-pyridin-4-ylmethyl-amino]-imidazo[1,2-a]pyrazin-6-yl}-phenyl)-3-(4-methoxy-3-trifluoromethyl-phenyl)-urea;

1-(3-{8-[(Pyridin-4-ylmethyl)-amino]-imidazo[1,2-a]pyrazin-6-yl}-phenyl)-3-[2-(2-pyrrolidin-1-yl-ethoxy)-5-trifluoromethyl-phenyl]-urea; and 1-(2-Hydroxy-5-trifluoromethyl-phenyl)-3-(3-{8-[(pyridin-4-ylmethyl)-amino]-imidazo[1,2-a]pyrazin-6-yl}-phenyl)-urea.

In certain embodiments, the compound of Formula I is chosen from 1-(2-Methoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2-methoxy-phenyl)-3-{3-[8-(pyridin-4-ylmethoxy)-imidazo[1,2-a]pyrazin-6-yl]-phenyl}-urea;

1-(2-Chloro-5-trifluoromethyl-phenyl)-3-{3-[8-(pyridin-4-ylmethoxy)-imidazo[1,2-a]pyrazin-6-yl]-phenyl}-urea;

1-(2-Fluoro-5-trifluoromethyl-phenyl)-3-{3-[8-(pyridin-4-ylmethoxy)-imidazo[1,2-a]pyrazin-6-yl]-phenyl}-urea;

1-[2-(2-Methoxy-ethoxy)-5-trifluoromethyl-phenyl]-3-{3-[8-(pyridin-4-ylmethoxy)-imidazo[1,2-a]pyrazin-6-yl]-phenyl}-urea;

1-(2-Methoxy-5-nitro-phenyl)-3-{3-[8-(pyridin-4-ylmethoxy)-imidazo[1,2-a]pyrazin-6-yl]-phenyl}-urea;

1-{3-[8-(Pyridin-4-ylmethoxy)-imidazo[1,2-a]pyrazin-6-yl]-phenyl}-3-(3-trifluoromethyl-phenyl)-urea;

1-(2,4-Dimethoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2,4-dimethoxy-phenyl)-3-{3-[8-(pyridin-4-ylmethoxy)-imidazo[1,2-yl]-phenyl}-urea;

1-(3-Cyano-phenyl)-3-{3-[8-(pyridin-4-ylmethoxy)-imidazo[1,2-a]pyrazin-6-yl]-phenyl}-urea;

1-(2,4-Diethoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2-methoxy-phenyl)-3-{3-[8-(2-methyl-pyridin-4-ylmethoxy)-imidazo[1,2-a]pyrazin-6-yl]-phenyl}-urea 1-[2-(2-Hydroxy-ethoxy)-5-trifluoromethyl-phenyl]-3-(3-{8-[(pyridin-4-ylmethyl)-amino]-imidazo[1,2-a]pyrazin-6-yl}-phenyl)-urea;

{2-[3-(3-{8-[(Pyridin-4-ylmethyl)-amino]-imidazo[1,2-a]pyrazin-6-yl}-phenyl)-ureido]-4-trifluoromethyl-phenoxy}-acetic acid;

1-[2-(2-Methylamino-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(2-Dimethylamino-ethoxy)-5-trifluoromethyl-phenyl]-3-(3-{8-[(pyridin-4-ylmethyl)-amino]-imidazo[1,2-a]pyrazin-6-yl}-phenyl) urea;

1-(3-Chloro-4-hydroxymethyl-phenyl)-3-(3-{8-[(pyridin-4-ylmethyl)-amino]-imidazo[1,2-a]pyrazin-6-yl}-phenyl)-urea;

1-[5-Chloro-2-([1,3]dioxolan-2-ylmethoxy)-phenyl]-3-(3-{8-[(pyridin-4-ylmethyl)-amino]-imidazo[1,2-a]pyrazin-6-yl}-phenyl)-urea;

1-[5-Chloro-2-(2-hydroxy-ethoxy)-phenyl]-3-(3-{8-[(pyridin-4-ylmethyl)-amino]-imidazo[1,2-a]pyrazin-6-yl}-phenyl)-urea;

1-[5-Chloro-2-(2-methylamino-ethoxy)-phenyl]-3-(3-{8-[(pyridin-4-ylmethyl)-amino]-imidazo[1,2-a]pyrazin-6-yl}-phenyl)-urea;

1-[5-Chloro-2-(2-dimethylamino-ethoxy)-phenyl]-3-(3-{8-[(pyridin-4-ylmethyl)-amino]-imidazo[1,2-a]pyrazin-6-yl}-phenyl)-urea;

1-[2-(2-Piperazin-1-yl-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(2-Morpholin-4-yl-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(3-Hydroxy-propoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(3-Methylamino-propoxy)-5-trifluoromethyl-phenyl]-3-(3-{8-[(pyridin-4-ylmethyl)-amino]-imidazo[1,2-a]pyrazin-6-yl}-phenyl)-urea;

1-[5-Chloro-2-(3-hydroxy-propoxy)-phenyl]-3-(3-{8-[(pyridin-4-ylmethyl)-amino]-imidazo[1,2-a]pyrazin-6-yl}-phenyl)-urea 1-(3-{8-[(Pyridin-4-ylmethyl)-amino]-imidazo[1,2-a]pyrazin-6-yl}-phenyl)-3-[2-(2-pyrrolidin-1-yl-ethoxy)-5-trifluoromethyl-phenyl]-urea; and 1-(2-Hydroxy-5-trifluoromethyl-phenyl)-3-(3-{8-[(pyridin-4-ylmethyl)-amino]-imidazo[1,2-a]pyrazin-6-yl}-phenyl)-urea.

Compounds, salts, and any other pharmaceutically acceptable forms of the invention, as defined above to be encompassed within the terms "compound" and "compounds," can be administered as the neat chemical, but, in certain embodiments, are administered as a pharmaceutical composition or formulation. Accordingly, the invention provides pharmaceutical formulations comprising a compound including, of course, a pharmaceutically acceptable form, of Formula I, together with one or more pharmaceutically acceptable carriers, excipients, adjuvants, diluents, or other ingredients.

Pharmaceutical carriers must be of sufficiently high purity and sufficiently low toxicity to render them suitable for administration to the animal being treated. The carrier can be inert or it can possess pharmaceutical benefits. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention. In other words, combination therapy is contemplated.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of the invention, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease, disorder, or condition treated and may be empirically determined.

Compounds of the invention may be administered orally, topically, parenterally, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. Oral formulations contain between 0.1 and 99% of a compound of the invention and usually at least about 5% (weight %) of a compound of the present invention. Some embodiments contain from about 25% to about 50% or from 5% to 75% of a compound of invention.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n- propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Compounds of the invention may be administered parenterally in a sterile medium. Parenteral administration includes subcutaneous injections, intravenous, intramuscular, intrathecal injection or infusion techniques. The compound or compounds of the invention, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least about 90% by weight of the total composition. Certain carriers for parenteral administration include propylene glycol, ethyl oleate, pyrrolidone, ethanol, and sesame oil.

Compounds of the invention may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Compounds of the invention may be formulated for local or topical application, such as for topical application to the skin and mucous membranes, such as in the eye, in the form of gels, creams, and lotions and for application to the eye. Topical compositions of the present invention may be in any form including, for example, solutions, creams, ointments, gels, lotions, milks, cleansers, moisturizers, sprays, skin patches, and the like.

Such solutions may be formulated as 0.01% -10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients may be used, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

The compositions of the present invention may also optionally comprise an activity enhancer. The activity enhancer can be chosen from a wide variety of molecules that function in different ways to enhance antimicrobial effects of compounds of the present invention. Particular classes of activity enhancers include skin penetration enhancers and absorption enhancers.

Pharmaceutical compositions of the invention may also contain additional active agents that can be chosen from a wide variety of molecules, which can function in different ways to enhance the therapeutic effects of a compound of the present invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

The invention includes packaged pharmaceutical formulations. Such packaged formulations include a pharmaceutical composition containing one or more compounds, including of course salts and other pharmaceutically acceptable forms thereof, of the invention in a container and instructions for using the composition to treat a patient (typically a mammal and more typically, a human patient) suffering from a disease or disorder responsive to kinase modulation or Hsp90 complex modulation, or prevent such a disease or disorder in a patient.

The invention includes providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing, the compounds of the invention can be administered alone, as mixtures, or in combination with other active agents.

The compounds of the present invention can be useful for the treatment of diseases and disorders responsive to kinase modulation. The compounds of the present invention can be useful for the treatment of diseases and disorders responsive to Hsp90 complex modulation. As used herein, "modulation" refers to a change in kinase or Hsp90 complex activity as a direct or indirect response to the presence of a compound of Formula I, relative to the activity of the kinase or Hsp90 complex in the absence of the compound. The change may be an increase in activity or a decrease in activity, and may be due to the direct interaction of the compound with the kinase or Hsp90 complex, or due to the interaction of the compound with one or more other factors that in turn affect kinase activity or Hsp90 complex activity. For example, the presence of the compound may increase or decrease kinase activity by directly binding to the kinase, by causing (directly or indirectly) another factor to increase or decrease the kinase activity, or by (directly or indirectly) increasing or decreasing the amount of kinase present in the cell or organism.

In certain embodiments, compounds described herein are modulators of protein kinases. In certain embodiments, the compounds described herein are inhibitors of the protein kinases. In certain embodiments, the compounds inhibit at least one of $EphB_4$, Tie-2, c-Kit, PDGF-R$\alpha$, and VEGF-R2 kinases. In certain embodiments, the compounds inhibit more than one of $EphB_4$, Tie-2, c-Kit, PDGF-R$\alpha$, and VEGF-R2 kinases. In certain embodiments, the compounds modulate the Hsp90 complex.

Accordingly, the invention includes a method of treating a patient, such as a human patient, having a disease or disorder responsive to kinase modulation, comprising administrating to the patient a therapeutically effective amount of a compound of Formula I. The invention includes a method of treating a patient, such as a human patient, having a disease or disorder responsive to Hsp90 complex modulation, comprising administrating to the patient a therapeutically effective amount of a compound of Formula I.

A method of treating a patient having a disease or disorder responsive to kinase, particularly $EphB_4$ kinase modulation comprising administering to the patient a therapeutically effective amount of one or more of the compounds of Formula I is provided. A method of treating a patient having a disease or disorder responsive to Hsp90 complex modulation comprising administering to the patient a therapeutically effective amount of one or more of the compounds of Formula I also is provided.

Also provided is the use of a compound of Formula I for the manufacture of a medicament for the treatment of a patient having a disease or disorder responsive to kinase, particularly $EphB_4$ kinase. Also provided is the use of a compound of Formula I for the manufacture of a medicament for the treatment of a patient having a disease or disorder responsive to Hsp90 complex modulation. Also provided is the use of a compound of Formula I for the manufacture of a medicament for the treatment of a patient having angiogenesis.

In some embodiments, the compounds of Formula I inhibit at least one of $EphB_4$, Tie-2, c-Kit, PDGF-R$\alpha$, and VEGF-R2 kinases and can be useful for the treatment of diseases and disorders responsive to modulation of at least one of such kinases. In some embodiments, the disease or disorder is characterized by angiogenesis supporting solid tumor growth or dysregulated local vascularization.

Methods of treatment also include modulating kinase activity, by inhibiting ATP binding or hydrolysis by a kinase or by some other mechanism, in vivo, in a patient suffering from a disease or disorder responsive to kinase modulation, by administering a sufficient concentration of a compound of Formula I to inhibit kinase activity in vitro. Methods of treatment also include modulating Hsp90 complex activity, by inhibiting the Hsp90 complex, in vivo, in a patient suffering from a disease or disorder responsive to Hsp90 complex modulation, by administering a sufficient concentration of a compound of Formula I to inhibit Hsp90 complex activity in vitro. By "sufficient concentration" of a compound administered to the patient is meant the concentration of the compound available in the patient's system to combat the disease or disorder. Such a concentration may be ascertained experimentally, for example by assaying blood concentration of the compound, or theoretically, by calculating bioavailability.

In some embodiments, the condition responsive to kinase modulation is cancer or a disease or disorder characterized by a change in angiogenesis. In some embodiments, the condition responsive to Hsp90 complex modulation is cancer or a disease or disorder characterized by a change in angiogenesis.

The invention includes a method of treating a patient having cancer or a disease or disorder characterized by a change in angiogenesis by administering a compound of Formula I. The invention provides methods of treatment in which a compound of the invention is the only active agent given to a patient and also includes methods of treatment in which a compound of Formula I is given to a patient with an additional active agent.

Certain compounds described herein can be useful for treating a patient suffering from a disease or disorder responsive to kinase modulation.

Protein kinases, the largest family of human enzymes, are now considered to be the largest druggable target class. Encompassing well over 500 proteins (2% of the human genome), kinases play critical roles in signaling pathways controlling fundamental cellular processes such as proliferation, differentiation, and death (apoptosis). Abnormal kinase activity has been implicated in a wide range of diseases, including multiple cancers and autoimmune and inflammatory diseases. The multifaceted role of kinases in key cell signaling pathways provides a significant opportunity to identify novel drugs targeting kinases and signaling pathways. Accordingly, there is intense industry-wide interest in this target family, with kinase related research accounting for nearly 25% of the discovery programs at many pharmaceutical and biotechnology companies. The recently demonstrated efficacy of multiple kinase inhibitors in the treatment of cancer, including the dramatic clinical activity of the kinase inhibitor GLEEVEC in patients with various tumors, is testimony to the great clinical potential of kinase and other signal transduction inhibitors as therapeutics.

Kinases are implicated in a large variety of diseases, as certain mutations in protein kinases can lead to activation of pathways causing, for example, the production of tumors, while other mutations in protein kinases block pathways and prevent a response.

Altered PKA (cyclic AMP-dependent protein kinase) expression is implicated in a variety of disorders and diseases including cancer, thyroid disorders, diabetes, atherosclerosis, and cardiovascular disease. Altered MAP (mitogen-activated protein) kinase expression is implicated in a variety of disease conditions including cancer, inflammation, immune disorders, and disorders affecting growth and development. RTKs (receptor tyrosine kinases), CDKs and STKs (serine/threonine kinases) have all been implicated in a host of pathogenic conditions including, significantly, large number of diverse cancers. Other pathogenic conditions that have been associated with PTKs include, psoriasis, hepatic cirrhosis, diabetes, atherosclerosis, angiogenesis, restinosis, ocular diseases, rheumatoid arthritis and other inflammatory disorders, autoimmune disease, and a variety of renal disorders.

In certain embodiments, the conditions, diseases and/or disorders that are affected using compounds of Formula I and compositions comprising such compounds include, but are not limited to, psoriasis, angiogenesis, cancer (for example, chronic myelogenous leukemia, gastrointestinal stromal tumors, non-small cell lung cancer, breast cancer, ovarian cancer, recurrent ovarian cancer, prostate cancer such as hormonal refractory prostate cancer, kidney cancer, head and neck cancer, or colorectal cancer), immunoregulation (graft rejection), atherosclerosis, rheumatoid arthritis, Parkinson's disease, Alzheimer's disease, diabetes (for example insulin resistance or diabetic retinopathy), septic shock, and the like.

Because kinases play an active role in angiogenesis certain compounds described herein can be useful for modulating angiogenesis. Angiogenesis, the formation of new blood vessels from preexisting ones, plays a critical role in many pathological settings, including cancer, chronic inflammation, diabetic retinopathy and macular degeneration. Angiogenesis is regulated by multiple cell-signaling pathways, including pathways controlled by cellular kinases. Blocking angiogenesis, through the modulation of cell kinases, therefore, represents an effective approach to the treatment of diseases such as cancer. Thus methods of treatment include administering a sufficient amount of a compound of Formula I to decrease the symptoms or slow the progression of these diseases or disorders by inhibiting the rate of angiogenesis in a tissue.

Compounds described herein can be useful for treating a patient suffering from a disease or disorder responsive to Hsp90 complex modulation The Hsp90 complex or it substrate proteins have been implicated in a number of cancerous conditions. Thus Hsp90 complex inhibitors of the invention are particularly useful in the treatment of cancer, including, but not limited to, chronic myeloid leukemia, melanoma, breast, ovarian, brain, lung, thyroid, colorectal, prostate, and bladder cancer. Because of the role of Hsp90 in modulating the cellular stress response, Hsp90 inhibitors of the invention are also useful in the treatment of heart disease, stroke, and neurodegenerative diseases including multiple sclerosis, Alzheimer's dementia, and ischemic optic neuropathy. Thus methods of treatment include administering a sufficient amount of a compound of the invention to decrease the symptoms or slow the progression of these diseases or disorders.

The invention further includes methods for combination drug therapy, in which a compound of the invention is given to a patient together with one or more other active agents. Thus in one embodiment the invention provides a method of treating cancer, which comprises administering to a patient in need thereof an effective amount of a compound of Formula I together with a second active agent, which is useful for treating cancer. For example the second agent may be an antitumor agent. Treatment with the second active agent may be prior to, concomitant with, or following treatment with a compound of Formula I. In certain embodiments a compound of Formula I is combined with another active agent in a single dosage form. Suitable antitumor therapeutics that may be used in combination with a compound of Formula I include, but are not limited to chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Dosage levels of the order of from about 0.1 mg to about 140 mg per kilogram of body weight per day can be useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. In certain embodiments, a dosage regimen of 4 times daily or less is used. In certain embodiments, a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

EXAMPLES

The invention is further illustrated by the following non-limiting examples.

Example 1

1-(3-{8-[(Pyridin-4-ylmethyl)-amino]-imidazo[1,2-a]pyrazin-6-yl}-phenyl)-3-(3-trifluoromethyl-phenyl)-urea Step 1. 6,8-dibromoimidazo[1,2-a]pyrazine (3)

A mixture of bromoacetaldehyde diethyl acetal (51 grams (g)), 48% hydrobromic acid (HBr) (11 milliliters (mL)), and water (11 mL) is heated at 120° C. for 1 hour (hr). The solution is cooled, poured into a mixture of sodium bicarbonate (NaHCO₃) (60 g) and isopropyl alcohol (IPA) (200 mL), and stirred for 0.5 hr. The mixture is filtered, and the filtrate is treated with 3,5-dibromo-2-aminopyrazine (1) (33 g) and heated under reflux for 16 hr. The suspension is cooled in ice, treated with 48% HBr (3 mL) and diethyl ether (60 mL) and filtered to afford 3 (33 g) as the hydrobromide salt.

Step 2. (6-Bromo-imidazo[1,2-a]pyrazin-8-yl)-pyridin-4-ylmethyl-amine (4)

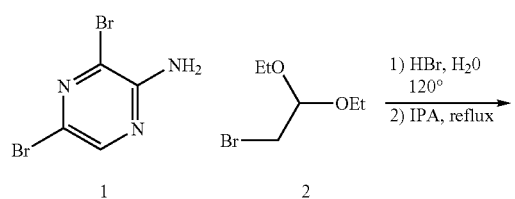

A solution of 6,8-Dibromo-imidazo[1,2-a]pyrazine 3 (1.0 equiv.), 4-aminomethylpyridine (1.0 equiv.) and potassium carbonate (3.0 equiv.) is dissolved in 20 ml 3:1 acetonitrile: dimethylacetamide and is stirred at 100° C. for 16 hours. The mixture is cooled to RT and partitioned between ethyl acetate (EtOAc) and saturated NaHCO₃. The aqueous phase is extracted with EtOAc and combined extracts are dried over Na₂SO₄. The solvent is removed under reduced pressure and the resulting residue is purified by flash chromatography (EtOAc) to yield (6-Bromo-imidazo[1,2-a]pyrazin-8-yl)-pyridin-4-ylmethyl-amine 4.

Step 3. [6-(3-Amino-phenyl)-imidazo[1,2-a]pyrazin-8-yl]-pyridin-4-ylmethyl-amine (5)

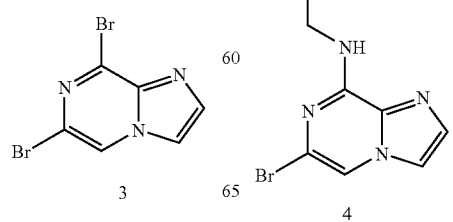

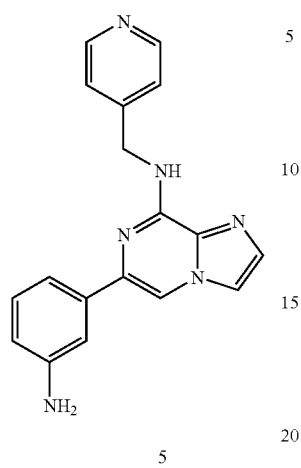

5

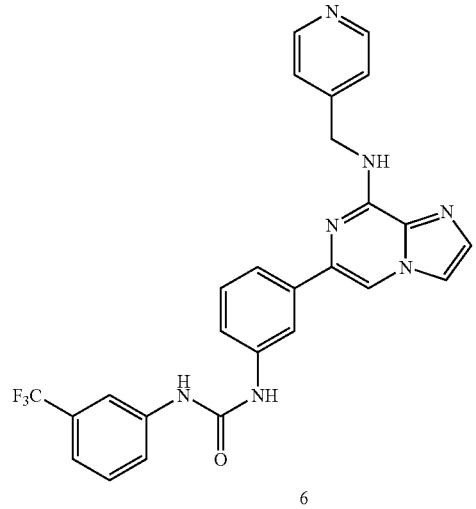

6

A mixture of (6-Bromo-imidazo[1,2-a]pyrazin-8-yl)-pyridin-4-ylmethyl-amine 4 (1.0 equiv.), 3-aminophenyl boronic acid (1.1 equiv.), Pd (PPh$_3$)$_4$ (0.10 equiv.), and K$_3$PO$_4$ (2.20 equiv.) in 4:1 1,4-dioxane:water is heated to 90° C. for 24 hr. The mixture is cooled to RT and partitioned between EtOAc and sat. NaHCO$_3$. The aqueous phase is extracted with EtOAc and combined extracts are dried over Na$_2$SO$_4$. The solvent is removed under reduced pressure and the resulting residue is purified by flash chromatography (EtOAc) to yield [6-(3-Amino-phenyl)-imidazo[1,2-a]pyrazin-8-yl]-pyridin-4-ylmethyl-amine 5.

Step 4. 1-(3-{8-[(Pyridin-4-ylmethyl)-amino]-imidazo[1,2-a]pyrazin-6-yl}-phenyl)-3-(3trifluoromethyl-phenyl)-urea (6)

A mixture of 1.00 eq. of [6-(3-Amino-phenyl)-imidazo[1,2-a]pyrazin-8-yl]-pyridin-4-ylmethyl-amine (5) and 1.00 eq. of 3-trifluoromethylphenyl isocyanate in toluene is stirred at room temperature for 24 hrs. The mixture is partitioned between EtOAc and saturated NaHCO$_3$. The aqueous phase is extracted with EtOAc and the combined extracts are dried over Na$_2$SO$_4$. The solvent is removed under reduced pressure and the resulting residue is purified by flash chromatography (EtOAc) to yield 1-(3-{8-[(Pyridin-4-ylmethyl)-amino]-imidazo[1,2-a]pyrazin-6-yl}-phenyl)-3-(3-trifluoromethyl-phenyl)-urea 6. MF=C$_{26}$H$_{20}$F$_3$N$_7$O, MW=503.48; Mass Spec m/z (M$^+$+1) 504.17.

Example 2

SYNTHESIS OF 8-O-SUBSTITUTED-6-ARYL-IMIDAZO[1,2-A]PYRAZINES

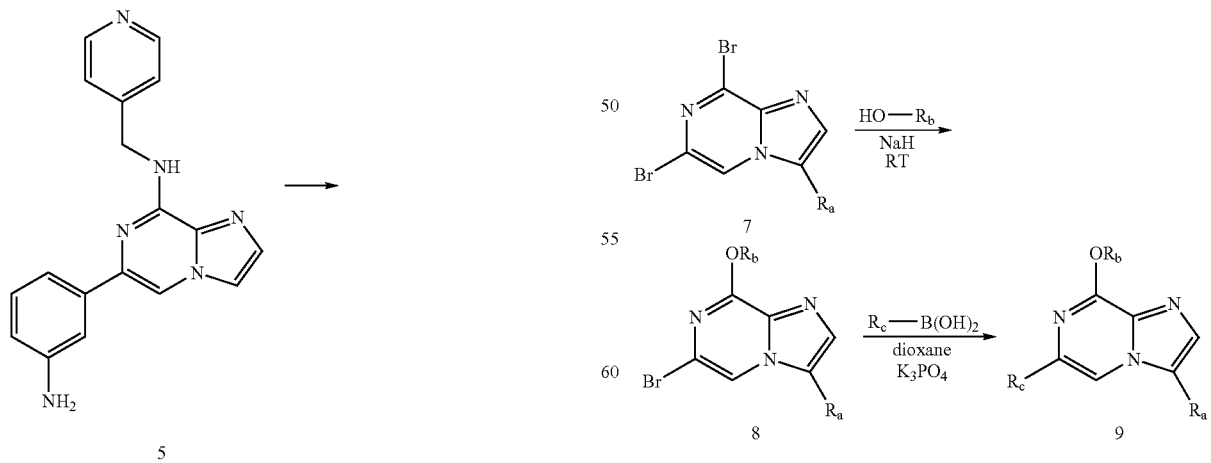

Step 2. Preparation of 8-0-Substituted-6-bromo-imidazo[1,2-a]pyrazine (8)

Procedure 1: A solution of 1.00 eq. of 6,8-dibromo-imidazo[1,2-a]pyrazine 7 (prepared in the same manner as compound 3) in N,N-dimethylformamide is added to a preformed solution of 1.2 eq. sodium hydride and 1.0 eq. of alcohol in N,N-dimethylformamide. The resulting mixture is stirred for 2 hours and quenched by the addition of water. The suspension is filtered and washed successively with water, acetone, and ethyl ether to yield 8.

Step 3. Preparation of 8-0-Substituted-6-aryl-imidazo[1,2-a]pyrazine (9)

A mixture of 1.00 eq. of 8-O-substituted-6-bromo-imidazo[1,2-a]pyrazine, 1.1 eq. of $R_4$-substituted boronic acid, and 0.10 eq. of Pd (PPh$_3$)$_4$, 2.2 eq. of K$_3$PO$_4$ in 4:1 1,4-dioxane:water is heated to 90° C. for 24 hr. The mixture is cooled to RT and partitioned between ethyl acetate (EtOAc) and saturated NaHCO$_3$. The aqueous phase is extracted with EtOAc and combined extracts are dried over Na$_2$SO$_4$. The solvent is removed under reduced pressure and the resulting residue is purified by flash chromatography (50% EtOAc:hexanes) to yield compound 9.

Example 3

SYNTHESIS OF CERTAIN SUBSTITUTED IMIDAZO[1,2-A]PYRAZINES

Example 3a

Preparation of 1-(4-chlorophenyl)-3-(3-(8-(pyridin-4-ylmethoxy)imidazo[1,2-a]pyrazin-6-yl)phenyl) urea (11)

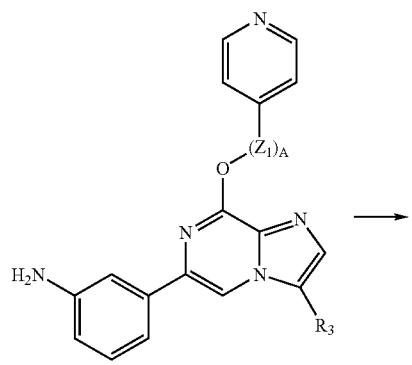

(10)

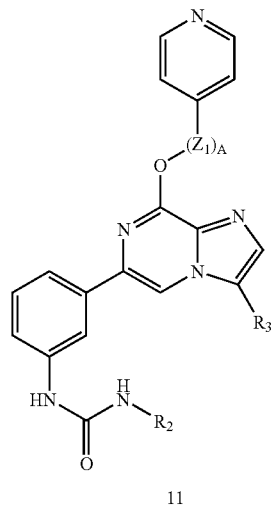

11

A mixture of 1.00 eq. of 3-(8-(pyridin-4-ylmethoxy)imidazo[1,2-a]pyrazin-6-yl)benzenamine 5, 1.00 eq. of phenyl isocyanate in toluene is stirred at room temperature for 24 hr. The mixture is partitioned between EtOAc/saturated NaHCO$_3$. The aqueous phase is extracted with EtOAc and the combined extracts are dried over Na$_2$SO$_4$. The solvent is removed under reduced pressure and the resulting residue is purified by flash chromatography (EtOAc) to yield 11.

Example 4

PREPARATION OF 4-PYRIDYLMETHOXY-IP-ANILINE

Step 1. 6-Bromo-8-(pyridin-4-ylmethoxy)-imidazo[1,2-a]pyrazine

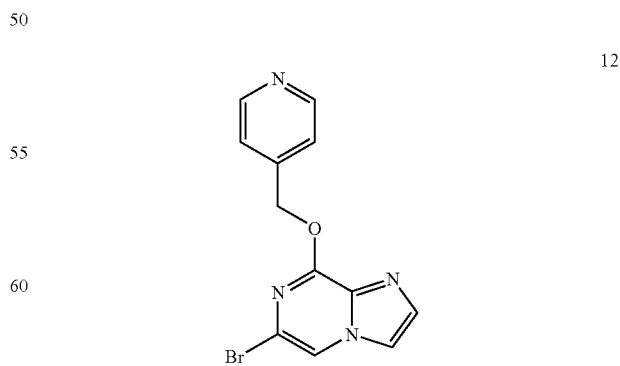

4-Pyridylcarbinol (1.84 g, 16.9 mmol) in THF (10 mL) is added to a suspension of NaH (0.81 g, 95%) in THF (40 mL) dropwise at 0 C. After 1 hour the reaction is transferred to an addition funnel and added to a solution of 6,8-dibromoimidazo[1,2-a]pyrazine (4.67 g, 16.9 mmol) in dimethylacetamide (50 mL). Once added, the reaction is run overnight at room temperature. The reaction is quenched after 16 hours by adding 100 ml water. The resultant solid is then triturated for 20 minutes and the compound filtered and washed 3 times with 100 ml water and vacuum-dried to yield 12 as a cream-colored solid.

Step 2. [6-(3-Amino-phenyl)-imidazo[1,2-a]pyrazin-8-yl]-pyridin-4-ylmethyl-amine (13)

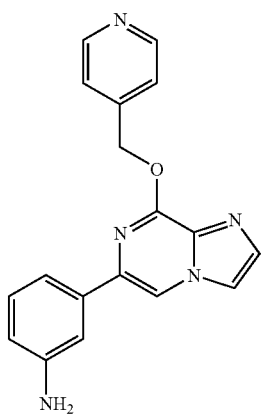

6-Bromo-8-(pyridin-4-ylmethoxy)-imidazo[1,2-a]pyrazine 8 (1.0 g, 3.29 mmol), 3-aminophenylboronic acid hemisulfate salt (673 mg, 1.1 equivs, 3.62 mmol) and potassium phosphate (2.2 equivalents, 7.24 mmol, 1.53 g dissolved in 5 mL water) and tetrakis-triphenylphosphine palladium (0.33 mmol, 380 mg) are dissolved in ethylene glycol dimethyl ether (20 ml) in a pressure vessel and heated at 95° C. with stirring. The reaction mixture is extracted after 16 hours with 150 ml ethyl acetate and washed twice with NaHCO₃ (100 ml) and once with brine (100 ml). The organic layers are dried over anhydrous sodium sulfate. The crude solution is filtered, concentrated and placed on high vacuum until the sample solidified. The solid is triturated with diethyl ether (50 ml) to yield 13 as a tan solid.

Example 5

Preparation of 1-[3-(8-{[(2-amino-ethyl)-pyridin-4-ylmethyl-amino]-methyl}-imidazo[1,2-A]pyrazin-6-YL)-phenyl]-3-(4-methoxy-3-trifluoromethyl-phenyl)-urea Step 1. (2-[(Pyridin-4-ylmethyl)-amino]-ethyl]-carbamic acid tert-butyl ester

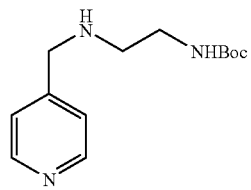

N-Boc-ethylenediamine is added in one portion to a solution of 4-pyridine carboxaldehyde (0.67 g, 6.2 mmol) in 30 mL of CH₂Cl₂. The resulting reaction mixture is stirred at RT for an hour, and NaBH(OAc)₃ (2.65 g, 12 mmol) is slowly added. Stirring continues for an additional 16 hrs. Saturated NaHCO₃ solution is then added and the desired amine is extracted using CH₂Cl₂/MeOH (3:1) mixture. Flash chromatography using 5% MeOH/CH₂Cl₂ affords the title compound 14 as a pale yellow oil.

Step 2. t2-[(6-Bromo-imidazo[1,2-a]pyrazin-8-ylmethyl)-pyridin-4-ylmethyl)-amino]-ethyl]-carbamic acid tert-butyl ester

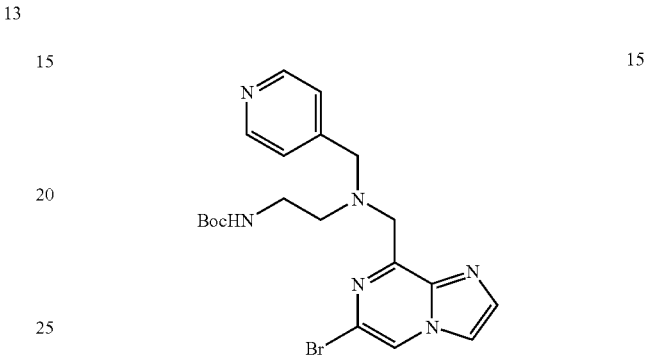

K₂CO₃ (2.3 g, 17 mmol) followed by {2-[(pyridin-4-ylmethyl)-amino]-ethyl}-carbamic acid tert-butyl ester (1.4 g, 5.6 mmol) is added to a solution of 6,8-dibromo-imidazo[1,2-a]pyrazine (1.5 g, 5.6 mmol) in 20 mL of a CH₃CN/DMA (3:1) mixture. The resulting solution is heated at 50° C. for 16 hrs, cooled to RT, and the solvent is removed under reduced pressure. The crude mixture is purified by column chromatography (30% Et₂O/EtOAc) to give the title compound 15 as an orange foam.

Step 3. (2-[[6-(3-amino-phenyl)-imidazo[1,2-a]pyrazin-8-ylmethyl]-pyridin-4-ylmethyl)-amino]-ethyl)-carbamic acid tert-butyl ester

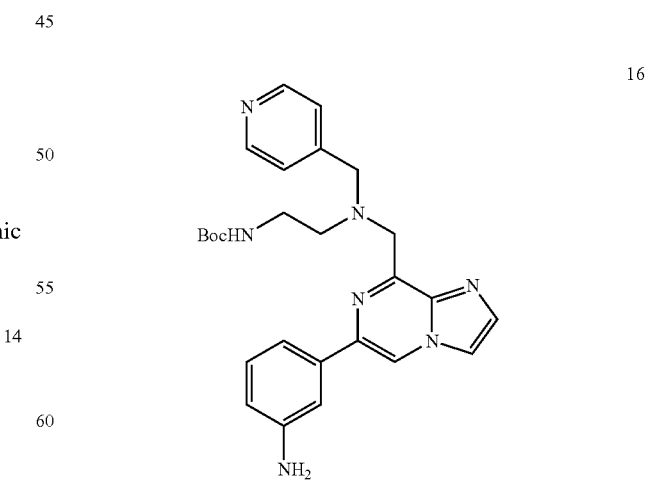

A solution of {2-[(6-bromo-imidazo[1,2-a]pyrazin-8-yl-methyl)-pyridin-4-ylmethyl)-amino]-ethyl}-carbamic acid tert-butyl ester (0.60 g, 1.3 mmol) in 8 mL of DME is added to a sealed tube, followed by Pd(PPh$_3$)$_4$ (0.16 g, 0.13 mmol) and 3-aminophenyl boronic acid hemisulfate (0.28 g, 1.5 mmol). The resulting solution is treated with a K$_3$PO$_4$ (0.63 g, 3.0 mmol) in 2 ml of water and heated at 100° C. for 16 hrs. The reaction mixture is cooled to RT, and the solvent is removed under reduced pressure. Flash chromatography with 20% acetone/CH$_2$Cl$_2$ affords the title compound 16 as an orange foam.

Step 4. (2-[6-{3-[3-(4-methoxy-3-trifluoromethyl-phenyl)-ureido]-phenyl}-imidazo[1,2-a]pyrazin-8-ylmethyl)-pyridin-4-ylmethyl)-amino]-ethyl}-carbamic acid tert-butyl ester

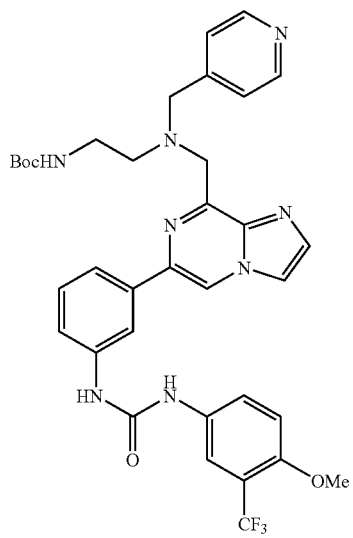

17

4-Isocyanato-1-methoxy-2-trifluoromethylbenzene (0.05 g, 0.24 mmol) in 1 mL of CH$_2$Cl$_2$ is added to a solution of (2-{[6-(3-amino-phenyl)-imidazo[1,2-a]pyrazin-8-ylmethyl]-pyridin-4-ylmethyl)-amino}-ethyl)-carbamic acid tert-butyl ester (0.11 g, 0.24 mmol) in 2 mL of CH$_2$Cl$_2$ and the resulting reaction mixture is stirred for 16 hrs. The solvent in removed under reduced pressure and the crude mixture is purified. Flash chromatography using 30% acetone/CH$_2$Cl$_2$ gives the title compound 17 as a white solid.

Step 5. 1-[3-(8-{[(2-Amino-ethyl)-pyridin-4-ylmethyl-amino]-methyl}-imidazo[1,2-a]pyrazin-6-yl)-phenyl]-3-(4-methoxy-3-trifluoromethyl-phenyl)-urea

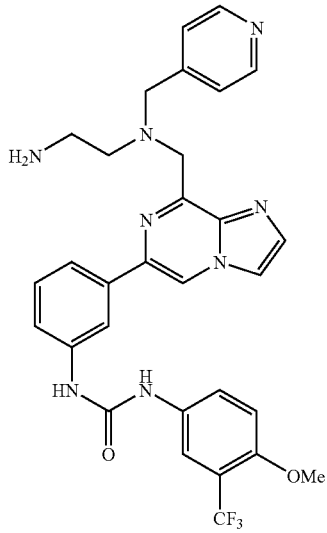

18

A solution of {2-[(6-{3-[3-(4-methoxy-3-trifluoromethyl-phenyl)-ureido]-phenyl}-imidazo[1,2-a]pyrazin-8-ylm-ethyl)-pyridin-4-ylmethyl-amino]-ethyl}-carbamic acid tert-butyl ester (0.11 g, 0.16 mmol) in 2 mL of CH$_2$Cl$_2$ is treated with HCl (0.7 mL, 1.4 mmol) and heated at 100° C. for 4 hrs. The reaction mixture is cooled to RT and the solvent is removed under reduced pressure. The bis HCl salt is recrystallized using CH$_2$Cl$_2$/Et$_2$O/Hexanes to afford the desired compound 18 as a white solid.

Example 6

Additional Compounds

The following compounds shown in TABLE I and TABLE 2 were prepared in accordance with the methods provided in Examples 1 to 5. Those of ordinary skill in the art of organic synthesis will recognize when starting materials or reaction conditions should be varied to obtain the desired compound.

MS data reported in this example was obtained as follows: MS conditions: Electrospray MS is performed on a MICRO-MASS LCT equipped with a LockSpray source for accurate mass measurements. Spectra are acquired in positive ion mode from 100-1000 Da at an acquisition rate of 1 spectrum/0.9 s with a 0.1 s interscan delay. The instrument is tuned for a resolution of 5000 (FWHM). Every 5$^{th}$ scan is taken from the reference position of the Lockspray source. Leucine enkephalin (556.2771 [M+H]$^+$) is used as the reference, or lock mass.

| Cmp. # | Structure | Name and Molecular Formula | MW | MS m/z (M+ 1) |
|---|---|---|---|---|
| 19 | 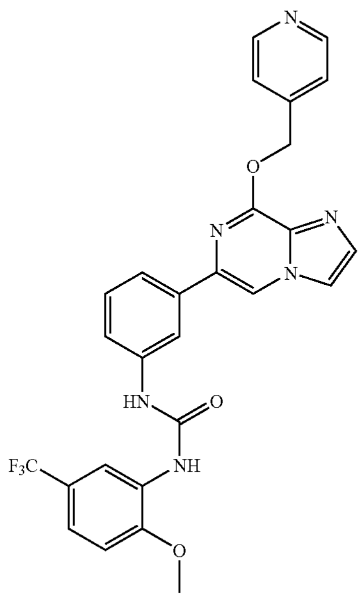 | 1-(2-Methoxy-5-trifluoromethyl-phenyl)-3-{3-[8-(pyridin-4-ylmethoxy)-imidazo[1,2-a]pyrazin-6-yl]-phenyl}-urea $C_{27}H_{21}F_3N_6O_3$ | 534.16 | 535.17 |
| 20 | 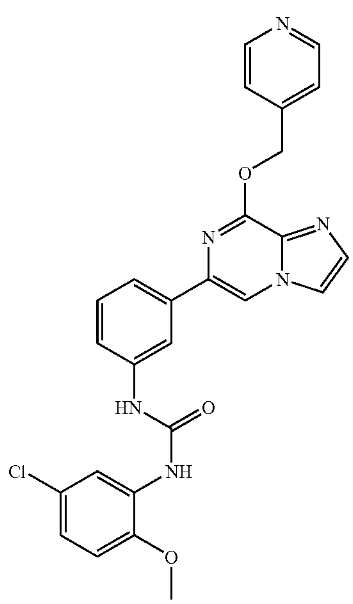 | 1-(5-Chloro-2-methoxy-phenyl)-3-{3-[8-(pyridin-4-ylmethoxy)-imidazo[1,2-a]pyrazin-6-yl]-phenyl}-urea $C_{26}H_{21}ClN_6O_3$ | 500.13 | 501.31 |

| Cmp. # | Structure | Name and Molecular Formula | MW | MS m/z (M+ 1) |
|---|---|---|---|---|
| 21 | 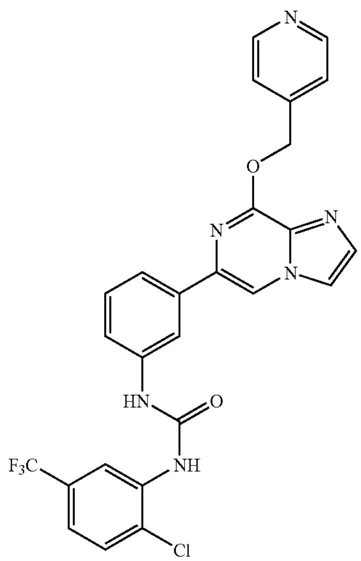 | 1-(2-Chloro-5-trifluoromethyl-phenyl)-3-{3-[8-(pyridin-4-ylmethoxy)-imidazo[1,2-a]pyrazin-6-yl]-phenyl}-urea | 538.11 | 539.28 |
| 22 | 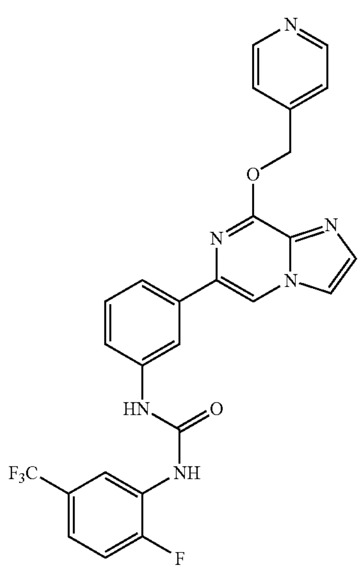 | 1-(2-Fluoro-5-trifluoromethyl-phenyl)-3-{3-[8-(pyridin-4-ylmethoxy)-imidazo[1,2-a]pyrazin-6-yl]-phenyl}-urea $C_{26}H_{18}F_4N_6O_2$ | 522.14 | 523.32 |

| Cmp. # | Structure | Name and Molecular Formula | MW | MS m/z (M+ 1) |
|---|---|---|---|---|
| 23 | 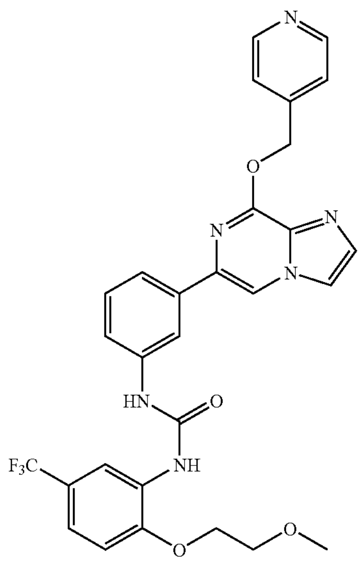 | 1-[2-(2-Methoxy-ethoxy)-5-trifluoromethyl-phenyl]-3-{3-[8-(pyridin-4-ylmethoxy)-imidazo[1,2-a]pyrazin-6-yl]-phenyl}-urea<br>$C_{29}H_{25}F_3N_6O_4$ | 578.19 | 579.26 |
| 24 | 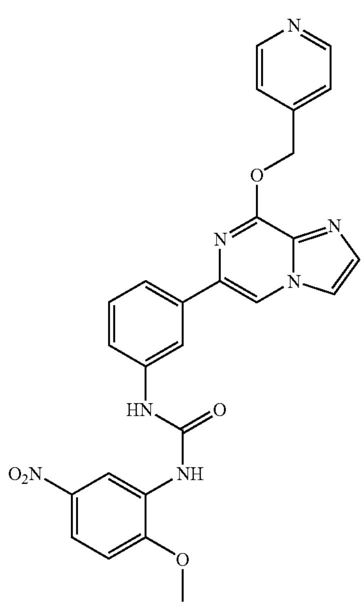 | 1-(2-Methoxy-5-nitro-phenyl)-3-{3-[8-(pyridin-4-ylmethoxy)-imidazo[1,2-a]pyrazin-6-yl]-phenyl}-urea<br>$C_{26}H_{21}N_7O_5$ | 511.16 | 512.23 |

| Cmp. # | Structure | Name and Molecular Formula | MW | MS m/z (M+ 1) |
|---|---|---|---|---|
| 25 | 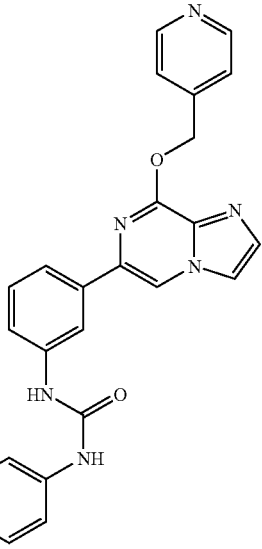 | 1-{3-[8-(Pyridin-4-ylmethoxy)-imidazo[1,2-a]pyrazin-6-yl]-phenyl}-3-(3-trifluoromethyl-phenyl)-urea<br>$C_{26}H_{19}F_3N_6O_2$ | 504.15 | 505.20 |
| 26 | 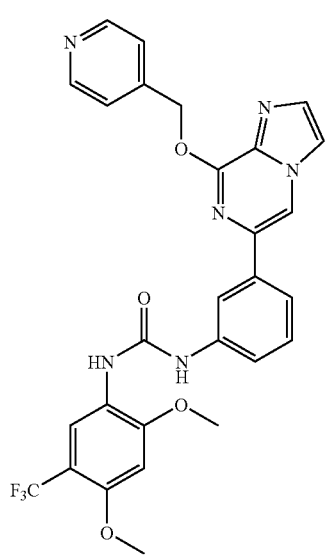 | 1-(2,4-Dimethoxy-5-trifluoromethyl-phenyl)-3-{3-[8-(pyridin-4-ylmethoxy)-imidazo[1,2-a]pyrazin-6-yl]-phenyl}-urea<br>$C_{28}H_{23}F_3N_6O_4$ | 564.17 | 565.21 |

| Cmp. # | Structure | Name and Molecular Formula | MW | MS m/z (M+ 1) |
|---|---|---|---|---|
| 27 | 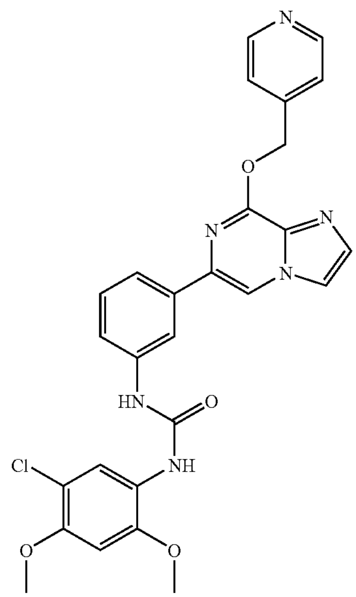 | 1-(5-Chloro-2,4-dimethoxy-phenyl)-3-{3-[8-(pyridin-4-ylmethoxy)-imidazo[1,2-a]pyrazin-6-yl]-phenyl}-urea C$_{27}$H$_{23}$ClN$_6$O$_4$ | 530.14 | 531.14 |
| 28 | 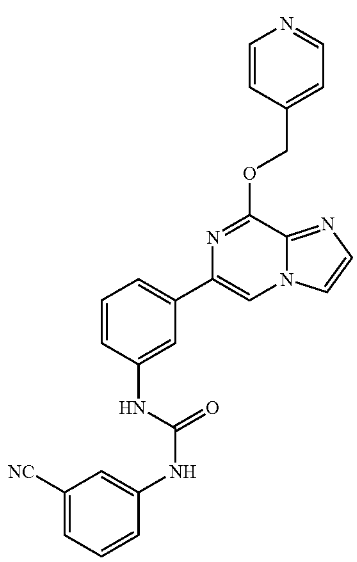 | 1-(3-Cyano-phenyl)-3-{3-[8-(pyridin-4-ylmethoxy)-imidazo[1,2-a]pyrazin-6-yl]-phenyl}-urea C$_{26}$H$_{19}$N$_7$O$_2$ | 461.16 | 462.10 |

| Cmp. # | Structure | Name and Molecular Formula | MW | MS m/z (M+ 1) |
|---|---|---|---|---|
| 29 | 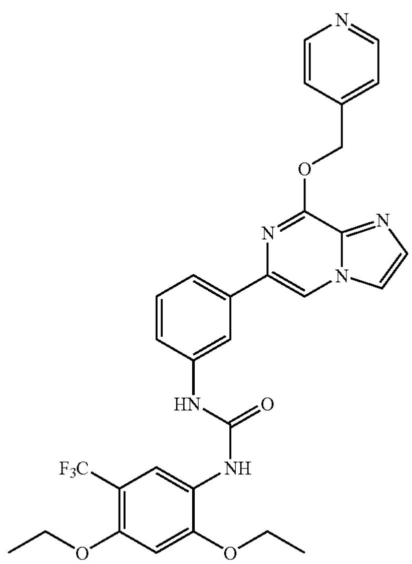 | 1-(2,4-Diethoxy-5-trifluoromethyl-phenyl)-3-{3-[8-(pyridin-4-ylmethoxy)-imidazo[1,2-a]pyrazin-6-yl]-phenyl}-urea $C_{30}H_{27}F_3N_6O_4$ | 592.20 | 593.17 |
| 30 | 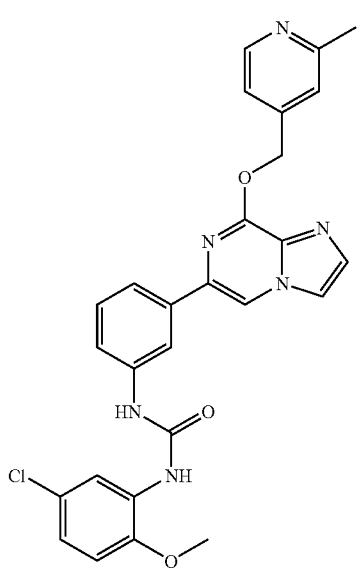 | 1-(5-Chloro-2-methoxy-phenyl)-3-{3-[8-(2-methyl-pyridin-4-ylmethoxy)-imidazo[1,2-a]pyrazin-6-yl]-phenyl}-urea $C_{27}H_{23}ClN_6O_3$ | 514.15 | 515.05 |

-continued
| Cmp. # | Structure | Name and Molecular Formula | MW | MS m/z (M+ 1) |
|---|---|---|---|---|
| 31 | 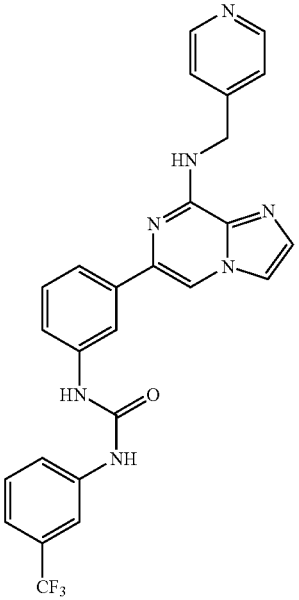 | 1-(3-{8-[(Pyridin-4-ylmethyl)-amino]-imidazo[1,2-a]pyrazin-6-yl}-phenyl)-3-(3-trifluoromethyl-phenyl)-urea<br>$C_{26}H_{20}F_3N_7O$ | 503.17 | 504.17 |
| 32 | 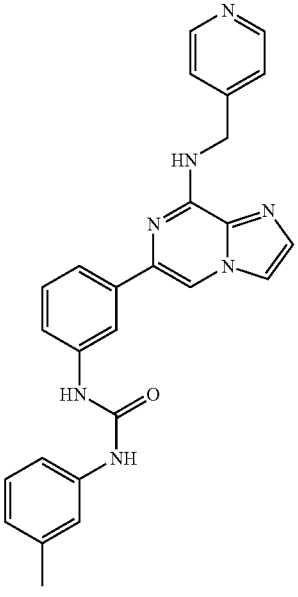 | 1-(3-{8-[(Pyridin-4-ylmethyl)-amino]-imidazo[1,2-a]pyrazin-6-yl}-phenyl)-3-m-tolyl-urea<br>$C_{26}H_{23}N_7O$ | 449.2 | 450.34 |

-continued

| Cmp. # | Structure | Name and Molecular Formula | MW | MS m/z (M+ 1) |
|---|---|---|---|---|
| 33 | 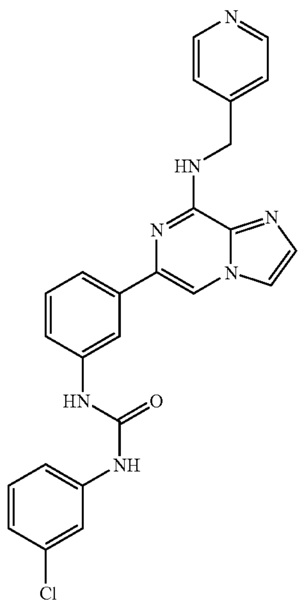 | 1-(3-Chloro-phenyl)-3-(3-{8-[(pyridin-4-ylmethyl)-amino]-imidazo[1,2-a]pyrazin-6-yl}-phenyl)-urea<br>$C_{25}H_{20}ClN_7O$ | 469.14 | 470.23 |
| 34 | 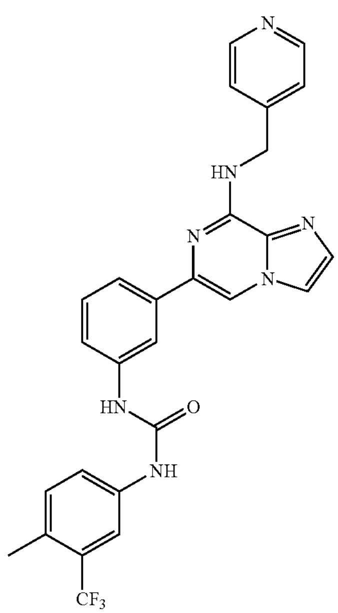 | 1-(4-Methyl-3-trifluoromethyl-phenyl)-3-(3-{8-[(pyridin-4-ylmethyl)-amino]-imidazo[1,2-a]pyrazin-6-yl}-phenyl)-urea<br>$C_{27}H_{22}F_3N_7O$ | 517.18 | 518.32 |

-continued

| Cmp. # | Structure | Name and Molecular Formula | MW | MS m/z (M+ 1) |
|---|---|---|---|---|
| 35 | 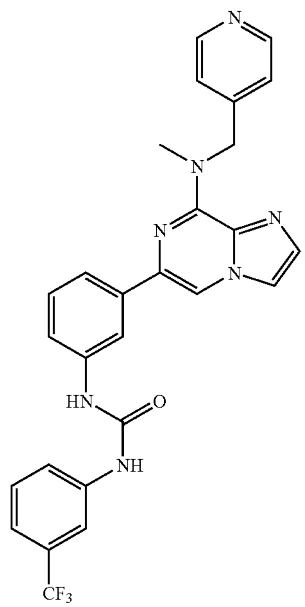 | 1-{3-[8-(Methyl-pyridin-4-ylmethyl-amino)-imidazo[1,2-a]pyrazin-6-yl]-phenyl}-3-(3-trifluoromethyl-phenyl)-urea $C_{27}H_{22}F_3N_7O$ | 517.18 | 518.34 |
| 36 | 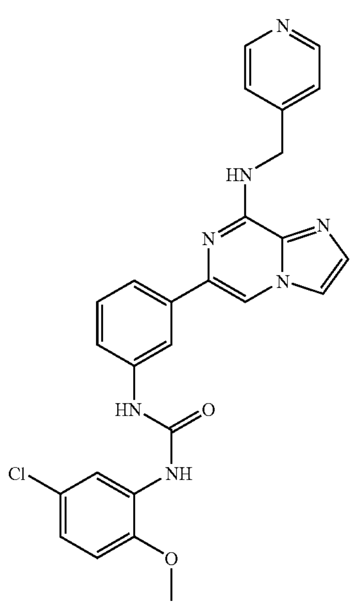 | 1-(5-Chloro-2-methoxy-phenyl)-3-(3-{8-[(pyridin-4-ylmethyl)-amino]-imidazo[1,2-a]pyrazin-6-yl}-phenyl)-urea $C_{26}H_{22}ClN_7O_2$ | 499.15 | 500.32 |

-continued

| Cmp. # | Structure | Name and Molecular Formula | MW | MS m/z (M⁺ 1) |
|---|---|---|---|---|
| 37 | 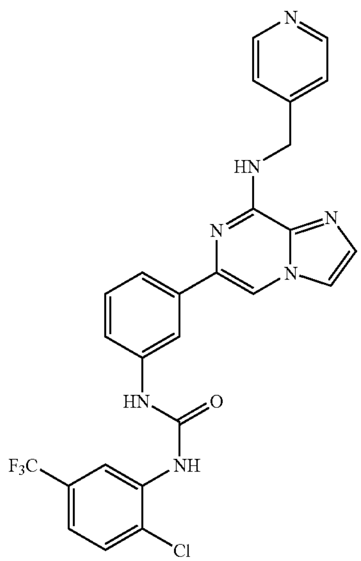 | 1-(2-Chloro-5-trifluoromethyl-phenyl)-3-(3-{8-[(pyridin-4-ylmethyl)-amino]-imidazo[1,2-a]pyrazin-6-yl}-phenyl)-urea $C_{26}H_{19}ClF_3N_7O$ | 537.13 | 538.29 |
| 38 | 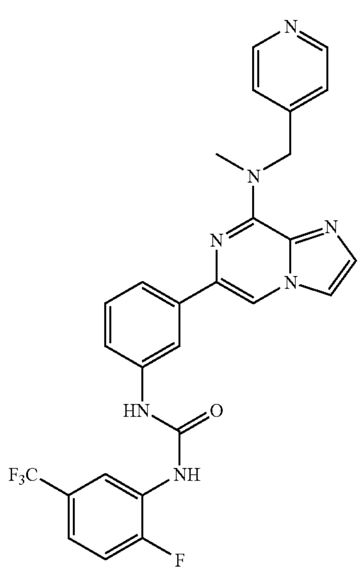 | 1-(2-Fluoro-5-trifluoromethyl-phenyl)-3-{3-[8-(methyl-pyridin-4-ylmethyl-amino)-imidazo[1,2-a]pyrazin-6-yl]-phenyl}-urea $C_{27}H_{21}F_4N_7O$ | 535.17 | 536.26 |

-continued

| Cmp. # | Structure | Name and Molecular Formula | MW | MS m/z (M+ 1) |
|---|---|---|---|---|
| 39 | 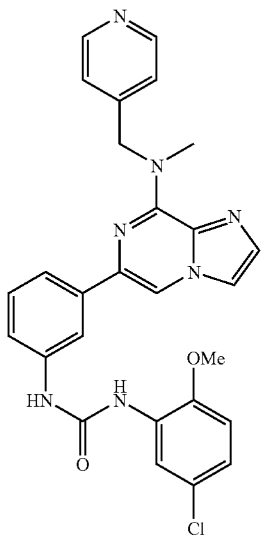 | 1-(5-Chloro-2-methoxy-phenyl)-3-{3-[8-(methyl-pyridin-4-ylmethyl-amino)-imidazo[1,2-a]pyrazin-6-yl]-phenyl}-urea<br>$C_{27}H_{24}ClN_7O_2$ | 513.17 | 514.28 |
| 40 | 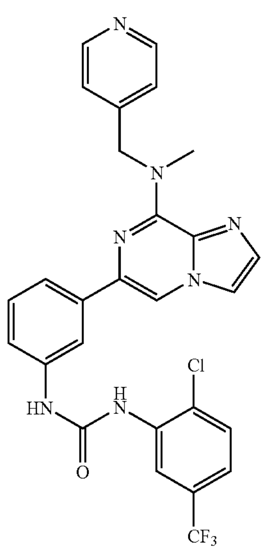 | 1-(2-Chloro-5-trifluoromethyl-phenyl)-3-{3-[8-(methyl-pyridin-4-ylmethyl-amino)-imidazo[1,2-a]pyrazin-6-yl]-phenyl}-urea<br>$C_{27}H_{21}ClF_3N_7O$ | 551.14 | 552.25 |

-continued

| Cmp. # | Structure | Name and Molecular Formula | MW | MS m/z (M+ 1) |
|---|---|---|---|---|
| 41 | 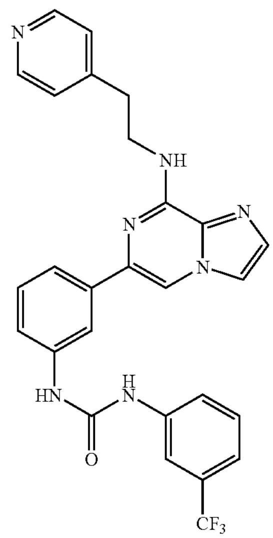 | 1-{3-[8-(2-Pyridin-4-yl-ethylamino)-imidazo[1,2-a]pyrazin-6-yl]-phenyl}-3-(3-trifluoromethyl-phenyl)-urea $C_{27}H_{22}F_3N_7O$ | 517.18 | 518.32 |
| 42 | 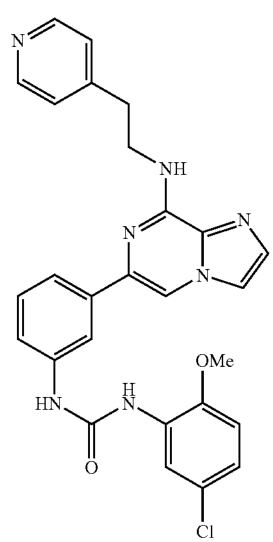 | 1-(5-Chloro-2-methoxy-phenyl)-3-{3-[8-(2-pyridin-4-yl-ethylamino)-imidazo[1,2-a]pyrazin-6-yl]-phenyl}-urea $C_{27}H_{24}ClN_7O_2$ | 513.17 | 514.32 |

| Cmp. # | Structure | Name and Molecular Formula | MW | MS m/z (M+ 1) |
|---|---|---|---|---|
| 43 | 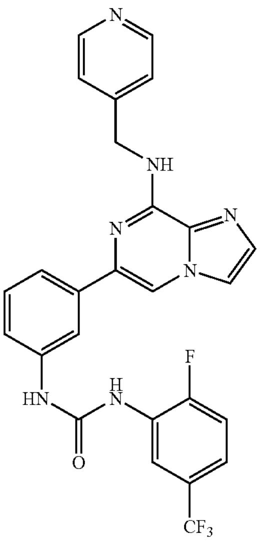 | 1-(2-Fluoro-5-trifluoromethyl-phenyl)-3-(3-{8-[(pyridin-4-ylmethyl)-amino]-imidazo[1,2-a]pyrazin-6-yl]-phenyl)-urea C$_{26}$H$_{19}$F$_4$N$_7$O | 521.16 | 522.26 |
| 44 | 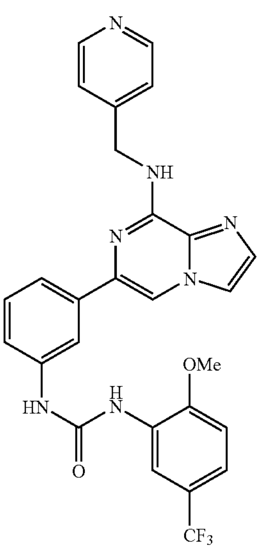 | 1-(2-Methoxy-5-trifluoromethyl-phenyl)-3-(3-{8-[(pyridin-4-ylmethyl)-amino]-imidazo[1,2-a]pyrazin-6-yl}-phenyl)-urea C$_{27}$H$_{22}$F$_3$N$_7$O$_2$ | 533.18 | 534.19 |

-continued

| Cmp. # | Structure | Name and Molecular Formula | MW | MS m/z (M+ 1) |
|---|---|---|---|---|
| 45 | 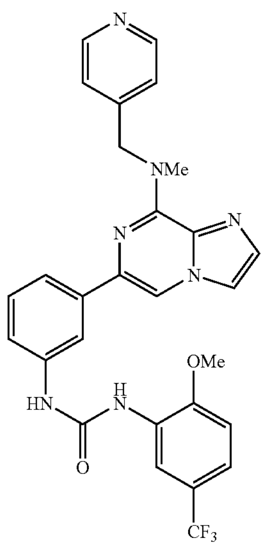 | 1-(2-Methoxy-5-trifluoromethyl-phenyl)-3-{3-[8-(methyl-pyridin-4-ylmethyl-amino)-imidazo[1,2-a]pyrazin-6-yl]-phenyl}-urea $C_{28}H_{24}F_3N_7O_2$ | 547.19 | 548.17 |
| 46 | 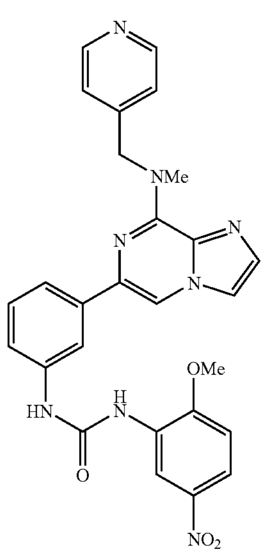 | 1-(2-Methoxy-5-nitro-phenyl)-3-{3-[8-(methyl-pyridin-4-ylmethyl-amino)-imidazo[1,2-a]pyrazin-6-yl]-phenyl}-urea $C_{27}H_{24}N_8O_4$ | 524.19 | 525.24 |

-continued

| Cmp. # | Structure | Name and Molecular Formula | MW | MS m/z (M+ 1) |
|---|---|---|---|---|
| 47 | 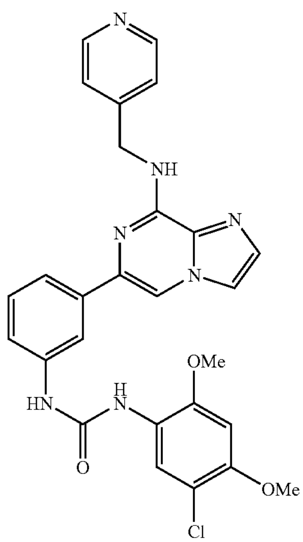 | 1-(5-Chloro-2,4-dimethoxy-phenyl)-3-(3-{8-[(pyridin-4-ylmethyl)-amino]-imidazo[1,2-a]pyrazin-6-yl}-phenyl)-urea $C_{27}H_{24}ClN_7O_3$ | 529.16 | 530.16 |
| 48 | 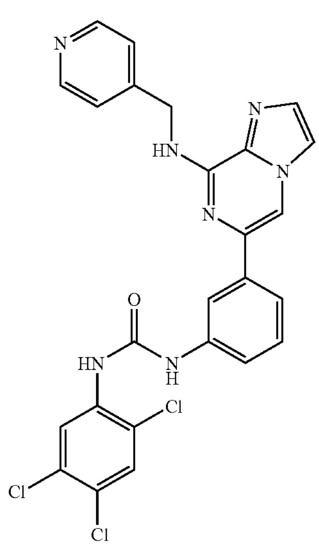 | 1-(3-{8-[(Pyridin-4-ylmethyl)-amino]-imidazo[1,2-a]pyrazin-6-yl}-phenyl)-3-(2,4,5-trichloro-phenyl)-urea $C_{25}H_{18}Cl_3N_7O$ | 537.06 | 538.07 |

-continued

| Cmp. # | Structure | Name and Molecular Formula | MW | MS m/z (M+ 1) |
|---|---|---|---|---|
| 49 | 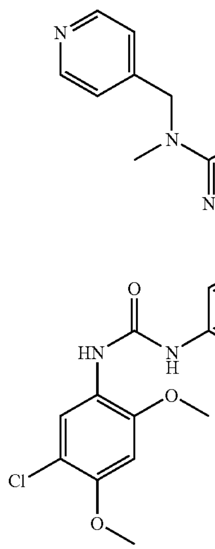 | 1-(5-Chloro-2,4-dimethoxy-phenyl)-3-{3-[8-(methyl-pyridin-4-ylmethyl-amino)-imidazo[1,2-a]pyrazin-6-yl]-phenyl}-urea $C_{28}H_{26}ClN_7O_3$ | 543.18 | 544.15 |
| 50 | 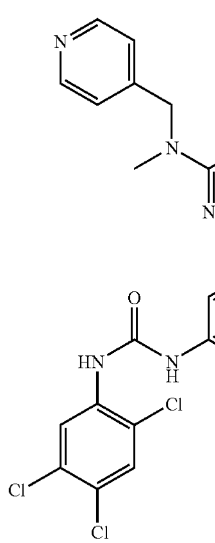 | 1-{3-[8-(Methyl-pyridin-4-ylmethyl-amino)-imidazo[1,2-a]pyrazin-6-yl]-phenyl}-3-(2,4,5-trichloro-phenyl)-urea $C_{26}H_{20}Cl_3N_7O$ | 551.08 | 552.06 |

| Cmp. # | Structure | Name and Molecular Formula | MW | MS m/z (M+ 1) |
|---|---|---|---|---|
| 51 | 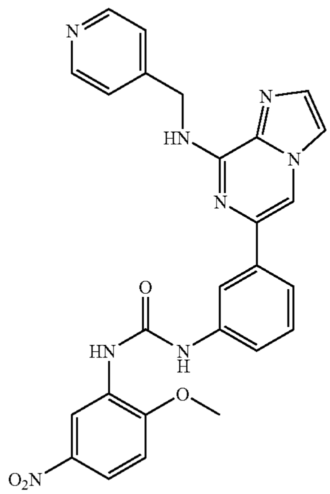 | 1-(2-Methoxy-5-nitro-phenyl)-3-(3-{8-[(pyridin-4-ylmethyl)-amino]-imidazo[1,2-a]pyrazin-6-yl}-phenyl)-urea C₂₆H₂₂N₈O₄ | 510.18 | 511.2 |
| 52 | 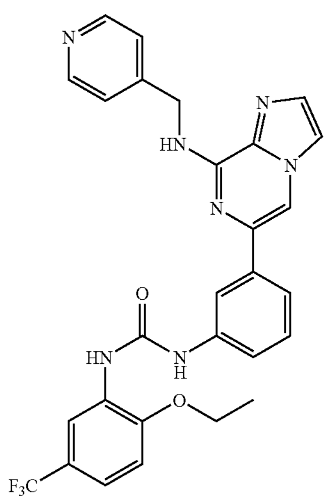 | 1-(2-Ethoxy-5-trifluoromethyl-phenyl)-3-(3-{8-[(pyridin-4-ylmethyl)-amino]-imidazo[1,2-a]pyrazin-6-yl}-phenyl)-urea C₂₈H₂₄F₃N₇O₂ | 547.19 | 548.27 |
| 53 | 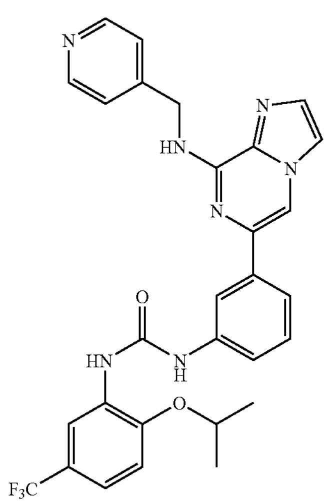 | 1-(2-Isopropoxy-5-trifluoromethyl-phenyl)-3-(3-{8-[(pyridin-4-ylmethyl)-amino]-imidazo[1,2-a]pyrazin-6-yl}-phenyl)-urea C₂₉H₂₆F₃N₇O₂ | 561.21 | 562.37 |

-continued

| Cmp. # | Structure | Name and Molecular Formula | MW | MS m/z (M+ 1) |
|---|---|---|---|---|
| 54 | 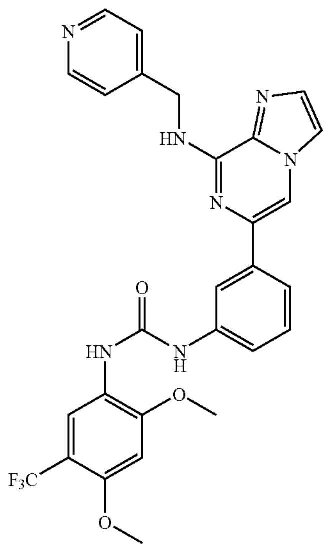 | 1-(2,4-Dimethoxy-5-trifluoromethyl-phenyl)-3-(3-{8-[(pyridin-4-ylmethyl)-amino]-imidazo[1,2-a]pyrazin-6-yl}-phenyl)-urea $C_{28}H_{24}F_3N_7O_3$ | 563.19 | 564.27 |
| 55 | 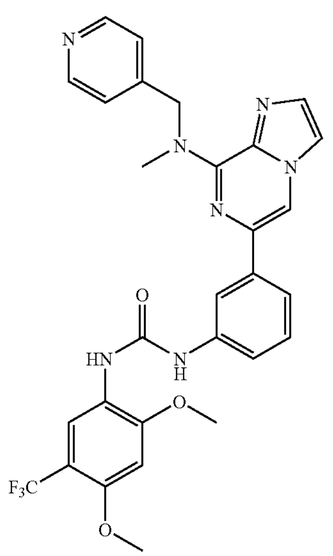 | 1-(2,4-Dimethoxy-5-trifluoromethyl-phenyl)-3-{3-[8-(methyl-pyridin-4-ylmethyl-amino)-imidazo[1,2-a]pyrazin-6-yl]-phenyl}-urea $C_{29}H_{26}F_3N_7O_3$ | 577.2 | 578.2 |

| Cmp. # | Structure | Name and Molecular Formula | MW | MS m/z (M+ 1) |
|---|---|---|---|---|
| 56 | 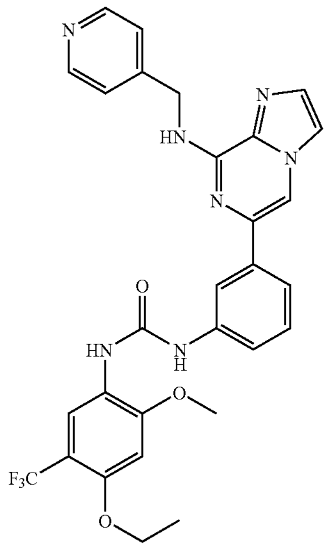 | 1-(4-Ethoxy-3-trifluoromethyl-phenyl)-3-(3-{8-[(pyridin-4-ylmethyl)-amino]-imidazo[1,2-a]pyrazin-6-yl}-phenyl)-urea $C_{28}H_{24}F_3N_7O_2$ | 547.19 | 548.14 |
| 57 | 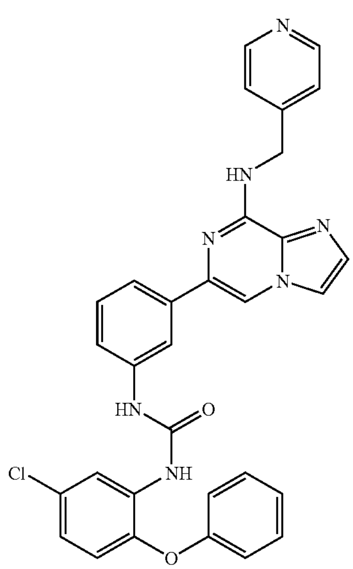 | 1-(5-Chloro-2-phenoxy-phenyl)-3-(3-{8-[(pyridin-4-ylmethyl)-amino]-imidazo[1,2-a]pyrazin-6-yl}-phenyl)-urea $C_{31}H_{24}ClN_7O_2$ | 561.17 | 562.21 |

-continued

| Cmp. # | Structure | Name and Molecular Formula | MW | MS m/z (M+ 1) |
|---|---|---|---|---|
| 58 | 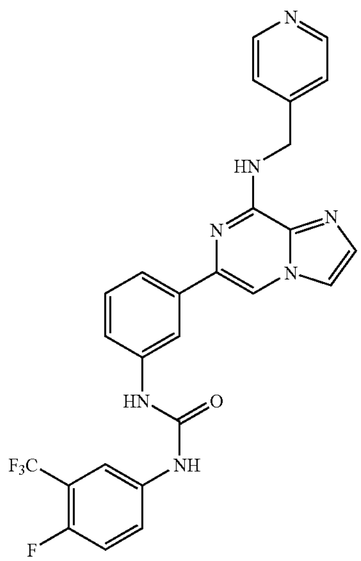 | 1-(4-Fluoro-3-trifluoromethyl-phenyl)-3-(3-{8-[(pyridin-4-ylmethyl)-amino]-imidazo[1,2-a]pyrazin-6-yl}-phenyl)-urea<br>$C_{26}H_{19}F_4N_7O$ | 521.16 | 522.17 |
| 59 | 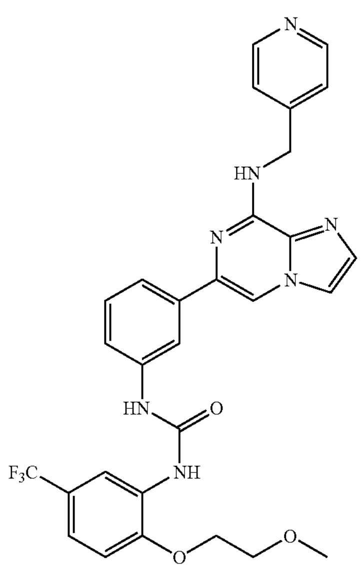 | 1-[2-(2-Methoxy-ethoxy)-5-trifluoromethyl-phenyl]-3-(3-{8-[(pyridin-4-ylmethyl)-amino]-imidazo[1,2-a]pyrazin-6-yl}-phenyl)-urea<br>$C_{29}H_{26}F_3N_7O_3$ | 577.2 | 578.34 |

| Cmp. # | Structure | Name and Molecular Formula | MW | MS m/z (M+ 1) |
|---|---|---|---|---|
| 60 | 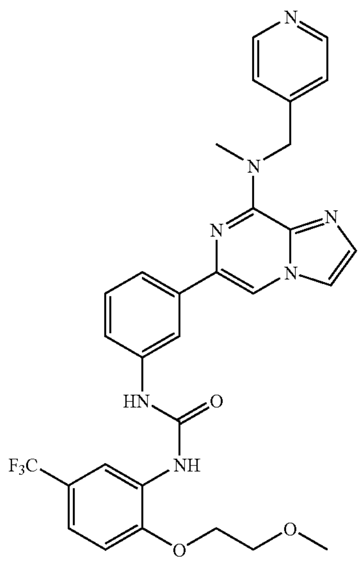 | 1-[2-(2-Methoxy-ethoxy)-5-trifluoromethyl-phenyl]-3-{3-[8-(methyl-pyridin-4-ylmethyl-amino)-imidazo[1,2-a]pyrazin-6-yl]-phenyl}-urea<br>$C_{30}H_{28}F_3N_7O_3$ | 591.22 | 592.3 |
| 61 | 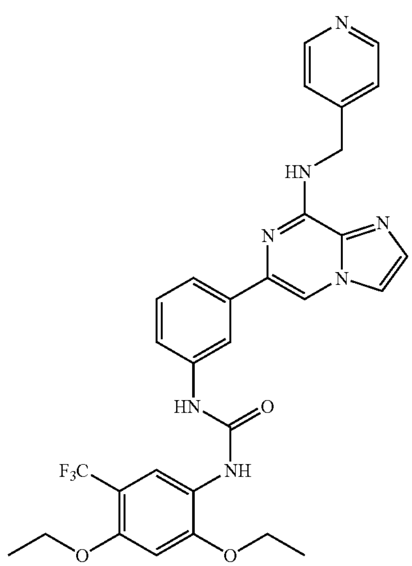 | 1-(2,4-Diethoxy-5-trifluoromethyl-phenyl)-3-(3-{8-[(pyridin-4-ylmethyl)-amino]-imidazo[1,2-a]pyrazin-6-yl}-phenyl)-urea<br>$C_{30}H_{28}F_3N_7O_3$ | 591.22 | 592.22 |

-continued

| Cmp. # | Structure | Name and Molecular Formula | MW | MS m/z (M+ 1) |
|---|---|---|---|---|
| 62 | 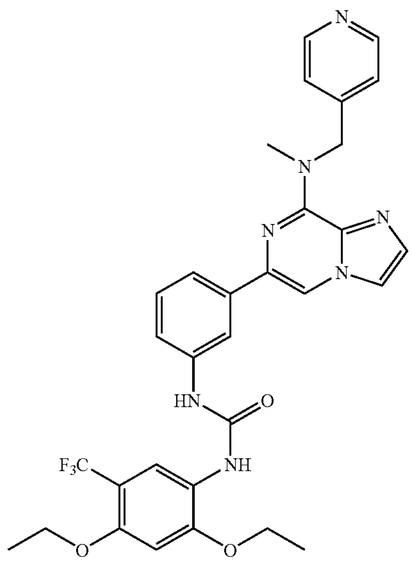 | 1-(2,4-Diethoxy-5-trifluoromethyl-phenyl)-3-{3-[8-(methyl-pyridin-4-ylmethyl-amino)-imidazo[1,2-a]pyrazin-6-yl]-phenyl}-urea $C_{31}H_{30}F_3N_7O_3$ | 605.24 | 606.23 |
| 63 | 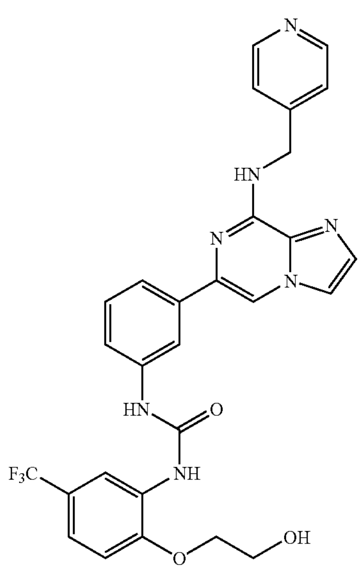 | 1-[2-(2-Hydroxy-ethoxy)-5-trifluoromethyl-phenyl]-3-(3-{8-[(pyridin-4-ylmethyl)-amino]-imidazo[1,2-a]pyrazin-6-yl}-phenyl)-urea $C_{28}H_{24}F_3N_7O_3$ | 563.19 | 564.13 |

| Cmp. # | Structure | Name and Molecular Formula | MW | MS m/z (M+ 1) |
|---|---|---|---|---|
| 64 | 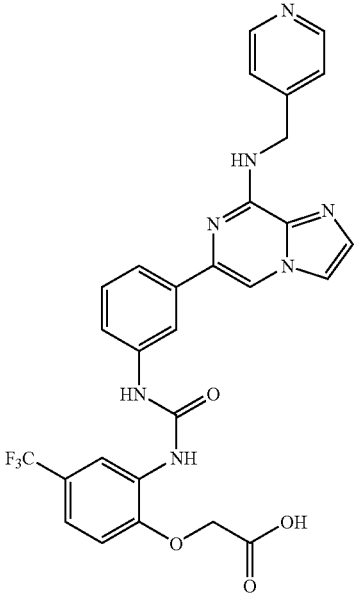 | {2-[3-(3-{8-[(Pyridin-4-ylmethyl)-amino]-imidazo[1,2-a]pyrazin-6-yl}-phenyl)-ureido]-4-trifluoromethyl-phenoxy}-acetic acid $C_{28}H_{22}F_3N_7O_4$ | 577.17 | 578.19 |
| 65 | 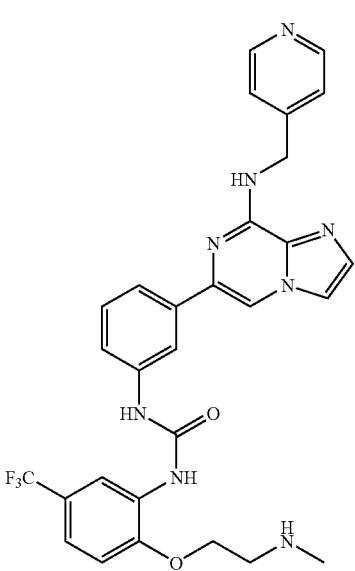 | 1-[2-(2-Methylamino-ethoxy)-5-trifluoromethyl-phenyl]-3-(3-{8-[pyridin-4-ylmethyl)-amino]-imidazo[1,2-a]pyrazin-6-yl}-phenyl)-urea $C_{29}H_{27}F_3N_8O_2$ | 576.22 | 577.25 |

| Cmp. # | Structure | Name and Molecular Formula | MW | MS m/z (M+ 1) |
|---|---|---|---|---|
| 66 | 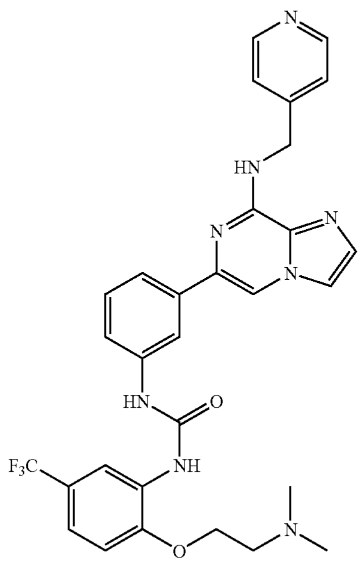 | 1-[2-(2-Dimethylamino-ethoxy)-5-trifluoromethyl-phenyl]-3-(3-{8-[(pyridin-4-ylmethyl)-amino]-imidazo[1,2-a]pyrazin-6-yl}-phenyl) urea $C_{30}H_{29}F_3N_8O_2$ | 590.24 | 591.51 |
| 67 | 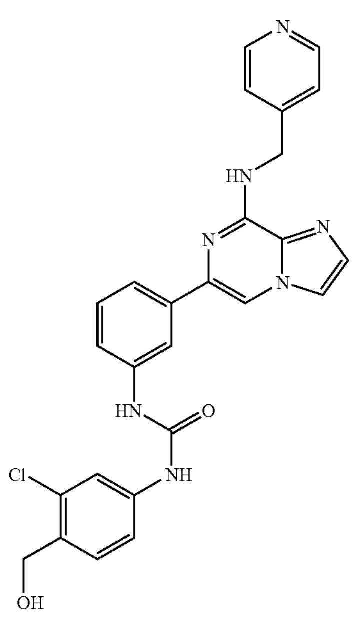 | 1-(3-Chloro-4-hydroxymethyl-phenyl)-3-(3-{8-[(pyridin-4-ylmethyl)-amino]-imidazo[1,2-a]pyrazin-6-yl}-phenyl)-urea $C_{26}H_{22}ClN_7O_2$ | 499.15 | 500.16 |

| Cmp. # | Structure | Name and Molecular Formula | MW | MS m/z (M+ 1) |
|---|---|---|---|---|
| 68 | 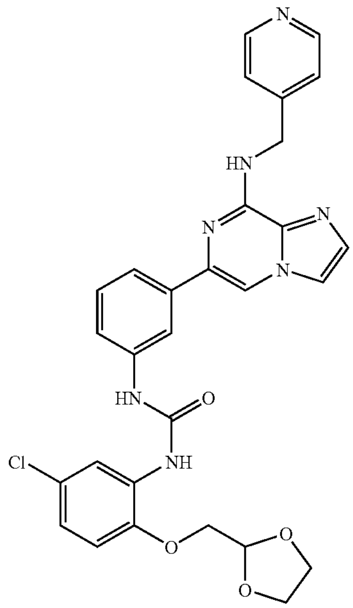 | 1-[5-Chloro-2-([1,3]dioxolan-2-ylmethoxy)-phenyl]-3-(3-{8-[(pyridin-4-ylmethyl)-amino]-imidazo[1,2-a]pyrazin-6-yl]-phenyl)-urea<br>$C_{29}H_{26}ClN_7O_4$ | 571.17 | 572.2 |
| 69 | 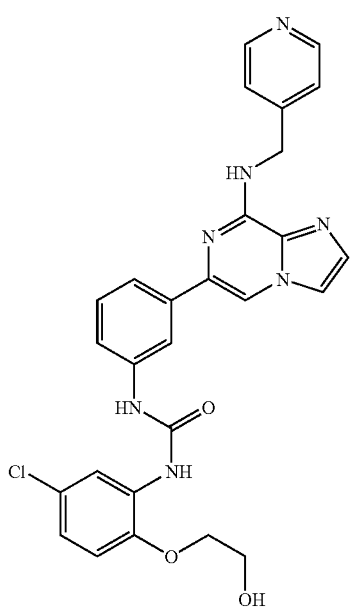 | 1-[5-Chloro-2-(2-hydroxy-ethoxy)-phenyl]-3-(3-{8-[(pyridin-4-ylmethyl)-amino]-imidazo[1,2-a]pyrazin-6-yl}-phenyl)-urea<br>$C_{27}H_{24}ClN_7O_3$ | 529.16 | 530.15 |

-continued

| Cmp. # | Structure | Name and Molecular Formula | MW | MS m/z (M+ 1) |
|---|---|---|---|---|
| 70 | 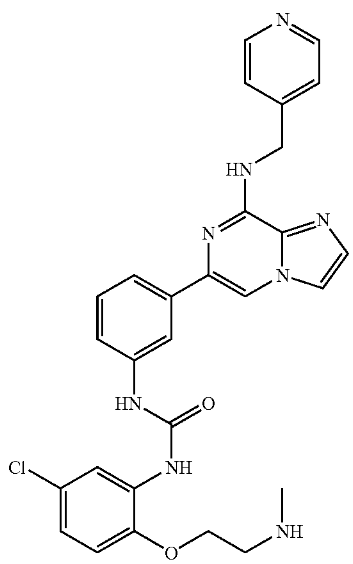 | 1-[5-Chloro-2-(2-methylamino-ethoxy)-phenyl]-3-(3-{8-[(pyridin-4-ylmethyl)-amino]-imidazo[1,2-a]pyrazin-6-yl}-phenyl)-urea<br>$C_{28}H_{27}ClN_8O_2$ | 542.19 | 543.54 |
| 71 | 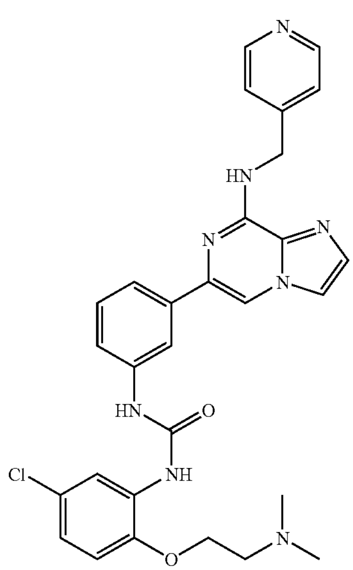 | 1-[5-Chloro-2-(2-dimethylamino-ethoxy) phenyl]-3-(3-{8-[(pyridin-4-ylmethyl)-amino]-imidazo[1,2-a]pyrazin-6-yl}-phenyl)-urea<br>$C_{29}H_{29}ClN_8O_2$ | 556.21 | 557.44 |

-continued
| Cmp. # | Structure | Name and Molecular Formula | MW | MS m/z (M+ 1) |
|---|---|---|---|---|
| 72 | 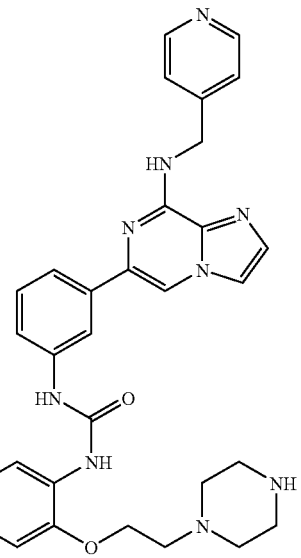 | 1-[2-(2-Piperazin-1-yl-ethoxy)-5-trifluoromethyl-phenyl]-3-(3-{8-[(pyridin-4-ylmethyl)-amino]-imidazo[1,2-a]pyrazin-6-yl}-phenyl)-urea $C_{32}H_{32}F_3N_9O_2$ | 631.26 | 632.45 |
| 73 | 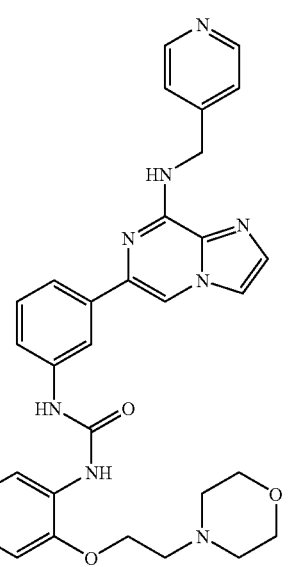 | 1-[2-(2-Morpholin-4-yl-ethoxy)-5-trifluoromethyl-phenyl]-3-(3-{8-[(pyridin-4-ylmethyl)-amino]-imidazo[1,2-a]pyrazin-6-yl}-phenyl)-urea $C_{32}H_{31}F_3N_8O_3$ | 632.24 | 633.25 |

| Cmp. # | Structure | Name and Molecular Formula | MW | MS m/z (M+ 1) |
|---|---|---|---|---|
| 74 | 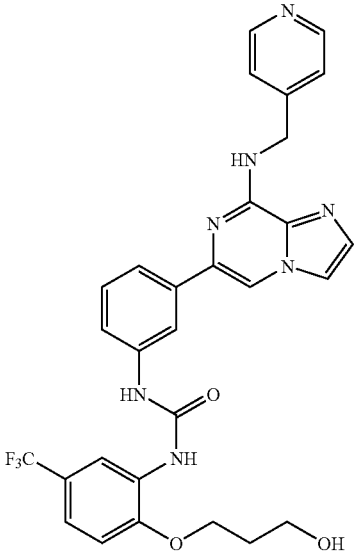 | 1-[2-(3-Hydroxy-propoxy)-5-trifluoromethyl-phenyl]-3-(3-{8-[(pyridin-4-ylmethyl)-amino]-imidazo[1,2-a]pyrazin-6-yl}-phenyl)-urea $C_{29}H_{26}F_3N_7O_3$ | 577.2 | 578.13 |
| 75 | 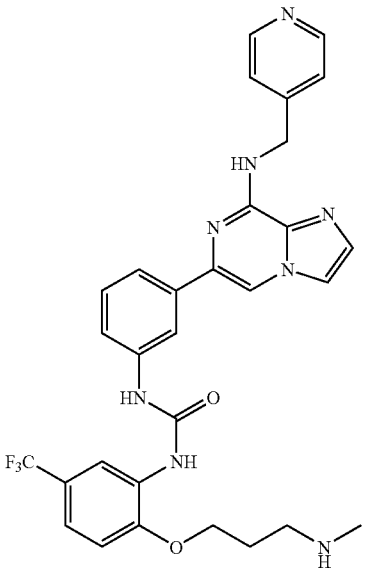 | 1-[2-(3-Methylamino-propoxy)-5-trifluoromethyl-phenyl]-3-(3-{8-[(pyridin-4-ylmethyl)-amino]-imidazo[1,2-a]pyrazin-6-yl}-phenyl)-urea $C_{30}H_{29}F_3N_8O_2$ | 590.60 | 591.13 |

| Cmp. # | Structure | Name and Molecular Formula | MW | MS m/z (M+ 1) |
|---|---|---|---|---|
| 76 | 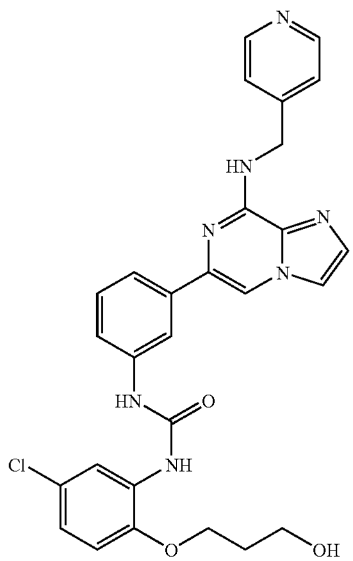 | 1-[5-Chloro-2-(3-hydroxy-propoxy)-phenyl]-3-(3-{8-[(pyridin-4-ylmethyl)-amino]-imidazo[1,2-a]pyrazin-6-yl}-phenyl)-urea<br>C$_{28}$H$_{26}$ClN$_7$O$_3$ | 543.18 | 544.14 |
| 77 | 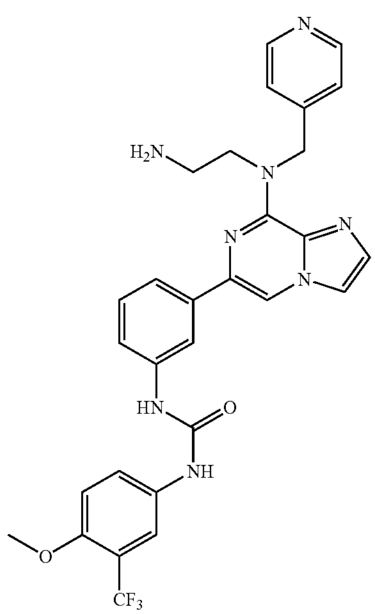 | 1-(3-{8-[(2-Amino-ethyl)-pyridin-4-ylmethyl-amino]-imidazo[1,2-a]pyrazin-6-yl}-phenyl)-3-(4-methoxy-3-trifluoromethyl-phenyl)-urea<br>C$_{29}$H$_{27}$F$_3$N$_8$O$_2$ | 576.22 | 577.17 |

| Cmp. # | Structure | Name and Molecular Formula | MW | MS m/z (M+ 1) |
|---|---|---|---|---|
| 78 | 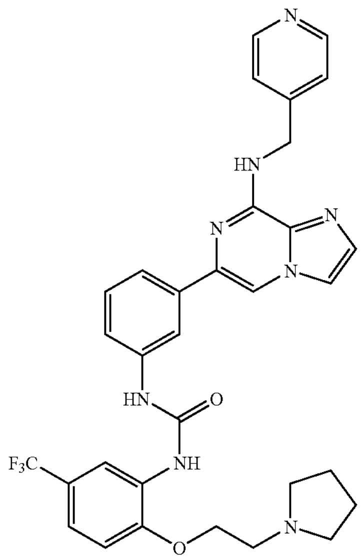 | 1-(3-{8-[(Pyridin-4-ylmethyl)-amino]-imidazo[1,2-a]pyrazin-6-yl}-phenyl)-3-[2-(2-pyrrolidin-1-yl-ethoxy)-5-trifluoromethyl-phenyl]-urea  $C_{32}H_{31}F_3N_8O_2$ | 616.64 | 617.13 |
| 79 | 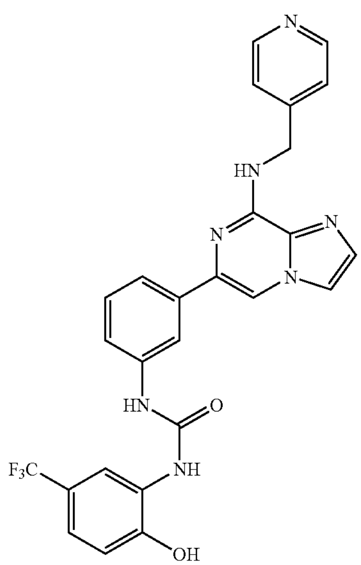 | 1-(2-Hydroxy-5-trifluoromethyl-phenyl)-3-(3-{8-(pyridin-4-ylmethyl)-amino]-imidazo[1,2-a]pyrazin-6-yl}-phenyl)-urea  $C_{26}H_{20}F_3N_7O_2$ | 519.48 | 520.09 |

Example 7

Assay for EPHB$_4$ Kinase Activity

The following is a procedure for a standard biochemical assay for EphB$_4$ Kinase Activity Materials:

96-well, ½ area flat bottom, white polystyrene plates are purchased from Costar, cat #3693.

The cytoplasmic domain of recombinant EphB$_4$ kinase (amino acids 596-987, *Homo sapiens* EphB$_4$, GENBANK Accession No. AY056047.1) with a C-terminal V5-(his)$_6$ tag is purified from Sf9 cells. Purity of >95% is assessed by Sypro-Ruby staining of SDS gels.

PTK Biotinylated Peptide Substrate 2, is purchased from Promega, cat #V288A.

LANCE Eu-W1024 labeled anti-phosphotyrosine antibody (PT66) is purchased from Perkin-Elmer, cat #AD0068. Kinase Buffer is purchased from Cell Signaling, cat #9802.

Dilutions of compounds are made in 100% DMSO at 20× the final desired concentration. Compounds in 100% DMSO are transferred (1.25 µL) to the 96 well assay plate. A 18.75 µL volume of master mix containing the final concentrations (in 25 ul) of 0.01% BSA, 1× Cell Signaling Kinase Buffer, 0.5 µM PTK Biotinylated Peptide Substrate 2, and 60 ng/well of EphB4 kinase is added to all wells, except the four negative control wells (which contain no kinase), and mixed. To initiate the reaction, 5 µL of 550 uM ATP is added to each well. (Final Concentration of ATP=110 µM). The reactions are incubated for 1 hour at room temperature (RT). After incubation a quantity of 8.35 µL of a 4×SA-APC Detection Mix is added to each well. The final concentration of Eu-labelled PT66 antibody is 1 nM and the SA-APC is 20 nM (based on the SA moiety). The reaction plates are incubated at RT for at least 15 minutes after SA-APC Detection Mix addition. The reaction plates are read on an Envision plate reader (Perkin-Elmer) with 605 nm Excitation at 605 nm and 640 nm Emission wavelengths. Values are corrected for the fluorescence in the absence of enzyme and inhibition curves are fit to the data using a Logit curve-fitting algorithm. $IC_{50}$ values are determined from these inhibition curves.

Example 8

EPHB4 Cellular Assay

The following cell-based assay may also used to determine the effect of compounds on $EphB_4$ activity.

HEK293 cells stably expressing V5-epitope tagged $EphB_4$ are grown to ~75% confluency, and then incubated for 1 hr at 37° C. in low serum media (Optimem) containing test compound. Cells are stimulated for 10 minutes at 37° C. with 500 ng/mi $EphrinB_2$/Fc chimera and 50ng/ml goat-anti-human IgG (FC specific) in low serum media containing test compound. Cells are washed in ice-cold PBS, lysed, and protein assays are performed on the cleared lysates. Equal protein amounts of each sample are subjected to SDS-PAGE and western blotting with either an anti-phosphotyrosine antibody or an anti-V5 antibody to control for total amounts of V5-tagged $EphB_4$ in each lysate.

Example 9

PDGF-Rα Cellular Assay

The following cell-based assay may be used to determine the effect of compounds on PDGF-Rα activity.

HEK293 cells are grown to about 75% confluency in DMEM media with 10% fetal calf serum. Cells are transiently transfected with DNA encoding V5-epitope tagged, full-length PDGF-Rα using Lipofectamine reagent. After incubation for approximately 16 hrs at 37degrees, cells are incubated in low serum media (Optimem) containing test compound diluted 1:500 from a stock solution in 100% DMSO (yielding 0.2% final DMSO). To screen compounds at a range of concentrations (e.g. 10-0.01 uM), test compound is serially diluted in 100% DMSO and each of these serial dilutions is diluted 1:500 in Optimem to yield test compound in media at the desired concentration with 0.2% DMSO final. Cells are washed in ice-cold PBS, lysed, and protein assays are performed on the cleared lysates. Equal protein amounts of each sample are subjected to SDS-PAGE and western blotting with either an anti-phosphotyrosine antibody or an anti-V5 antibody to control for total amounts of V5-tagged PDGF-Rα in each lysate.

Example 10

Biochemical Assay

The following assay is a standard biochemical assay used to test activity of compounds as inhibitors of c-Kit, VEGF-R2, and Tie-2 kinase activity.

Test compounds are diluted 1:20 from an original 20 μM DMSO stock and incubated with recombinant c-Kit (10 ng), Tie-2 (6 ng), or VEGF-R2 (1 ng) enzyme (ProQinase GmbH, Germany), biotinylated peptide (PTK peptide 2, Promega) in Cell Signalling kinase buffer (c-Kit and Tie-2) or Upstate Kinase buffer (VEGF-R2) and 5 ul of ATP (final concentrations: 50 μM (50 μM for the VEGF-R2 assay, 60 μM for the Tie2 assay, and 150 μM for the c-Kit assay) for 60 minutes at room temperature. The final assay volume is 25 μl. After the 60 minute incubation Streptavidin-APC Detection Mix, which includes 1 nM LANCE Eu-W1024 labeled anti-phosphotyrosine antibody PT66 (Perkin-Elmer, cat #AD0068) and 20 nM SA-APC (based on the SA moiety), is added. The reaction plates are incubated at room temperature for at least 15 minutes after SA-APC detection mix addition. The reaction plates are then read on an Envision plate reader (Perkin-Elmer) with 605 nm excitation 615 nM and 640 nm emission wavelengths.

For a negative control, i.e. a readout in which the kinases are not inhibited, the assay is run without any test compound added. Staurosporine, a general kinase inhibitor, is used as a positive control.

$IC_{50}$ values are determined from an 11-point saturation binding curve for test compounds that show significant inhibition of one of the tyrosine kinases. In these assays concentration of test compound ranges from 10 μM to 20 nM. Equilibrium binding parameters are determined by fitting the allosteric Hill equation to the measured values with the aid of the computer program, such as FitP™ (BIOSOFT, Ferguson, Mo.).

Example 11

Western Blot

Tumor cells, such as MCF-7 or HCT-15 cells (both from ATCC, Manassas, Va.), are grown to 50-70% confluency and are subsequently incubated for 4-48 hr at 37° C. in DMEM media containing 20 μM test compound. Cells are washed in ice-cold PBS, lysed, and spun at 10,000×g for 10 minutes to removes cellular debris. Protein concentration of the cleared lysates is determined using a commercially available protein assay, such as the Piece BCA assay. Equal protein amounts, approximately 30 μl/lane are loaded onto an SDS-PAGE gel. Proteins are transferred via electrophoresis to nitrocellulose membrane for western blotting. Blots are analyzed for depletion of an HSP90 substrate protein, such as ErbB2 (Anti-ErbB2: Santa Cruz #SC-284), and increased levels of HSP70 (Anti-HSP70, Transduction Labs #610608). An antibody against a protein that is not an HSP90 client protein, such as PKA (Anti-PKA Transduction Labs #610980), is used as a loading control. Detection is via a horseradish peroxidase (HRP)-conjugated second antibody.

Example 12

Tumor Cell Monolayer Proliferation Assay:

Test compounds are diluted to 1% DMSO, final concentration, and incubated with $3\text{-}5\times10^3$ tumor cells (for example MCF-7 or HCT-15 cells) in a final volume of 200 μl for 5 days. CELLTITER 96 AQUEOUS ONE Solution Cell Proliferation Assay (Promega, Madison Wis.), a colorimetric assay for determining the number of viable cells is used to quantitate cell growth. In this method, 10-20 μl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

For saturation binding analysis cell proliferation is response to a range of test compound concentrations is determined, for example 6 or 11 test compound concentrations, from 10 μM to 20 nM may be used. Equilibrium binding parameters are determined by fitting the allosteric Hill equation to the measured values.

Example 13

Test Results

All compounds described in Example 6 were tested in the assay for EphB$_4$ activity given in Example 7, and found to exhibit an IC$_{50}$ of 1 micromolar or less. In certain embodiments, compounds disclosed in Example 6 exhibited an IC$_{50}$ of 500 nM or less in this assay. In certain embodiments, compounds exhibited an IC$_{50}$ of 100 nM or less in this assay. Certain compounds of Examples 6 were tested in the assay for PDGF-Rα activity given in Example 9, and found to exhibit an IC$_{50}$ of 500 nM or less in this assay. In certain embodiments, the compounds described in Example 6 were tested in the assay for c-Kit activity described in Example 10 and found to exhibit an IC$_{50}$ of 1 micromolar or less. In certain embodiments, these compounds exhibited an IC$_{50}$ of 500 nM or less in the assay for c-Kit activity. In certain embodiments, the compounds disclosed in Example 6 exhibited an IC$_{50}$ of 100 nM or less in this assay. Certain compounds described in Example 6 were also tested in the assay for VEGFR-2 activity given in Example 10. In certain embodiments, the compounds were found to exhibit an IC$_{50}$ of 1 micromolar or less. In certain embodiments, the compounds exhibited an IC$_{50}$ of 100 nM or less in this assay. In certain embodiments, the compounds exhibited an IC$_{50}$ of 50 nM or less in this assay. Certain compounds described in Example 6 were also tested in the assay for Tie-2 activity given in Example 10 and found to exhibit an IC$_{50}$ of about 1 micromolar or less. Certain compounds disclosed in Example 6 exhibited an IC$_{50}$ of 500 nM or less in this assay.

While certain embodiments have been shown and described, various modifications and substitutions may be made thereto without departing from the spirit and scope of the invention. Accordingly, it is to be understood that the present invention has been described by way of illustration and not limitations.

What is claimed is:
1. A compound having the Formula I

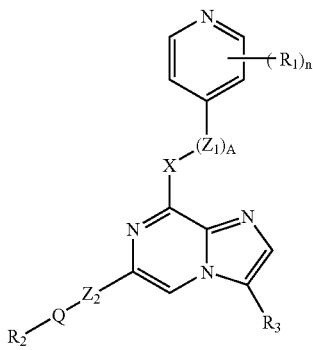

Formula I wherein:
n is 0, 1, 2, or 3;
R$_1$ is independently chosen from hydroxy, nitro, cyano, amino, amido, sulfonamido, halo, —CHO, —COOH, C$_1$-C$_6$alkyl, such as C$_3$-C$_6$cycloalkyl, C$_2$-C$_6$ alkenyl, C$_2$-C$_6$ alkynyl, C$_1$-C$_6$ alkoxy, C$_7$cycloalkyl, mono- and di(C$_1$-C$_6$ alkyl)amino, mono- and di(C$_1$-C$_6$ alkyl)amino (C$_1$-C$_6$alkyl), C$_1$-C$_6$haloalkyl, C$_1$-C$_6$haloalkoxy, (C$_1$-C$_6$alkoxy)C$_1$-C$_6$alkoxy, amino(C$_1$-C$_6$alkyl), C$_1$-C$_6$alkylthio, oxo, heteroaryl, and —(C=O)R$_{13}$ wherein R$_{13}$ is chosen from C$_1$-C$_6$ alkyl, such as C$_3$-C$_6$cycloalkyl, C$_7$cycloalkyl, C$_2$-C$_6$ alkanoyl, C$_1$-C$_6$alkoxycarbonyl, heterocycloalkyl, phenyl, and heteroaryl;

R$_3$ is chosen from hydrogen, optionally substituted C$_1$-C$_6$ alkyl, such as optionally substituted C$_3$-C$_6$cycloalkyl, optionally substituted C$_7$cycloalkyl, optionally substituted (heterocycloalkyl)C$_0$-C$_4$alkyl, and optionally substituted (heteroaryl)C$_0$-C$_4$alkyl;

A is 1, 2, 3, or 4;
Z$_1$ is —CR$_4$R$_5$— wherein each R$_4$ and R$_5$ is independently chosen from hydrogen, C$_1$-C$_6$ alkyl, and halo;
Z$_2$ is a divalent linking group chosen from para-phenylene, meta-phenylene, ortho-phenylene, and naphthylene, said divalent linking group being substituted with one group R$_2$—Q—, where
Q is

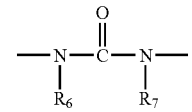

wherein R$_6$ and R$_7$ are each independently chosen from hydrogen; C$_1$-C$_6$ alkyl; optionally substituted phenyl, and optionally substituted heteroaryl;
X is O, S or —CH$_2$—; and
R$_2$ is chosen from optionally substituted C$_1$-C$_7$alkyl, such as optionally substituted C$_3$-C$_7$cycloalkyl, optionally substituted (C$_3$-C$_7$cycloalkyl)C$_1$-C$_7$ alkyl, optionally substituted heterocycloalkyl, optionally substituted (heterocycloalkyl)C$_1$-C$_2$ alkyl, optionally substituted (C$_1$-C$_6$alkoxy)C$_0$-C$_6$alkyl, optionally substituted (C$_1$-C$_6$alkoxy)C$_1$-C$_6$alkoxy, optionally substituted phenyl, and optionally substituted heteroaryl.

2. A compound of claim 1, wherein Z$_2$ is meta-phenylene substituted with
R$_2$—Q—.

3. A compound of claim 1, wherein R$_6$ and R$_7$ are each independently chosen from hydrogen and methyl.

4. A compound of claim 3, wherein R$_6$ and R$_7$ are hydrogen.

5. A compound of claim 1, wherein X is O.

6. A compound of claim 1, wherein A is 1; and R$_4$ and R$_5$ are hydrogen.

7. A compound of claim 1, wherein R$_3$ is chosen from hydrogen and C$_1$-C$_4$alkyl.

8. A compound of claim 7, wherein R$_3$ is hydrogen.

9. A compound of claim 1, wherein n is 0 and R$_1$ is absent.

10. A compound of claim 1, wherein R$_2$ is chosen from phenyl and heteroaryl, each of which is optionally substituted.

11. A compound of claim 1, wherein R$_1$ is chosen from hydroxy, cyano, halo, C$_1$-C$_2$alkyl, C$_1$-C$_2$alkoxy, C$_1$-C$_2$haloalkyl, and C$_1$-C$_2$haloalkoxy.

12. A compound of claim 11, wherein R$_1$ is chosen from halo, methyl, and methoxy.

13. A compound of claim 1 wherein
X is O, S, or CH$_2$;
n is 0, 1, 2, or 3;
each occurrence of R$_1$ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl) amino, mono- and di($C_1$-$C_6$ alkyl)amino($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl;

A is 1, 2, 3, or 4;

$Z_1$ is —$CR_4R_5$—;

each of $R_4$ and $R_5$ is independently chosen from hydrogen, $C_1$-$C_6$alkyl, and halo;

$Z_2$ is a meta-phenylene divalent linking group;

$R_6$ and $R_7$ are each independently chosen from hydrogen and methyl; and $R_2$ is chosen from phenyl and heteroaryl, each of which is optionally substituted.

14. A compound of claim 1 wherein

X is O, S, or $CH_2$;

n is 0, 1, 2, or 3;

each occurrence of $R_1$ is chosen from hydroxy, cyano, halo, $C_1$-$C_2$alkyl, $C_1$-$C_2$alkoxy, $C_1$-$C_2$haloalkyl, and $C_1$-$C_2$haloalkoxy;

A is 1;

$Z_1$ is —$CR_4R_5$—;

$R_4$ and $R_5$ are both hydrogen;

$Z_2$ is a meta-phenylene divalent linking group;

$R_6$ and $R_7$ are each independently chosen from hydrogen and methyl; and $R_2$ is chosen from phenyl and heteroaryl, each of which is optionally substituted.

15. A compound of claim 1 wherein

X is O, S, or $CH_2$;

n is 0 and $R_1$ is absent;

A is 1;

$Z_1$ is —$CR_4R_5$—;

$R_4$ and $R_5$ are both hydrogen;

$Z_2$ is a meta-phenylene divalent linking group $R_6$ and $R_7$ are each independently chosen from hydrogen and methyl; and $R_2$ is chosen from phenyl and heteroaryl, each of which is optionally substituted.

16. A compound of claim 1 chosen from 1-(2-Methoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2-methoxy-phenyl)-3-{3-[8-(pyridin-4-ylmethoxy)-imidazo[1,2-a]pyrazin-6-yl]-phenyl}urea;

1-(2-Chloro-5-trifluoromethyl-phenyl)-3-{3-[8-(pyridin-4-ylmethoxy)-imidazo[1,2-a]pyrazin-6-yl]-phenyl}-urea;

1-(2-Fluoro-5-trifluoromethyl-phenyl)-3-{3-[8-(pyridin-4-ylmethoxy)-imidazo[1,2-a]pyrazin-6-yl]-phenyl}-urea;

1-[2-(2-Methoxy-ethoxy)-5-trifluoromethyl-phenyl]-3-{3-[8-(pyridin-4-ylmethoxy)-imidazo[1,2-a]pyrazin-6-yl]-phenyl}-urea;

1-(2-Methoxy-5-nitro-phenyl)-3-{3-[8-(pyridin-4-ylmethoxy)-imidazo[1,2-a]pyrazin-6-yl]-phenyl}-urea;

1-{3-[8-(Pyridin-4-ylmethoxy)-imidazo[1,2-a]pyrazin-6-yl]-phenyl}-3-(3-trifluoromethyl-phenyl)-urea;

1-(2,4-Dimethoxy-5-trifluoromethyl-phenyl)-3-{3-[8-(pyridin-4-ylmethoxy)-imidazo[1,2-a]pyrazin-6-yl]-phenyl}-urea;

1-(5-Chloro-2,4-dimethoxy-phenyl)-3-{3-[8-(pyridin-4-ylmethoxy)-imidazo[1,2-a]pyrazin-6-yl]-phenyl}-urea;

1-(3-Cyano-phenyl)-3-{3-[8-(pyridin-4-ylmethoxy)-imidazo[1,2-a]pyrazin-6-yl]-phenyl}-urea;

1-(2,4-Diethoxy-5-trifluoromethyl-phenyl)-3-{3-[8-(pyridin-4-ylmethoxy)-imidazo[1,2-a]pyrazin-6-yl]-phenyl}-urea; and 1-(5-Chloro-2-methoxy-phenyl)-3-{3-[8-(2-methyl-pyridin-4-ylmethoxy)-imidazo[1,2-a]pyrazin-6-yl]-phenyl}-urea.

17. A compound having the Formula I

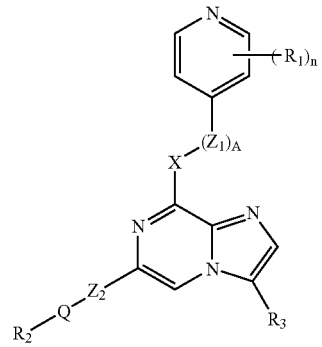

Formula I wherein:

n is 0,1, 2, or 3;

$R_1$ is independently chosen from hydroxy, nitro, cyano, amino, amido, sulfonamido, halo, —CHO, —COOH, $C_1$-$C_6$alkyl, such as $C_3$-$C_6$cycloalkyl, $C_2$-$C_6$ alkenyl, $C_2$-$C_6$ alkynyl, $C_1$-$C_6$ alkoxy, $C_7$cycloalkyl, mono- and di($C_1$-$C_6$ alkyl)amino, mono- and di($C_1$-$C_6$ alkyl)amino ($C_1$-$C_6$alkyl), $C_1$-$C_6$haloalkyl, $C_1$-$C_6$haloalkoxy, ($C_1$-$C_6$alkoxy)$C_1$-$C_6$alkoxy, amino($C_1$-$C_6$alkyl), $C_1$-$C_6$alkylthio, oxo, heteroaryl, and —(C=O)$R_{13}$ wherein $R_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, phenyl, and heteroaryl;

$R_3$ is chosen from hydrogen, optionally substituted $C_1$-$C_6$ alkyl, such as optionally substituted $C_3$-$C_6$cycloalkyl, optionally substituted $C_7$cycloalkyl, optionally substituted (heterocycloalkyl)$C_0$-$C_4$alkyl, and optionally substituted (heteroaryl)$C_0$-$C_4$alkyl;

A is 3 or 4;

$Z_1$ is —$CR_4R_5$— wherein each $R_4$ and $R_5$ is chosen from independently hydrogen, $C_1$-$C_6$ alkyl, and halo;

$Z_2$ is a divalent linking group chosen from para-phenylene, meta-phenylene, ortho-phenylene, and naphthylene, said divalent linking group being substituted with one group $R_2$—Q—, where Q is

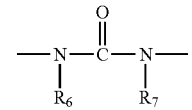

wherein $R_6$ and $R_7$ are each independently chosen from hydrogen, $C_1$-$C_6$ alkyl, optionally substituted phenyl, and optionally substituted heteroaryl;

X is NR;

R is chosen from hydrogen, $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, $C_2$-$C_6$ alkynyl, optionally substituted phenyl and optionally substituted heteroaryl; and $R_2$ is selected from substituted $C_1$-$C_7$alkyl, such as substituted $C_3$-$C_7$cycloalkyl, substituted ($C_3$-$C_7$cycloalkyl) $C_1$-$C_7$ alkyl, substituted heterocycloalkyl, (heterocycloalkyl)$C_1$-$C_2$ alkyl, substituted ($C_1$-$C_6$alkoxy)$C_0$-$C_6$alkyl, substituted ($C_1$-$C_6$alkoxy)$C_1$-$C_6$alkoxy, substituted phenyl, and substituted heteroaryl, wherein said substituted phenyl and substituted heteroaryl are each substituted with one or more substituents chosen from hydroxy, —CHO, —COOH, —CONH$_2$, and —CONHOH, optionally substituted $C_2$-$C_6$ alkenyl, optionally substituted $C_2$-$C_6$alkynyl, optionally substituted $C_1$-$C_6$hydroxyalkyl, optionally substituted $C_1$-$C_6$hydroxyalkoxy, (mono- and di-$C_1$-$C_6$alkylamino)$C_1$-$C_6$alkoxy, optionally substituted mono- and di($C_1$-$C_6$ alkyl)amino($C_1$-$C_6$alkyl), optionally substituted ($C_1$-$C_6$alkoxy)($C_1$-$C_6$alkylamino)$C_0$-$C_6$alkyl, optionally substituted ($C_1$-$C_6$alkoxy)($C_1$-$C_6$alkoxy)$C_1$-$C_6$alkoxy, optionally substituted heterocycloalkyl, optionally substituted aryl, optionally substituted heteroaryl, optionally substituted —$C_1$-$C_6$alkyl(C=O)OR$_8$, optionally substituted —$C_0$-$C_6$alkyl(C=O)NR$_8$R$_9$, optionally substituted —$C_1$-$C_6$alkylNR$_8$(SO$_2$)R$_9$, optionally substitute —$C_0$-$C_6$alkylNR$_8$(C=O)R$_9$, optionally substituted —$C_0$-$C_6$alkyl(SO$_2$)R$_8$, optionally substituted —$C_0$-$C_6$alkylNR$_8$(C=O)NR$_9$R$_{10}$ where R$_8$, R$_9$, and R$_{10}$ are independently chosen from hydrogen, hydroxy, $C_1$-$C_6$alkyl, $C_1$-$C_6$alkoxy, $C_3$-$C_7$cycloalkyl, and heterocycloalkyl, -L-G, where L is chosen from optionally substituted $C_1$-$C_2$alkyl, optionally substituted $C_0$-$C_2$alkoxy, —(C=O)—, and optionally substituted —($C_1$-$C_2$alkyl)(C=O)—, and G is chosen from optionally substituted heterocycloalkyl, optionally substituted $C_3$-$C_7$cycloalkyl, optionally substituted aryl, and optionally substituted heteroaryl, except that -L-G is not —O-phenyl; and wherein said substituted phenyl and substituted heteroaryl, are each further optionally substituted with one or more substituents chosen from hydroxy, nitro, cyano, amino, sulfonamido, halo, $C_1$-$C_6$ alkyl, such as $C_3$-$C_7$cycloalkyl, ($C_1$-$C_6$ alkoxy)$C_0$-$C_6$alkyl, ($C_1$-$C_6$alkoxy)$C_1$-$C_6$alkoxy, $C_7$cycloalkyl, amino$C_1$-$C_6$alkyl, mono- and di($C_1$-$C_6$ alkyl)amino-$C_1$-$C_6$haloalkyl, $C_1$-$C_6$haloalkoxy, $C_2$-$C_6$alkenyl, $C_2$-$C_6$alkynyl, $C_1$-$C_6$alkylthio, oxo, $C_1$-$C_6$alkylester, phenoxy, and —(C=O)R$_{13}$, wherein R$_{13}$ is chosen from $C_1$-$C_6$ alkyl, such as $C_3$-$C_6$cycloalkyl, $C_7$cycloalkyl, $C_2$-$C_6$ alkanoyl, $C_1$-$C_6$alkoxycarbonyl, heterocycloalkyl, and heteroaryl.

18. A compound of claim 17, wherein $Z_2$ is meta-phenylene substituted with $R_2$—Q—.

19. A compound of claim 17, wherein $R_6$ and $R_7$ are each independently chosen from hydrogen and methyl.

20. A compound of claim 19, wherein $R_6$ and $R_7$ are hydrogen.

21. A compound of claim 17, wherein R is chosen from hydrogen; $C_1$-$C_6$ alkyl, such as $C_3$-$C_6$cycloalkyl, $C_7$cycloalkyl, amino($C_1$-$C_6$ alkyl), $C_1$-$C_3$haloalkyl, $C_2$-$C_6$alkenyl, and $C_2$-$C_6$ alkynyl.

22. A compound of claim 21, wherein R is chosen from hydrogen and $C_1$-$C_4$alkyl; or R is amino($C_1$-$C_4$alkyl).

23. A compound of claim 22, wherein R is hydrogen.

24. A compound of claim 17, wherein $R_3$ is chosen from hydrogen and $C_1$-$C_4$alkyl.

25. A compound of claim 24, wherein $R_3$ is hydrogen.

26. A compound of claim 17, wherein n is 0 and $R_1$ is absent.

27. A compound of claim 17, wherein $R_2$ is chosen from phenyl and heteroaryl, each of which is optionally substituted.

28. A compound of claim 17, wherein $R_1$ is chosen from hydroxy, cyano, halo, $C_1$-$C_2$alkyl, $C_1$-$C_2$alkoxy, $C_1$-$C_2$haloalkyl, and $C_1$-$C_2$haloalkoxy.

29. A compound of salt of claim 28, wherein $R_1$ is chosen from halo, methyl, and methoxy.

30. A compound chosen from 1-(3-{8-[(Pyridin-4-ylmethyl)-amino]-imidazo[1,2-a]pyrazin-6-yl}-phenyl)-3-m-tolyl-urea;

1-(3-Chloro-phenyl)-3-(3-{8-[(pyridin-4-ylmethyl)-amino]-imidazo[1,2-a]pyrazin-6-yl}-phenyl)-urea;

1-(4-Methyl-3-trifluoromethyl-phenyl)-3-(3-{8-[(pyridin-4-ylmethyl)-amino]-imidazo[1,2-a]pyrazin-6-yl}-phenyl)-urea;

1-(5-Chloro-2-methoxy-phenyl)-3-(3-{8-[(pyridin-4-ylmethyl)-amino]-imidazo[1,2-a]pyrazin-6-yl}-phenyl)-urea;

1-(2-Chloro-5-trifluoromethyl-phenyl)-3-(3-{8-[(pyridin-4-ylmethyl)-amino]-imidazo[1,2-a]pyrazin-6-yl}-phenyl)-urea;

1-(2-Fluoro-5-trifluoromethyl-phenyl)-3-{3-[8-(methyl-pyridin-4-ylmethyl-amino)-imidazo[1,2-a]pyrazin-6-yl]-phenyl}-urea;

1-(5-Chloro-2-methoxy-phenyl)-3-{3-[8-(methyl-pyridin-4-ylmethyl-amino)-imidazo[1,2-a]pyrazin-6-yl]-phenyl}-urea;

1-(2-Chloro-5-trifluoromethyl-phenyl)-3-{3-[8-(methyl-pyridin-4-ylmethyl-amino)-imidazo[1,2-a]pyrazin-6-yl]-phenyl}-urea;

1-{3-[8-(2-Pyridin-4-yl-ethylamino)-imidazo[1,2-a]pyrazin-6-yl]-phenyl}-3-(3-trifluoromethyl-phenyl)-urea;

1-(5-Chloro-2-methoxy-phenyl)-3-{3-[8-(2-pyridin-4-yl-ethylamino)-imidazo[1,2-a]pyrazin-6-yl]-phenyl}-urea;

1-(2-Fluoro-5-trifluoromethyl-phenyl)-3-(3-{8-[(pyridin-4-ylmethyl)-amino]-imidazo[1,2-a]pyrazin-6-yl}-phenyl)-urea;

1-(2-Methoxy-5-trifluoromethyl-phenyl)-3-(3-{8-[(pyridin-4-ylmethyl)-amino]-imidazo[1,2-a]pyrazin-6-yl}-phenyl)-urea;

1-(2-Methoxy-5-trifluoromethyl-phenyl)-3-{3-[8-(methyl-pyridin-4-ylmethyl-amino)-imidazo[1,2-a]pyrazin-6-yl]-phenyl}-urea;

1-(2-Methoxy-5-nitro-phenyl)-3-{3-[8-(methyl-pyridin-4-ylmethyl-amino)-imidazo[1,2-a]pyrazin-6-yl]-phenyl}-urea;

1-(5-Chloro-2,4-dimethoxy-phenyl)-3-(3-{8-[(pyridin-4-ylmethyl)-amino]-imidazo[1,2-a]pyrazin-6-yl}-phenyl)-urea 1-(3-{8-[(Pyridin-4-ylmethyl)-amino]-imidazo[1,2-a]pyrazin-6-yl}-phenyl)-3-(2,4,5-trichloro-phenyl)-urea;

1-(5-Chloro-2,4-dimethoxy-phenyl)-3-{3-[8-(methyl-pyridin-4-ylmethyl-amino)-imidazo[1,2-a]pyrazin-6-yl]-phenyl}-urea;

1-{3-[8-(Methyl-pyridin-4-ylmethyl-amino)-imidazo[1,2-a]pyrazin-6-yl]-phenyl}-3-(2,4,5-trichloro-phenyl)-urea;

1-(2-Methoxy-5-nitro-phenyl)-3-(3-{8-[(pyridin-4-ylmethyl)-amino]-imidazo[1,2-a]pyrazin-6-yl}-phenyl)-urea;

1-(2-Ethoxy-5-trifluoromethyl-phenyl)-3-(3-{8-[(pyridin-4-ylmethyl)-amino]-imidazo[1,2-a]pyrazin-6-yl}-phenyl)-urea;

1-(2-Isopropoxy-5-trifluoromethyl-phenyl)-3-(3-{8-[(pyridin-4-ylmethyl)-amino]-imidazo[1,2-a]pyrazin-6-yl}-phenyl)-urea;

1-(2,4-Dimethoxy-5-trifluoromethyl-phenyl)-3-(3-{8-[(pyridin-4-ylmethyl)-amino]-imidazo[1,2-a]pyrazin-6-yl}-phenyl)-urea;

1-(2,4-Dimethoxy-5-trifluoromethyl-phenyl)-3-{3-[8-(methyl-pyridin-4-ylmethyl-amino)-imidazo[1,2-a]pyrazin-6-yl]-phenyl}-urea;

1-(4-Ethoxy-3-trifluoromethyl-phenyl)-3-(3-{8-[(pyridin-4-ylmethyl)-amino]-imidazo[1,2-a]pyrazin-6-yl}phenyl)-urea;

1-(5-Chloro-2-phenoxy-phenyl)-3-(3-{8-[(pyridin-4-ylmethyl)-amino]-imidazo[1,2-a]pyrazin-6-yl}phenyl)-urea;

1-(4-Fluoro-3-trifluoromethyl-phenyl)-3-(3-{8-[(pyridin-4-ylmethyl)-amino]-imidazo[1,2-a]pyrazin-6-yl}phenyl)-urea;

1-[2-(2-Methoxy-ethoxy)-5-trifluoromethyl-phenyl]-3-(3-{8-[(pyridin-4-ylmethyl)-amino]imidazo[1,2-a]pyrazin-6-yl}-phenyl)-urea;

1-[2-(2-Methoxy-ethoxy)-5-trifluoromethyl-phenyl]-3-{3-[8-(methyl-pyridin-4-ylmethyl-amino)-imidazo[1,2-a]pyrazin-6-yl]-phenyl}-urea;

1-(2,4-Diethoxy-5-trifluoromethyl-phenyl)-3-(3-{8-[(pyridin-4-ylmethyl)-amino]-imidazo[1,2-a]pyrazin-6-yl}-phenyl)-urea;

1-(2,4-Diethoxy-5-trifluoromethyl-phenyl)-3-{3-[8-(methyl-pyridin-4-ylmethyl-amino)-imidazo[1,2-a]pyrazin-6-yl]-phenyl}-urea;

1-[2-(2-Hydroxy-ethoxy)-5-trifluoromethyl-phenyl]-3-(3-{8-[(pyridin-4-ylmethyl)-amino]-imidazo[1,2-a]pyrazin-6-yl}-phenyl)-urea;

{2-[3-(3-{8-[(Pyridin-4-ylmethyl)-amino]-imidazo[1,2-a]pyrazin-6-yl}-phenyl)-ureido]-4-trifluoromethyl-phenoxy}-acetic acid;

1-[2-(2-Methylamino-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(2-Dimethylamino-ethoxy)-5-trifluoromethyl-phenyl]-3-(3-{8-[(pyridin-4-ylmethyl)-amino]-imidazo[1,2-a]pyrazin-6-yl}-phenyl) urea;

1-(3-Chloro-4-hydroxymethyl-phenyl)-3-(3-{8-[(pyridin-4-ylmethyl)-amino]-imidazo[1,2-a]pyrazin-6-yl}-phenyl)-urea;

1-[5-Chloro-2-([1,3]dioxolan-2-ylmethoxy)-phenyl]-3-(3-{8-[(pyridin-4-ylmethyl)-amino]-imidazo[1,2-a]pyrazin-6-yl}-phenyl)-urea;

1-[5-Chloro-2-(2-hydroxy-ethoxy)-phenyl]-3-(3-{8-[(pyridin-4-ylmethyl)-amino]-imidazo[1,2-a]pyrazin-6-yl}-phenyl)-urea;

1-[5-Chloro-2-(2-methylamino-ethoxy)-phenyl]-3-(3-{8-[(pyridin-4-ylmethyl)-amino]-imidazo[1,2-a]pyrazin-6-yl}-phenyl)-urea;

1-[5-Chloro-2-(2-dimethylamino-ethoxy)-phenyl]-3-(3-{8-[(pyridin-4-ylmethyl)-amino]-imidazo[1,2-a]pyrazin-6-yl}-phenyl)-urea;

1-[2-(2-Piperazin-1-yl-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(2-Morpholin-4-yl-ethoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(3-Hydroxy-propoxy)-5-trifluoromethyl-phenyl]-3-(3-{8-[(pyridin-4-ylmethyl)-amino]-imidazo[1,2-a]pyrazin-6-yl}-phenyl)-urea;

1-[2-(3-Methylamino-propoxy)-5-trifluoromethyl-phenyl]-3-(3-{8-[(pyridin-4-ylmethyl)-amino]-imidazo[1,2-a]pyrazin-6-yl}-phenyl)-urea;

1-[5-Chloro-2-(3-hydroxy-propoxy)-phenyl]-3-(3-{8-[(pyridin-4-ylmethyl)-amino]-imidazo[1,2-a]pyrazin-6-yl}-phenyl)-urea;

1-(3-{8-[(2-Amino-ethyl)-pyridin-4-ylmethyl-amino]-imidazo[1,2-a]pyrazin-6-yl}-phenyl)-3-(4-methoxy-3-trifluoromethyl-phenyl)-urea;

1-(3-{8-[(Pyridin-4-ylmethyl)-amino]-imidazo[1,2-a]pyrazin-6-yl}-phenyl)-3-[2-(2-pyrrolidin-1-yl-ethoxy)-5-trifluoromethyl-phenyl]-urea; and 1-(2-Hydroxy-5-trifluoromethyl-phenyl)-3-(3-{8-[(pyridin-4-ylmethyl)-amino]-imidazo[1,2-a]pyrazin-6-yl}-phenyl)-urea.

31. A compound of claim 1, wherein the compound exhibits an $IC_{50}$ of 1 micromolar or less in a standard in vitro assay of $EphB_4$ kinase activity.

32. A compound of claim 31, wherein the compound exhibits an $IC_{50}$ of 500 nanomolar or less in an in vitro assay of $EphB_4$ kinase activity.

33. A compound of claim 32, wherein the compound exhibits an $IC_{50}$ of 100 nanomolar or less in an in vitro assay of $EphB_4$ kinase activity.

34. A compound of claim 1, wherein the compound exhibits an $IC_{50}$ of 500 nanomolar or less in an in vitro assay of PDGF-Rα kinase activity.

35. A compound of claim 1, wherein the compound exhibits an $IC_{50}$ of 500 nanomolar or less in an in vitro assay of c-Kit activity.

36. A compound of claim 35, wherein the compound exhibits an $IC_{50}$ of 100 nanomolar or less in an in vitro assay of c-Kit activity.

37. A compound of claim 1, wherein the compound exhibits an $IC_{50}$ of 1 micromolar or less in an in vitro assay of VEGFR-2 activity.

38. A compound of claim 37 wherein the compound exhibits an $IC_{50}$ of 100 nM or less in an in vitro assay of VEGFR-2 activity.

39. A compound of claim 1, wherein the compound exhibits an $IC_{50}$ of 1 micromolar or less in standard in vitro assay of Tie-2 activity.

40. A compound of claim 39, wherein the compound exhibits an $IC_{50}$ of 500 nM or less in an in vitro assay of Tie-2 activity.

41. A pharmaceutical composition, comprising a compound of claim 1, together with at least one pharmaceutically acceptable carrier or excipient.

42. A pharmaceutical composition of claim 41, wherein the composition is formulated as an injectable fluid, an aerosol, a cream, a gel, a tablet, a capsule, a syrup, ophthalmic solution, or a transdermal patch.

* * * * *